US011471426B2

(12) United States Patent
Tan

(10) Patent No.: US 11,471,426 B2
(45) Date of Patent: Oct. 18, 2022

(54) COMPOSITIONS COMPRISING QUINONE AND/OR QUINOL AND METHODS OF PREPARATIONS AND USE THEREOF

(71) Applicant: American River Nutrition, LLC, Hadley, MA (US)

(72) Inventor: Barrie Tan, Hadley, MA (US)

(73) Assignee: American River Nutrition, LLC, Hadley, MA (US)

( * ) Notice: Subject to any disclaimer, the term of this patent is extended or adjusted under 35 U.S.C. 154(b) by 0 days.

(21) Appl. No.: 16/829,868

(22) Filed: Mar. 25, 2020

(65) Prior Publication Data

US 2021/0113491 A1    Apr. 22, 2021

Related U.S. Application Data

(60) Provisional application No. 62/915,649, filed on Oct. 16, 2019.

(51) Int. Cl.
*A61K 31/12* (2006.01)
*A61K 31/09* (2006.01)
*A61K 9/00* (2006.01)

(52) U.S. Cl.
CPC ............ *A61K 31/12* (2013.01); *A61K 9/0053* (2013.01); *A61K 31/09* (2013.01)

(58) Field of Classification Search
CPC ..................................................... A61K 31/12
See application file for complete search history.

(56) References Cited

U.S. PATENT DOCUMENTS

| | | |
|---|---|---|
| 3,863,633 A | 2/1975 | Ryde et al. |
| 3,867,519 A | 2/1975 | Michaels |
| 3,868,445 A | 2/1975 | Ryde et al. |
| 3,960,150 A | 6/1976 | Hussain et al. |
| 3,963,025 A | 6/1976 | Whitaker et al. |
| 4,186,184 A | 1/1980 | Zaffaroni |
| 4,303,637 A | 12/1981 | Shell et al. |
| 5,443,505 A | 8/1995 | Wong et al. |
| 5,869,079 A | 2/1999 | Wong et al. |
| 6,056,971 A | 5/2000 | Goldman |
| 6,184,255 B1 | 2/2001 | Mae et al. |
| 6,461,842 B1 | 10/2002 | Matsuda et al. |
| 6,623,734 B2 | 9/2003 | Udell et al. |
| 6,762,037 B1 | 7/2004 | Matsuda et al. |
| 6,939,897 B2 | 9/2005 | Fujii et al. |
| 7,105,709 B2 | 9/2006 | Ueda et al. |
| 7,145,044 B2 | 12/2006 | Ueda et al. |
| 7,208,639 B2 | 4/2007 | Ueda et al. |
| 7,320,883 B2 | 1/2008 | Matsuda et al. |
| 7,358,402 B2 | 4/2008 | Ueda et al. |
| 7,364,751 B2 | 4/2008 | Fujii et al. |
| 7,402,413 B2 | 7/2008 | Matsuda et al. |
| 7,445,793 B2 | 11/2008 | Niwa et al. |
| 7,524,993 B2 | 4/2009 | Ueda et al. |
| 7,678,404 B2 | 3/2010 | Shiraishi et al. |
| 7,708,990 B2 | 5/2010 | Fujii et al. |
| 7,754,205 B2 | 7/2010 | Fujii et al. |
| 7,829,080 B2 | 11/2010 | Ueda et al. |
| 7,897,169 B2 | 3/2011 | Ueda et al. |
| 7,910,340 B2 | 3/2011 | Yajima et al. |
| 7,989,006 B2 | 8/2011 | Tan |
| 8,003,828 B2 | 8/2011 | Ueda et al. |
| 8,063,254 B2 | 11/2011 | Ueda et al. |
| 8,067,217 B2 | 11/2011 | Ueda et al. |
| 8,124,072 B2 | 2/2012 | Fantuzzi |
| 8,163,525 B2 | 4/2012 | Matsuda et al. |
| 8,168,618 B2 | 5/2012 | Kawahara et al. |
| 8,173,711 B2 | 5/2012 | Saito et al. |
| 8,293,290 B2 | 10/2012 | Tan |
| 8,506,956 B2 | 8/2013 | Ueda et al. |
| 8,568,779 B2 | 10/2013 | Kanaya et al. |
| 8,574,568 B2 | 11/2013 | Ueda et al. |
| 8,703,155 B2 | 4/2014 | Ueda et al. |
| 8,753,675 B1 | 6/2014 | Chopra |
| 8,853,464 B2 | 10/2014 | Ueda et al. |
| 8,946,303 B2 | 2/2015 | Fujii et al. |
| 9,006,493 B2 | 4/2015 | Kanaya et al. |
| 9,040,747 B2 | 5/2015 | Jikihara et al. |
| 9,295,656 B2 | 3/2016 | Ueda et al. |
| 9,315,839 B2 | 4/2016 | Yajima et al. |
| 9,345,672 B2 | 5/2016 | Fantuzzi |
| 9,388,109 B2 | 7/2016 | Kawachi et al. |
| 9,440,901 B2 | 9/2016 | Kawachi et al. |
| 9,518,004 B2 | 12/2016 | Koga et al. |
| 9,532,957 B2 | 1/2017 | Ueda et al. |
| 9,556,098 B2 | 1/2017 | Kawachi et al. |
| 9,919,017 B2 | 3/2018 | Yamaguchi et al. |
| 9,926,580 B2 | 3/2018 | Yajima et al. |
| 9,949,938 B2 | 4/2018 | Tan |
| 9,981,899 B2 | 5/2018 | Ueda et al. |
| 10,239,811 B2 | 3/2019 | Kanaya et al. |
| 2004/0202740 A1 | 10/2004 | Tan |
| 2005/0069996 A1 | 3/2005 | Yajima et al. |
| 2006/0246565 A1 | 11/2006 | Ueda et al. |
| 2007/0208086 A1 | 9/2007 | Lipshutz |
| 2008/0139649 A1 | 6/2008 | Barrow et al. |
| 2008/0160077 A1 | 7/2008 | Borowy-Borowski |
| 2008/0200732 A1 | 8/2008 | Upare et al. |
| 2010/0168249 A1 | 7/2010 | Kitamura et al. |
| 2011/0123505 A1 | 5/2011 | Ueda et al. |
| 2012/0323009 A1* | 12/2012 | Ikemoto ............... C07D 471/04 546/84 |

(Continued)

OTHER PUBLICATIONS

Jeon et al. CAS: 158:215735, 2013.*
Al Rajabi A, Booth SL, Peterson JW, Choi SW, Suttie JW, Shea MK, et al. Deuterium-labeled phylloquinone has tissue-specific conversion to menaquinone-4 among Fischer 344 male rats. J Nutr. 2012;142(5):841-5. Epub Mar. 23, 2012.
Campia I, Lussiana C, Pescarmona G, Ghigo D, Bosia A, Riganti C. Geranylgeraniol prevents the cytotoxic effects of mevastatin in THP-1 cells, without decreasing the beneficial effects on cholesterol synthesis. British journal of pharmacology. 2009,158(7):1777-86. Epub Nov. 6, 2009.

(Continued)

*Primary Examiner* — Rei Tsang Shiao
(74) *Attorney, Agent, or Firm* — Troutman Pepper Hamilton Sanders LLP

(57) ABSTRACT

The present embodiments are directed to compositions of quinones and/or quinols, such as, but not limited to, ubiquinone and/or ubiquinol, vitamin E quinone and/or vitamin E quinol, vitamin K quinone and/or vitamin K quinol, menaquinones and/or menaquinols, and pyrroloquinoline quinone and/or pyrroloquinoline quinol, and methods for preparations and use thereof. The present embodiments are also directed to compositions of reduced forms of curcuminoid and methods for preparations and use thereof.

20 Claims, 7 Drawing Sheets

(56) References Cited

U.S. PATENT DOCUMENTS

2013/0142767 A1 6/2013 Yamaguchi et al.
2015/0010520 A1 1/2015 Tan

OTHER PUBLICATIONS

Crane FL, Hatefi Y, RL Lester and C Widmer (1957). Isolation of a quinone from beef heart mitochondria, BBA 25: 220-221.
Grammel, H, and Ghosh R. "Redox-State Dynamics of Ubiquinone-10 Imply Cooperative Regulation of Photosynthetic Membrane Expression in Rhodospirillum Rubrum." Journal of Bacteriology, American Society for Microbiology (ASM), Jul. 2008.
Harshman SG, Shea MK, Fu X, Grusak MA, Smith D, Lamon-Fava S, et al. Atorvastatin Decreases Renal Menaquinone-4 Formation in C57BL/6 Male Mice. J Nutr. 2019;5 149(3):416-21. Epub Feb. 13, 2019.
Hirota Y, Nakagawa K, Sawada N, Okuda N, Suhara Y, Uchino Y, et al. Functional characterization of the vitamin K2 biosynthetic enzyme UBIAD1. PloS one. 2015;10(4): e0125737. Epub Apr. 16, 2015.
Houston MC, Treatment of Hypertension with Nutrition and Nutraceutical Supplements, Alternative and Complementary Therapies, vol. 25, Feb. 2019; and references on CoQ10 therein.
Marcuzz A, Piscianz E, Zweyer M, Bortul R, Loganes C, Girardelli M, et al. Geranylgeraniol and Neurological Impairment: Involvement of Apoptosis and Mitochondrial Morphology. International journal of molecular sciences. 2016;17(3):365. Epub Mar. 16, 2016.
Mattila P, Lehtonen M, and Kumpulainen J, Comparison of In-Line Connected Diode Array and Electrochemical Detectors in the High-Performance Liquid Chromatographic Analysis of Coenzymes Q9 and Q10 in Food Materials, The Journal of Agricultural and Food Chemistry (2000).,20 vol, 48, No. 4, p. 1229-1233.
Meganathan R., Kwon, O., "Biosynthesis of Menaquinone (Vitamin K2) and Ubiquinone (CoQ)", ASMscience.org, Dec. 23, 2009.
Nakagawa K, Hirota Y, Sawada N, Yuge N, Watanabe M, Uchino Y, et al. Identification of UBIAD1 as a novel human menaquinone-4 biosynthetic enzyme. Nature. 2010;468(7320):117-21. 25 Epub Oct. 19, 2010.
Nickerson ML, Bosley AD, Weiss JS, Kostiha BN, Hirota Y, Brandt W, et al. The UBIAD1 prenyltransferase links menaquinone-4 [corrected] synthesis to cholesterol metabolic enzymes. Human mutation. 2013;34(2):317-29. Epub Nov. 22, 2012.
Roginsky VA, Mohr D, Stocker R, Reduction of ubiquinone-1 by ascorbic acid is a catalytic and reversible process controlled by the concentration of molecular oxygen, Redox Report (1996) 2(1): p. 55-62.
Semeco, Arlene (2017), Nine Benefit of Coenzyme Q10 (www.healthline.com), Oct. 12, 2017; and references in CoQ10 therein.
Tan B, Mueller AM. Tocotrienols in Cardiometabolic Diseases. In: Watson R, Preedy V, editors. Tocotrienols: Vitamin E beyond Tocopherol: AOCS/CRC Press; 2008. p. 257-73.
WholeFoods Interview, Jun. 2007 with Frederick Crane by Richard Passwater.
www.noberlprize.org., Peter Mitchell Nobel Lecture, Dec. 8, 1978.
WholeFoods, Mar. 2019: p. 64-68, The functions and absorption of the Ubiquinone and Ubiquinol.
WholeFoods, Apr. 2019: p. 42-50, The absorption of Ubiquinone and Ubiquinol forms of Coenzyme Q10.
Thomas et al. "Dietary Cosupplementation With Vitamin E and Coenzyme Q10 Inhibits Atherosclerosis in Apolipoprotein E Gene Knockout Mice". Arterioscler Thromnb Vase Biol. Apr. 2001, Vo 21, pp. 585-593, Abstract; p. 586, col. 1, para 3; p. 588, col. 2, para 2, Fig 3; p. 590, col. 2, para 2.
Non-Final Office Action dated Feb. 11, 2017 in U.S. Appl. No. 15/237,617.

* cited by examiner

COMPOSITIONS COMPRISING QUINONE AND/OR QUINOL AND METHODS OF PREPARATIONS AND USE THEREOF

CROSS-REFERENCE TO RELATED APPLICATIONS

This application claims priority to U.S. Provisional Application No. 62/915,649, filed Oct. 16, 2019, which is incorporated herein by reference in its entirety.

FIELD

Embodiments disclosed herein are directed to compositions of quniones and/or quinols, such as, but not limited to, ubiquinone and/or ubiquinol, vitamin E quinone and/or vitamin E quinol, vitamin K quinone and/or vitamin K quinol, and pyrroloquinoline quinone and/or pyrroloquinoline quinol, and methods for preparations and use thereof. Embodiments disclosed herein are also directed to compositions of reduced forms of curcuminoid and methods for preparations and use thereof.

BACKGROUND

"Quinone" and "quinol" refer to benzo-diketone and benzo-diol, respectively. CoEnzyme Q is a form of quinone and it goes by names of CoQ10, Co-Enzyme 10, Coenzyme Q10, ubidecarenone, and ubiquinone, all of which subscribe to the chemical 2-[(2E,6E,10E,14E,18E,22E,26E,30E,34E)-3,7,11,15,19,23,27,31,35,39-decamethyltetraconta-2,6,10,14,18,22,26,30,34,38-decaenyl]-5,6-dimethoxy-3-methyl-cyclohexa-2,5-diene-1,4-dione. Ubiquinol is the reduced state of ubiquinone that is the oxidized state of ubiquinol. Ubiquinone, also known as Coenzyme Q10, (CAS 303-98-0; C59 H90 O4; MW-863) is a yellow-orange powder with a melting point ("MP") between 48-52° C. and ubiquinol (CAS 992-78-9; $C_{59}H_{92}O_4$; molecular weight: 865) is a cream-yellow powder with a MP between 45-47° C. The "deca" or "10" refers to the ten repeating isoprenyl units in the unsaturated hydrocarbon tail (side-chain) of both isomers. Ubiquinone and Ubiquinol are chemically close analogous except for their oxidation-reduction species. Hereinafter, the ubiquinol will be designated as "CoQnol" and the ubiquinone will be designated as "CoQone," and when speciation is not required (and can mean both "CoQone" and "CoQnol"), "CoQ" will be designated.

CoQ10 was discovered by Frederick Crane in 1957 at the University of Wisconsin, Madison (Crane, 1957). Dr. Crane first named this compound "CoenzymeQ-275" because it restored a mitochondrial enzyme activity (hence coenzyme), had a quinone moiety (hence Q) and absorbed at 275 nm (hence 275). He renamed this compound "CoenzymeQ10" when he found out its side-chain had 10 isoprene units (hence 10) (Passwater, 2007). Today CoQ10 has numerous ubiquitous functions that, among other things, secured Peter Mitchell the 1978 Nobel Prize for his mechanistic discovery of ATP synthesis that involved CoQnol-CoQone redox pair (Mitchell, 1978). Much of the benefits of CoQ10 had been published in two easy-to-read books (Barry, 2010 and Lund, 2014) and an online summary (Semeco, 2017 and references therein). Each of the cited references is hereby incorporated by reference in its entirety.

CoQ10 is not a true enzyme but acts as a cofactor to help the catalytic function of an enzyme protein. In the cell—intracellularly in the mitochondria—CoQnol is part of the electron transport chain allowing the aerobic cellular respiration to produce ATP—the currency of mammalian energy. In humans, such aerobic respiration constitutes 95% of energy production, particularly important in dark organs (heart, liver, kidney, pancreas, muscles, thyroid, etc.) where energy demand is greatest. Because of its presence, CoQ10 is "ubiquitous" in many tissues and cells. CoQnol is required by all humans because about 90% of blood-borne CoQ is CoQnol. It is also true that CoQone-CoQnol redox pair is used interchangeably in the human body. However, there are specific needs uniquely suited for an individual or an animal in need of the reduced state CoQnol. For example, this applies to older individuals and people with: a) impaired CoQone-to-CoQnol conversion; b) deficiency for producing the protein NAD[P]H-dependent enzyme that brings about this reduction; c) deficiency in CoQ10 biosynthesis; d) increased tissue demand because of disease consequence; e) mitochondria-related diseases; f) impaired CoQ biosynthesis because of medications (for example statins). Currently available methods for preparing CoQnol from CoQone are limited. Thus, there is a need for new methods for preparing such compounds. The embodiments provided for herein satisfies these needs as well as others.

SUMMARY OF EMBODIMENTS

In some embodiments, compositions of quinones and/or quinols are provided. The composition comprises quinone and/or quinol, which can have, for example, a formula as described herein. In some embodiments, methods of preparing the compositions and quinols are provided as described herein. In some embodiments, formulations of the composition are provided as described herein. In some embodiments, methods of treating, improving, preventing, or reversing the health or medical conditions described herein are provided.

In some embodiments, the composition is a composition comprising:

Compound A having the formula of

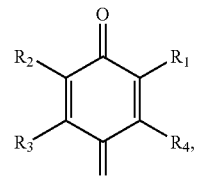

Formula I

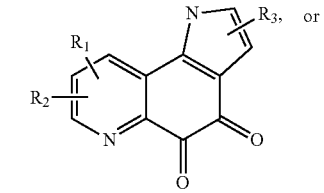

Formula VII or

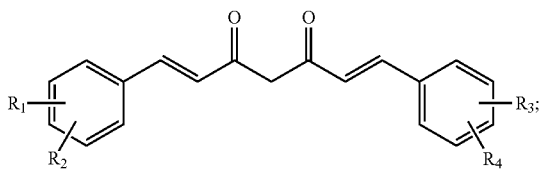

Formula VIII

Compound B having the formula of

Formula II

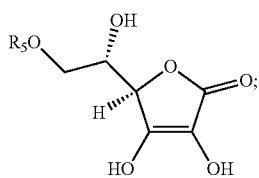

and optionally a non-toxic solvent, wherein the solvent can be free of or is not ethanol, wherein $R_1$, $R_2$, $R_3$, $R_4$, $R_5$, and $R_8$ are as provided for herein and, for example, can be selected from the respective groups of chemical moieties described herein. Also provided are processes for preparing these compositions and compounds described herein.

In some embodiments, the composition is a composition comprising:

Compound A having the formula of

Formula I

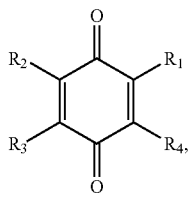

Formula VII

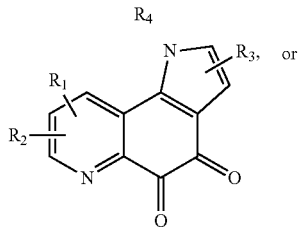

Formula VIII

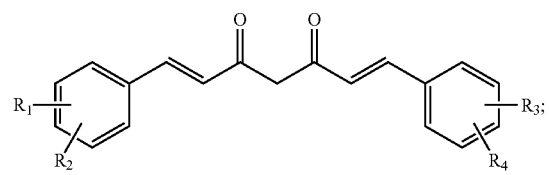

Compound B having the formula of

Formula II

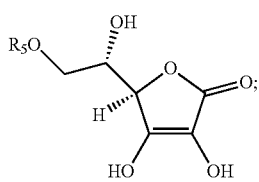

Compound C having the formula of

Formula III

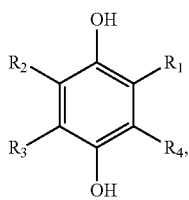

Formula VI

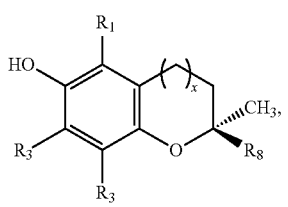

Formula IX

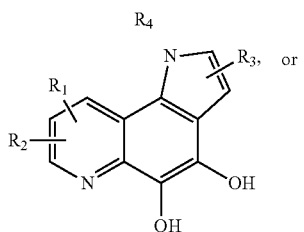

Formula X

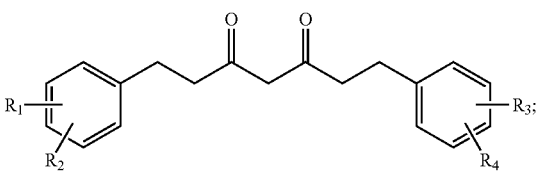

Compound D having the formula of

Formula IV

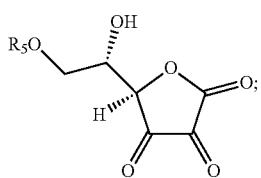

and optionally a solvent, wherein the solvent is free of or is not ethanol.

wherein $R_1$, $R_2$, $R_3$, $R_4$, $R_5$, and $R_8$ are as provided for herein and, for example, can be selected from the respective groups of chemical moieties described herein. Also provided are processes for preparing these compositions and compounds described herein.

In some embodiments, the composition is a composition comprising:

Compound C having the formula of

Formula III

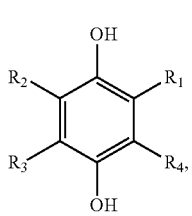

Formula VI

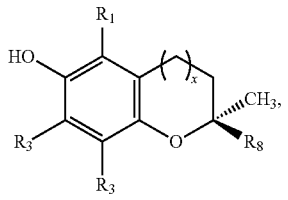

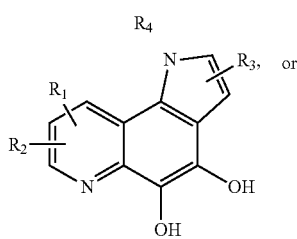

Formula IX

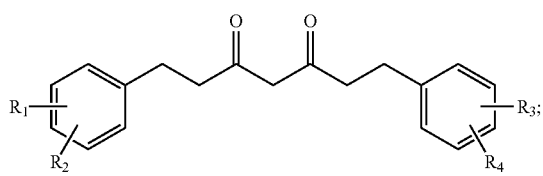

Compound D having the formula of

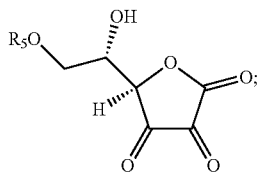

Formula IV and optionally a non-toxic solvent, wherein the solvent is free of or is not ethanol wherein $R_1$, $R_2$, $R_3$, $R_4$, $R_5$, and $R_8$ are as provided for herein and, for example, can be selected from the respective groups of chemical moieties described herein. Also provided are processes for preparing compositions and compounds described herein.

In some embodiments, the compositions can be in any form such as the forms suitable for oral consumption or oral administration are also provided herein. In some embodiments, the form is a softgel, a capsule, 2-piece liquid-filled capsule, a bar, confectionary, chocolate, a powder, an oral suspension, a tablet, a pill, a hard-shell, a truffle, a ganache, a truffle ganache, a gum, or a chewable form. In some embodiments, the methods of producing the compositions further comprise forming the composition into a softgel, a capsule, 2-piece liquid-filled capsule, a bar, confectionary, chocolate, a powder, an oral suspension, a tablet, a pill, a hard-shell, a truffle, a ganache, a truffle ganache, a gum, or a chewable form.

In some embodiments, methods of treating, improving, preventing, or reversing the health or medical conditions comprising administering to a subject the compositions described herein are also provided. In some embodiments, the compositions described herein for use in treating, improving, preventing, or reversing the health or medical conditions are also provided herein. In some embodiments, also provided are uses of the compositions described herein in the manufacture of a formulation for the treatment, improvement, prevention or reverse of the medical or health conditions described herein. In some embodiments, the condition is a statin-induced CoQ10 depletion, cardiac function, bone mineralization, joint osteophyte growth, a gall or kidney stone, arterial calcification, statin-induced myopathy, blood-thinning med-induced dementia, myogenesis, sarcopenia, cancer-induced cachexia, fibromyalgia, general metabolic synthesis of proteins, CoQ10, or Vitamin K2, mitochondrial function or reproduction, neurological regeneration, low energy, fatigue, energy deficit, nonalcoholic fatty liver, and the like. In some embodiments, also provided are methods or uses of the compositions described herein for improving increasing bioavailability and bioaccessibility of the compounds in the compositions and increasing absorption into an endothelial or internal surface skin of a dermatological composition.

DESCRIPTION OF EMBODIMENTS

Provided herein are methods of preparing quinol from quinone, such as, but not limited to, ubiquinol from ubiquinone, vitamin E quinol from vitamin E quinone, vitamin K quinol from vitamin K, menaquinols from menaquinones, and pyrroloquinoline quinol from pyrroloquinoline quinone, Also provided herein are, methods of preparing quinol from quinone, which can be used, for example, to prepare reduced forms of curcuminoid.

Unless defined otherwise, all technical and scientific terms have the same meaning as is commonly understood by one of ordinary skill in the art to which the embodiments disclosed belongs.

As used herein, the terms "a" or "an" mean that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

Figure 1:
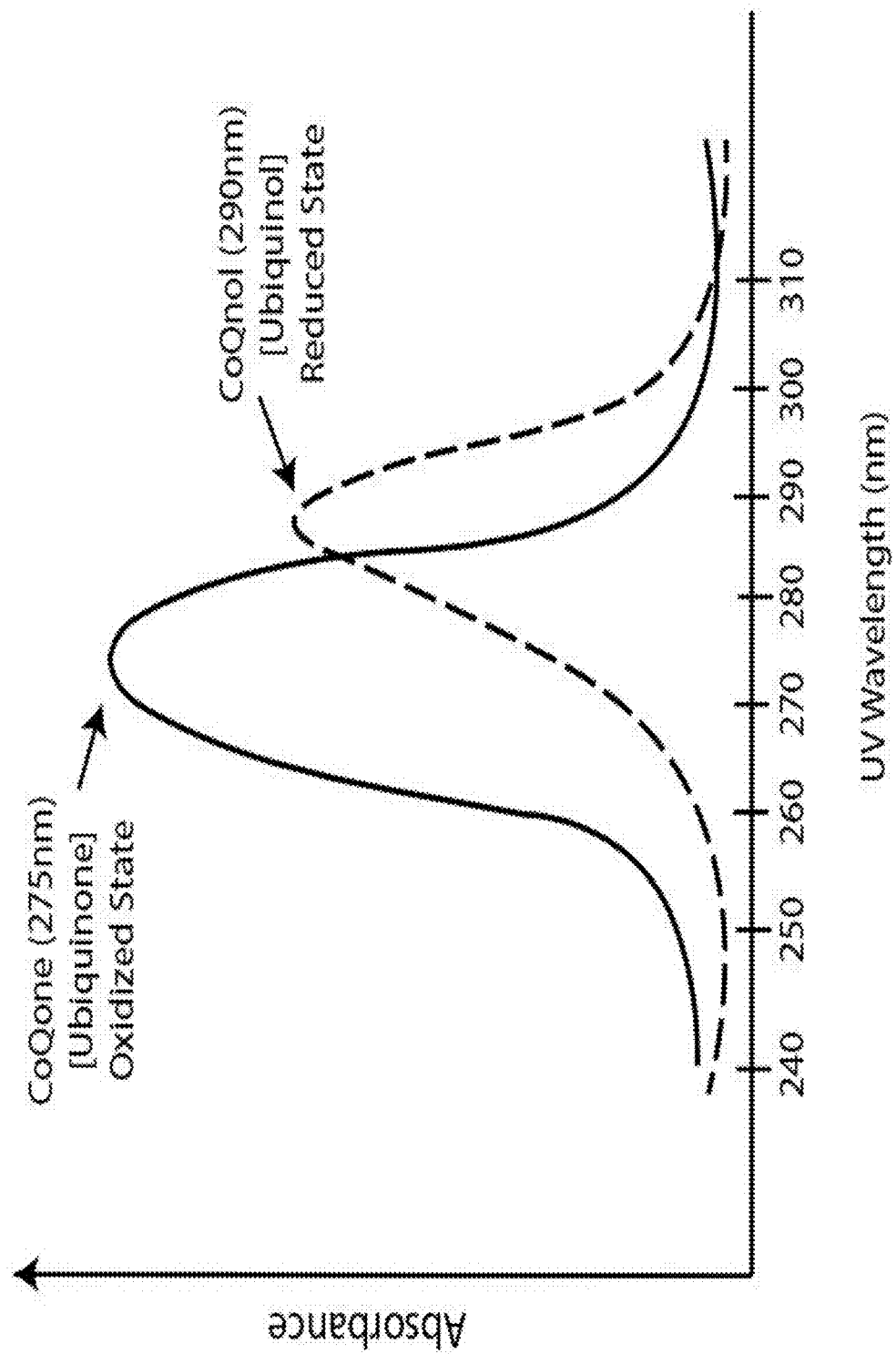
FIG. 1: UV absorption spectra of CoQone and CoQnol from Grammel and Ghosh (Journal of Bacteriology, American Society for Microbiology, July 2008, 2008).

As used herein, the term "absorption" means CoQone and CoQnol have characteristic UV absorption spectra that peaked at 275 nm and 290 nm, respectively (Grammel and Ghosh, 2008). See FIG. 1.

As used herein, the term "access" means a state where two solvents or solutions are homogenous (fully miscible) such that their physical contact facilitates a redox reaction to occur.

As used herein, the term "acylamino" means an amino group substituted by an acyl group (e.g., —O—C(=O)—H or —O—C(=O)-alkyl). An example of an acylamino is —NHC(=O)H or —NHC(=O)CH₃. The term "lower acylamino" refers to an amino group substituted by a lower acyl group (e.g., —O—C(=O)—H or —O—C(=O)—C$_{1-6}$alkyl). An example of a lower acylamino is —NHC(=O)H or —NHC(=O)CH₃.

As used herein, the term "alkenyl" means a straight or branched alkyl group having one or more double carbon-carbon bonds and 2-20 carbon atoms, including, but not limited to, ethenyl, 1-propenyl, 2-propenyl, 2-methyl-1-propenyl, 1-butenyl, 2-butenyl, and the like. In some embodiments, the alkenyl chain is from 2 to 10 carbon atoms in length, from 2 to 8 carbon atoms in length, from 2 to 6 carbon atoms in length, or from 2 to 4 carbon atoms in length.

The terms "alkoxy", "phenyloxy", "benzoxy" and "pyrimidinyloxy" refer to an alkyl group, phenyl group, benzyl group, or pyrimidinyl group, respectively, each optionally substituted, that is bonded through an oxygen atom. For example, the term "alkoxy" means a straight or branched —O-alkyl group of 1 to 20 carbon atoms, including, but not limited to, methoxy, ethoxy, n-propoxy, isopropoxy, t-butoxy, and the like. In some embodiments, the alkoxy chain is from 1 to 10 carbon atoms in length, from 1 to 8 carbon atoms in length, from 1 to 6 carbon atoms in length, from 1 to 4 carbon atoms in length, from 2 to 10 carbon atoms in length, from 2 to 8 carbon atoms in length, from 2 to 6 carbon atoms in length, or from 2 to 4 carbon atoms in length.

As used herein, the term "alkyl" means a saturated hydrocarbon group, which is straight-chained or branched. An alkyl group can contain from 1 to 20, from 2 to 20, from 1 to 10, from 2 to 10, from 1 to 8, from 2 to 8, from 1 to 6, from 2 to 6, from 1 to 4, from 2 to 4, from 1 to 3, or 2 or 3 carbon atoms. Examples of alkyl groups include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, 4,4-dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

As used herein, the term "allylamino" means an amino group substituted by an alkyl group having from 1 to 6 carbon atoms. An example of an alkylamino is —NHCH₂CH₃.

As used herein, the term "alkylene" or "alkylenyl" means a divalent alkyl linking group. An example of an alkylene (or alkylenyl) is methylene or methylenyl (—CH₂—).

As used herein, the term "alkylthio" means an —S-alkyl group having from 1 to 6 carbon atoms. An example of an alkylthio group is —SCH₂CH₃.

As used herein, the term "alkynyl" means a straight or branched alkyl group having one or more triple carbon-carbon bonds and 2-20 carbon atoms, including, but not limited to, acetylene, 1-propylene, 2-propylene, and the like. In some embodiments, the alkynyl chain is 2 to 10 carbon atoms in length, from 2 to 8 carbon atoms in length, from 2 to 6 carbon atoms in length, or from 2 to 4 carbon atoms in length.

As used herein, the term "amidino" means —C(=NH)NH₂.

As used herein, the term "amino" means —NH₂.

As used herein, the term "aminoalkoxy" means an alkoxy group substituted by an amino group. An example of an aminoalkoxy is —OCH₂CH₂NH₂.

As used herein, the term "aminoalkyl" means an alkyl group substituted by an amino group.

An example of an aminoalkyl is —CH₂CH₂NH₂.

As used herein, the term "aminosulfonyl" means —S(=O)₂NH₂.

As used herein, the term "aminoalkylthio" means an alkylthio group substituted by an amino group. An example of an aminoalkylthio is —SCH₂CH₂NH₂.

As used herein, the term "amphiphilic" means a three-dimensional structure having discrete hydrophobic and hydrophilic regions. An amphiphilic compound suitably has the presence of both hydrophobic and hydrophilic elements.

As used herein, the term "animal" includes, but is not limited to, humans and non-human vertebrates such as wild, domestic, and farm animals.

As used herein, the term "AP" means a lipid soluble version of vitamin C known as vitamin C palmitate or ascorbyl palmitate (AP), an ester of ascorbic acid (vitamin C) and palmitic acid (C16:0). Other non-limiting ester acids of vitamin C are known, for example, acetate, linoleate, stearate, oleate are inclusive as AP.

As used herein, the term "aryl" means a monocyclic, bicyclic, or polycyclic (e.g., having 2, 3 or 4 fused rings) aromatic hydrocarbons. In some embodiments, aryl groups have from 6 to 20 carbon atoms or from 6 to 10 carbon atoms. Examples of aryl groups include, but are not limited to, phenyl, naphthyl, anthracenyl, phenanthrenyl, indanyl, indenyl, tetrahydronaphthyl, and the like. Examples of aryl groups include, but are not limited to:

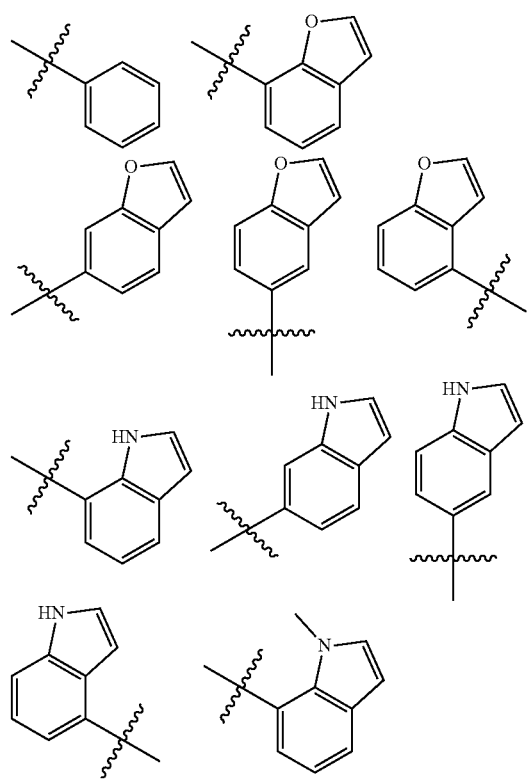

-continued
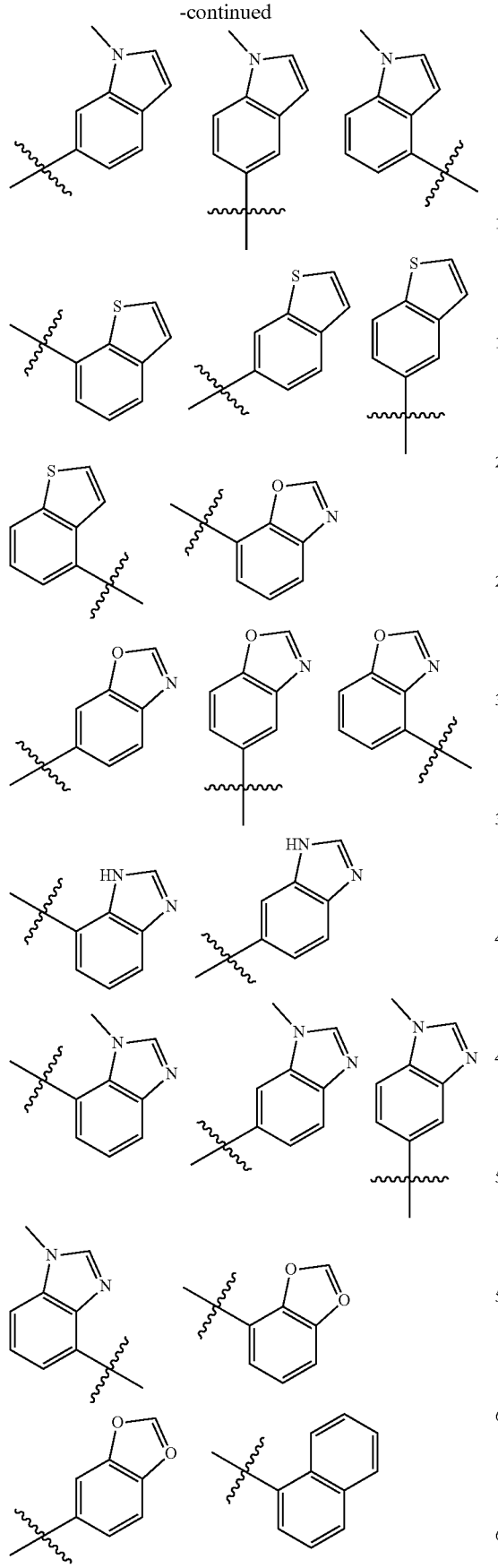
-continued
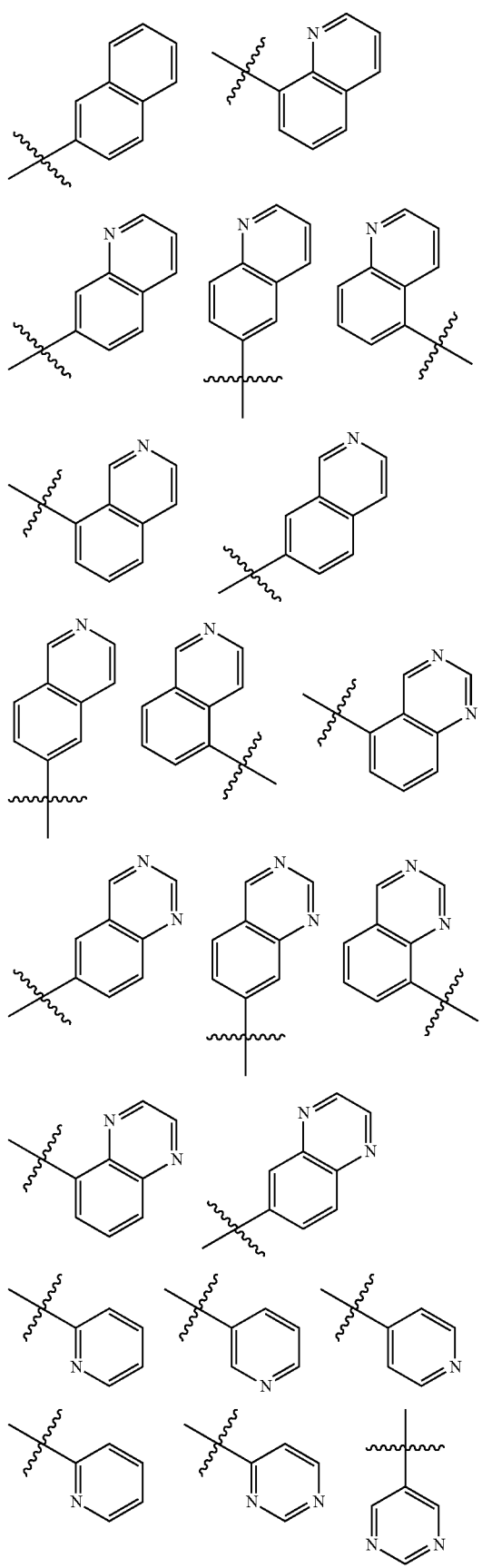

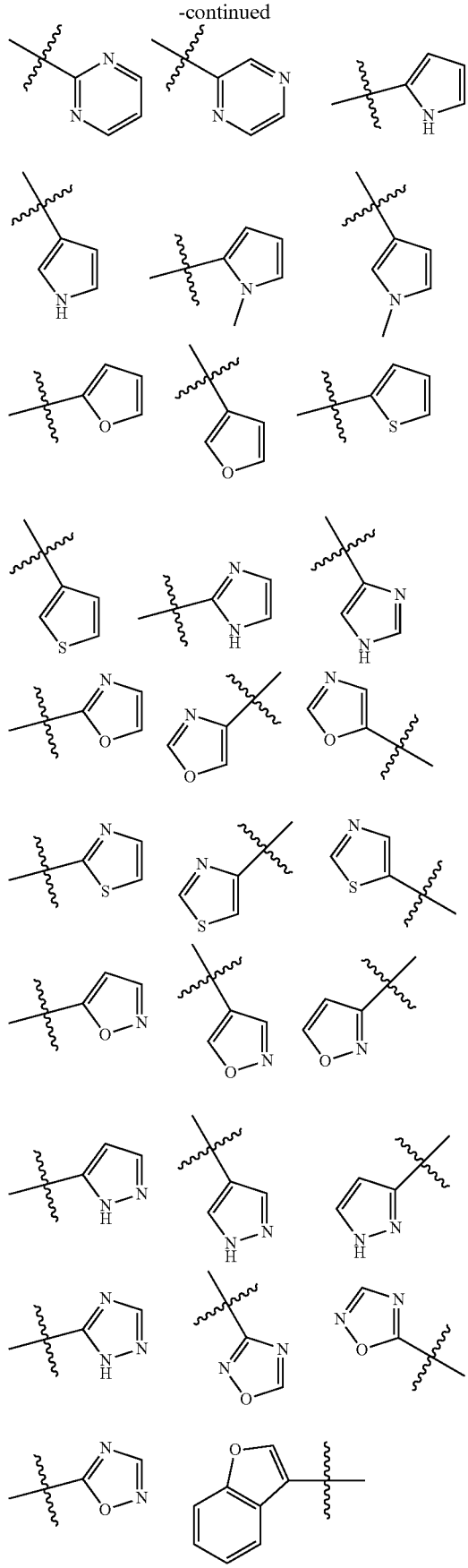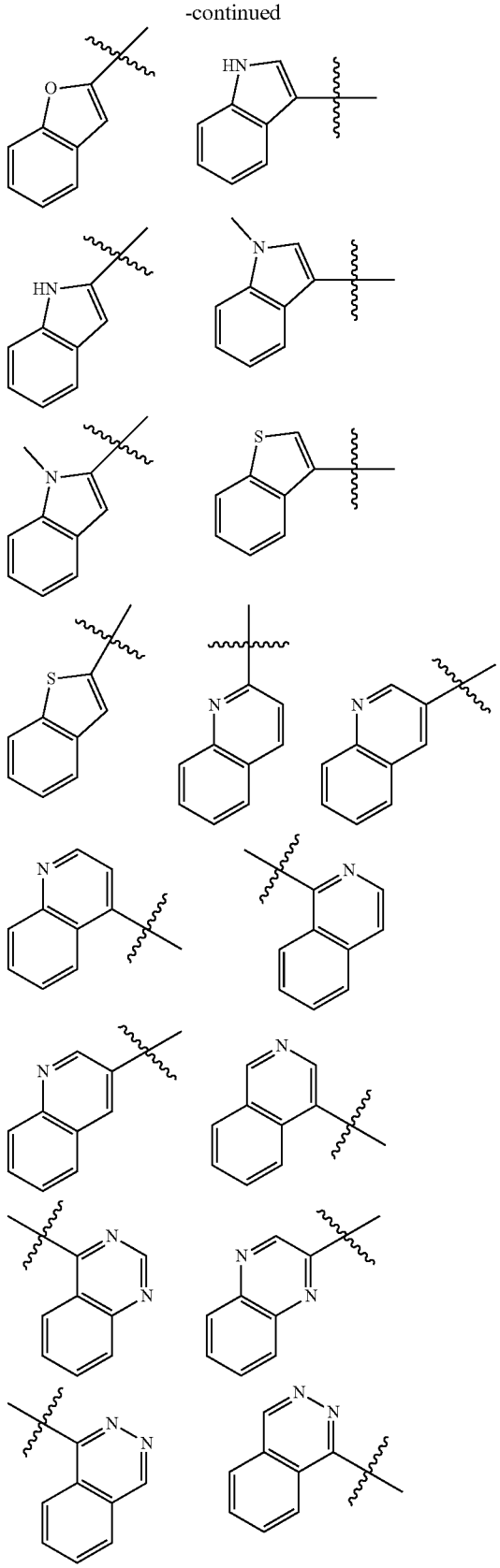
As used herein, the term "arylalkyl" means a $C_{1-6}$alkyl substituted by aryl.

As used herein, the term "arylamino" means an amino group substituted by an aryl group. An example of an arylamino is —NH(phenyl).

As used herein, the term "arylene" means an aryl linking group, i.e., an aryl group that links one group to another group in a molecule.

As used herein, the term "binary" means a mixture of two components, either CoQone plus AP, menaquinone(s) plus AP, or tocochromanones (tocopherones and/or tocotrienones) plus AP.

As used herein, the term "bioaccessiblity" means the fraction of the total amount of a substance that is potentially available for absorption. For example in nutrition and food, bioaccessiblity refers to the quantity of a compound that is released from its matrix in the gastrointestinal tract, becoming available for absorption (e.g. enters the blood stream).

As used herein, the term "bioavailability" means the proportion of a drug or other substance which enters the circulation when introduced into the body and so is able to have an active effect. In pharmacology, bioavailability refers to the fraction of an administered dose of unchanged drug that reaches the systemic circulation, one of the principal pharmacokinetic properties of drugs.

As used herein, the term "carbamoyl" means —C(=O)—NH$_2$.

As used herein, the term "carbocycle" means a 5- or 6-membered, saturated or unsaturated cyclic ring, optionally containing O, S, or N atoms as part of the ring. Examples of carbocycles include, but are not limited to, cyclopentyl, cyclohexyl, cyclopenta-1,3-diene, phenyl, and any of the heterocycles recited above.

As used herein, the term "carrier" means a diluent, adjuvant, or excipient with which a compound is administered. Pharmaceutical carriers can be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used.

As used herein, the term, "compound" means all stereoisomers, tautomers, and isotopes of the compounds described herein.

As used herein, the term "CoQ10" means a generic reference to CoQone (ubiquinone) and/or CoQnol (ubiquinol) and to their inseparable redox system.

As used herein, the term "curcuminoid" or "CC" means is a linear diarylheptanoid, with molecules such as curcumin or derivatives of curcumin.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "contacting" means bringing together of two compounds close enough in order to transfer one or more hydrogens from one compound to the other.

As used herein, the term "cyano" means —CN.

As used herein, the term "cycloalkyl" means non-aromatic cyclic hydrocarbons including cyclized alkyl, alkenyl, and alkynyl groups that contain up to 20 ring-forming carbon atoms. Cycloalkyl groups can include mono- or polycyclic ring systems such as fused ring systems, bridged ring systems, and spiro ring systems. In some embodiments, polycyclic ring systems include 2, 3, or 4 fused rings. A cycloalkyl group can contain from 3 to 15, from 3 to 10, from 3 to 8, from 3 to 6, from 4 to 6, from 3 to 5, or 5 or 6 ring-forming carbon atoms. Ring-forming carbon atoms of a cycloalkyl group can be optionally substituted by oxo or sulfido. Examples of cycloalkyl groups include, but are not limited to, cyclopropyl, cyclobutyl, cyclopentyl, cyclohexyl, cycloheptyl, cyclooctyl, cyclononyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (having a bond in common with) to the cycloalkyl ring, for example, benzo or thienyl derivatives of pentane, pentene, hexane, and the like (e.g., 2,3-dihydro-1H-inden-1-yl, or 1H-inden-2(3H)-one-1-yl).

As used herein, the term "cycloalkylalkyl" means a $C_{1-6}$alkyl substituted by cycloalkyl.

As used herein, the term "dialkylamino" means an amino group substituted by two alkyl groups, each having from 1 to 6 carbon atoms.

As used herein, the term "diazamino" means —N(NH$_2$)$_2$.

As used herein, the term "diterpenoids" means 20 carbon molecules having 4 isoprene units.

As used herein, the term "elevated temperature" means that reactions were conducted in temperatures from room temperatures (Room Temperature (RT)=24+/−4) C to a maximum of (100+/−10) C.

As used herein, the term "endogenous functions or benefits of GG" means the power of the diterpenoid GG to perform biological nutrient biosynthesis and replenishment of CoQ10, menaquinones, proteins, and testosterone, all of which provide essential and normal mammalian growth functions.

As used herein, the term "excipients" means chemical fillers that are exogenous, and they are mainly of synthetic origin.

As used herein, the term "facially amphiphilic" or "facial amphiphilicity" means compounds with polar (hydrophilic) and nonpolar (hydrophobic) side chains that adopt conformation(s) leading to segregation of polar and nonpolar side chains to opposite faces or separate regions of the structure or molecule.

As used herein, the term "GG" means geranylgeraniol, a diterpene alcohol.

As used herein, the term "glycerides" means molecules derived from fatty acids, e.g., monoglycerides (MG), diglycerides (DG), triglycerides (TG), phospholipids, lecithins, and compounds with one or more fatty acid adduct(s).

As used herein, the term "guanidino" means —NH(=NH)NH$_2$.

As used herein, the term "halo" means halogen groups including, but not limited to fluoro, chloro, bromo, and iodo.

As used herein, the term "haloalkoxy" means an —O-haloalkyl group. An example of a haloalkoxy group is OCF$_3$.

As used herein, the term "haloalkyl" means a $C_{1-6}$alkyl group having one or more halogen substituents. Examples of haloalkyl groups include, but are not limited to, CF$_3$, C$_2$F$_5$, CH$_2$F, CHF$_2$, CCl$_3$, CHCl$_2$, CH$_2$CF$_3$, and the like.

As used herein, the term "heteroaryl" means an aromatic heterocycle having up to 20 ring-forming atoms (e.g., C) and having at least one heteroatom ring member (ring-forming atom) such as sulfur, oxygen, or nitrogen. In some embodiments, the heteroaryl group has at least one or more heteroatom ring-forming atoms, each of which is, independently, sulfur, oxygen, or nitrogen. In some embodiments, the heteroaryl group has from 3 to 20 ring-forming atoms, from 3 to 10 ring-forming atoms, from 3 to 6 ring-forming atoms, or from 3 to 5 ring-forming atoms. In some embodiments, the heteroaryl group contains 2 to 14 carbon atoms, from 2 to 7 carbon atoms, or 5 or 6 carbon atoms. In some embodiments, the heteroaryl group has 1 to 4 heteroatoms, 1 to 3 heteroatoms, or 1 or 2 heteroatoms. Heteroaryl groups include monocyclic and polycyclic (e.g., having 2, 3 or 4 fused rings) systems. Examples of heteroaryl groups include, but are not limited to, pyridyl, pyrimidinyl, pyrazinyl, pyridazinyl, triazinyl, furyl, quinolyl, isoquinolyl, thienyl, imidazolyl, thiazolyl, indolyl (such as indol-3-yl), pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, pyranyl, oxadiazolyl, isoxazolyl, triazolyl, thianthrenyl, pyrazolyl, indolizinyl, isoindolyl, isobenzofuranyl, benzoxazolyl, xanthenyl, 2H-pyrrolyl, pyrrolyl, 3H-indolyl, 4H-quinolizinyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furanyl, phenoxazinyl groups, and the like. Suitable heteroaryl groups include 1,2,3-triazole, 1,2,4-triazole, 5-amino-1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, and 2-aminopyridine.

As used herein, the term "heteroarylalkyl" means a $C_{1-6}$alkyl group substituted by a heteroaryl group.

As used herein, the term "heteroarylamino" means an amino group substituted by a heteroaryl group. An example of a heteroarylamino is —NH-(2-pyridyl).

As used herein, the term "heteroarylene" means a heteroaryl linking group, i.e., a heteroaryl group that links one group to another group in a molecule.

As used herein, the term "heterocycle" or "heterocyclic ring" means a 5- to 7-membered mono- or bicyclic or 7- to 10-membered bicyclic heterocyclic ring system any ring of which may be saturated or unsaturated, and which consists of carbon atoms and from one to three heteroatoms chosen from N, O and S, and wherein the N and S heteroatoms may optionally be oxidized, and the N heteroatom may optionally be quaternized, and including any bicyclic group in which any of the above-defined heterocyclic rings is fused to a benzene ring. Particularly useful are rings containing one oxygen or sulfur, one to three nitrogen atoms, or one oxygen or sulfur combined with one or two nitrogen atoms. The heterocyclic ring may be attached at any heteroatom or carbon atom, which results in the creation of a stable structure. Examples of heterocyclic groups include, but are not limited to, piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

As used herein, the term "heterocycloalkyl" means non-aromatic heterocycles having up to 20 ring-forming atoms including cyclized alkyl, alkenyl, and alkynyl groups, where one or more of the ring-forming carbon atoms is replaced by a heteroatom such as an O, N, or S atom. Heterocycloalkyl groups can be mono or polycyclic (e.g., fused, bridged, or spiro systems). In some embodiments, the heterocycloalkyl group has from 1 to 20 carbon atoms or from 3 to 20 carbon atoms. In some embodiments, the heterocycloalkyl group contains 3 to 14 ring-forming atoms, 3 to 7 ring-forming atoms, or 5 or 6 ring-forming atoms. In some embodiments, the heterocycloalkyl group has 1 to 4 heteroatoms, 1 to 3 heteroatoms, or 1 or 2 heteroatoms. In some embodiments, the heterocycloalkyl group contains 0 to 3 double bonds. In some embodiments, the heterocycloalkyl group contains 0 to 2 triple bonds. Examples of heterocycloalkyl groups include, but are not limited to, morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, oxazolidinyl, isothiazolidinyl, pyrazolidinyl, thiazolidinyl, imidazolidinyl, pyrrolidin-2-one-3-yl, and the like. In addition, ring-forming carbon atoms and heteroatoms of a heterocycloalkyl group can be optionally substituted by oxo or sulfido. For example, a ring-forming S atom can be substituted by 1 or 2 oxo (form a S(O) or $S(O)_2$). For another example, a ring-forming C atom can be substituted by oxo (form carbonyl). Also included in the definition of heterocycloalkyl are moieties that have one or more aromatic rings fused (having a bond in common with) to the nonaromatic heterocyclic ring including, but not limited to, pyridinyl, thiophenyl, phthalimidyl, naphthalimidyl, and benzo derivatives of heterocycles such as indolene, isoindolene, 4,5,6,7-tetrahydrothieno[2,3-c]pyridine-5-yl, 5,6-dihydrothieno[2,3-c]pyridin-7(4H)-one-5-yl, isoindolin-1-one-3-yl, and 3,4-dihydroisoquinolin-1(2H)-one-3yl groups. Ring-forming carbon atoms and heteroatoms of the heterocycloalkyl group can be optionally substituted by oxo or sulfido.

As used herein, the term "heterocycloalkylalkyl" refers to a $C_{1-6}$ alkyl substituted by heterocycloalkyl.

As used herein, the term "hydroxy" or "hydroxyl" means an —OH group.

As used herein, the term "hydroxyalkyl" or "hydroxylalkyl" means an alkyl group substituted by a hydroxyl group. Examples of a hydroxylalkyl include, but are not limited to, —CH₂OH and —CH₂CH₂OH.

As used herein, the term "individual" or "patient," used interchangeably, means any animal or pet including mammals, such as mice, rats, other rodents, rabbits, dogs, cats, swine, cattle, sheep, horses, or primates, such as humans.

As used herein, the term "in need thereof" means that the animal or mammal has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent. In some embodiments, the subject that has been identified as in need thereof, is a subject who is being treated with a statin.

As used herein, the term "inert" or "inert environment" means that a reaction environment where there is absent of air, oxygen or otherwise in a non-aerobic or anaerobic condition.

As used herein, the term "in situ gellable" means embracing not only liquids of low viscosity that form gels upon contact with the eye or with lacrimal fluid in the exterior of the eye, but also more viscous liquids such as semi-fluid and thixotropic gels that exhibit substantially increased viscosity or gel stiffness upon administration to the eye.

As used herein, the term "integer from X to Y" means any integer that includes the endpoints. For example, the term "integer from X to Y" means 1, 2, 3, 4, or 5.

As used herein, the term "isoprene" or "2-methyl-1,3-butadiene" means a common organic compound with the formula $CH_2=C(CH_3)—CH=CH_2$. CoQone and CoQnol have 10 isoprene units in each of their side-chains, hence the common designation of CoQ10. Sesquiterpene alcohol ("T3") and GG have 3 and 4 isoprene units in their side-chains, respectively. For example, among the menaquinone series, MK4 and MK7 have 4 and 7 isoprene units, respectively.

As used herein, the term "lipid quinone nutrients" means lipid nutrients in the oxidized state (ubiquinones, menaquinones, and vitamin E tocopherones and tocotrienones).

As used herein, the term "lipid quinol nutrients" means lipid nutrients in the reduced state (ubiquinols, menaquinols, and vitamin E tocopherols and tocotrienols).

As used herein, the term "mammal" means a rodent (i.e., a mouse, a rat, or a guinea pig), a monkey, a cat, a dog, a cow, a horse, a pig, or a human. In some embodiments, the mammal is a human.

As used herein, the term "menaquinones" or "vitamin $K_2$," means a series of MK2 to MK13 quinone products, all of which are part of vitamin $K_2$. For example, "MK4one" means vitamin MK4 and "MK4nol" means the reduced form of vitamin MK4; "MK7one" means vitamin MK4 and "MK7nol" means the reduced form of vitamin MK7.

As used herein, the term "N-alkyl" refers to an alkyl chain that is substituted with an amine group. Non-limiting examples include, but are not limited to

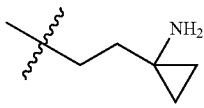

and the like. The alkyl chain can be linear, branched, cyclic, or any combination thereof. In some embodiments, the alkyl comprises 1-10, 1-9, 1-8, 1-7, 1-6, 1-5, 1-4, 1-3, or 1-2 carbons.

As used herein, the term "monoterpenoids" mean 10 carbon molecules having 2 isoprene units.

As used herein, the term "n-membered", where n is an integer, typically describes the number of ring-forming atoms in a moiety, where the number of ring-forming atoms is n. For example, pyridine is an example of a 6-membered heteroaryl ring and thiophene is an example of a 5-membered heteroaryl ring.

As used herein, the term "noble gases," "inert gas," or "neutral, non-oxygenated" means a number of inert gases with increasing densities (helium, neon, argon, krypton, xenon) for which argon, krypton, and xenon are heavier than air. Nitrogen, a near-inert gas, is included in this list.

As used herein, the term "ophthalmically acceptable" means having no persistent detrimental effect on the treated eye or the functioning thereof, or on the general health of the subject being treated. However, it will be recognized that transient effects such as minor irritation or a "stinging" sensation are common with topical ophthalmic administration of drugs and the existence of such transient effects is not inconsistent with the composition, formulation, or ingredient (e.g., excipient) in question being "ophthalmically acceptable" as herein defined.

As used herein, the term "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent groups, provided that the normal valency of the designated atom or moiety is not exceeded, and that the substitution results in a stable compound. For example, if a methyl group is optionally substituted, then 3 hydrogen atoms on the carbon atom can be replaced with substituent groups.

As used herein, the term "pharmaceutically acceptable" means those compounds, materials, compositions, and/or dosage forms which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia for use in animals, and more particularly in humans.

In some embodiments, the salt of a compound described herein is a pharmaceutically acceptable salt. As used herein, the term "pharmaceutically acceptable salt(s)," includes, but is not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, maleic, acetic, oxalic, hydrochloride, hydrobromide, hydroiodide, nitrate, sulfate, bisulfate, bisulfite, phosphate, acid phosphate, isonicotinate, borate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, bicarbonate, malonate, mesylate, esylate, napsydisylate, tosylate, besylate, orthophoshate, trifluoroacetate, and pamoate (i.e., 1,1'-methylene-bis-(2-hydroxy-3-naphthoate)) salts. Compounds that include an amino moiety may form pharmaceutically acceptable salts, solvates or prodrugs with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron salts. The present embodiments also includes quaternary ammonium salts of the compounds described herein, where the compounds have one or more tertiary amine moiety.

As used herein, the term "phenyl" means $—C_6H_5$. A phenyl group can be unsubstituted or substituted with one, two, or three suitable substituents.

As used herein, the term "phylloquinone" means a series of saturated side-chained quinone products, all of which are part of vitamin K1.

As used herein, the term "physical functions or benefits of GG" means that the power of diterpenoid GG to solubilize and dissolve reactants, depress MP of reactants so as to provide intimate molecular contact of oxidants and reductants.

As used herein, the term "polyols" means polyhydroxy solvents, e.g., glycerol, propylene glycol.

As used herein, the term "prodrug" means a derivative of a known direct acting drug, which derivative has enhanced delivery characteristics and therapeutic value as compared to the drug, and is transformed into the active drug by an enzymatic or chemical process.

As used herein, the term "purified" means that when isolated, the isolate contains at least 90%, at least 95%, at least 98%, or at least 99% of a compound described herein by weight of the isolate.

As used herein, the term "PQQ" or "PQQone" means pyrroloquinoline quinone (PQQ), also called methoxatin. The reduced form of PQQ is PQQnol.

As used herein, the term "quaternary ammonium salts" means derivatives of the disclosed compounds with one or more tertiary amine moieties wherein at least one of the tertiary amine moieties in the parent compound is modified by converting the tertiary amine moiety to a quaternary ammonium cation via alkylation (and the cations are balanced by anions such as $Cl^-$, $CH_3COO^-$, and $CF_3COO^-$), for example methylation or ethylation.

As used herein, the term "quinone" means a class of organic compounds that are formally derived from aromatic compounds such as benzene or naphthalene by conversion of an even number of —CH= groups into —C(=O)— groups with any necessary rearrangement of double bonds, resulting in a fully conjugated cyclic dione structure. The class includes some heterocyclic compounds. For examples, quinone can be ubiquinone, vitamin E quinone, vitamin K quinone, or pyrroloquinoline quinone, or a combination thereof. "Vitamin K quinone" means a member of vitamin family, such as but not limited to vitamin K1, vitamin MK-4 or vitamin MK-7, or a combination thereof. "Vitamin E quinone" means an oxidized form of a member of vitamin E family such as but not limited to a tocopherol quinone, or a tocotrienol quinone, or a combination thereof.

As used herein, the term "quinol," means a class of organic compounds that are derived from "quinone" such as a reduced form of quinone as described herein. For examples, quinol can be ubiquinol, vitamin E quinol, vitamin K quinol, or pyrroloquinoline quinol, or a combination thereof. "Vitamin E quinol" means a member of vitamin family, such as but not limited to a tocopherol, or a tocotrienol, or a combination thereof. "Vitamin K quinol" means a quinol derived from reduction of a member of vitamin K family such as but not limited to vitamin K1, vitamin MK-4, or vitamin MK-7, or a combination thereof.

As used herein, the term "quinone oxidants" means di-ketones that are part of a ringed redox system that prepare to gain two hydrogens or electrons including mono-ketones.

As used herein, the term "quinol reductants" means di-alcohols that are part of a ringed redox system that prepare to lose two hydrogens or electrons including mono-alcohols.

As used herein, the term "semicarbazone" means =NNHC(=O)NH$_2$.

As used herein, the term "solubilization and dissolution—A substance or nutrient is considered truly dissolved when the solution is homogenized and miscible.

As used herein, the term "solubilizing agent" means agents that result in formation of a micellar solution or a true solution of the drug.

As used herein, the term "solution/suspension" means a liquid composition wherein a first portion of the active agent is present in solution and a second portion of the active agent is present in particulate form, in suspension in a liquid matrix.

As used herein, the term "substantially isolated" means a compound that is at least partially or substantially separated from the environment in which it is formed or detected.

As used herein, the terms "suitable substituent" or "substituent" mean a group that does not nullify the synthetic or pharmaceutical utility of the compounds described herein or the intermediates useful for preparing them. Examples of suitable substituents include, but are not limited to: $C_1$-$C_6$alkyl, $C_1$-$C_6$alkenyl, $C_1$-$C_6$alkynyl, $C_5$-$C_6$aryl, $C_1$-$C_6$alkoxy, $C_3$-$C_5$heteroaryl, $C_3$-$C_6$cycloalkyl, $C_5$-$C_6$aryloxy, —CN, —OH, oxo, halo, haloalkyl, —NO$_2$, —CO$_2$H, —NH$_2$, —NH($C_1$-$C_8$alkyl), —N($C_1$-$C_8$alkyl)$_2$, —NH($C_6$aryl), —N($C_5$-$C_6$aryl)$_2$, —CHO, —CO($C_1$-$C_6$alkyl), —CO(($C_5$-$C_6$)aryl), —CO$_2$(($C_1$-$C_6$)alkyl), and —CO$_2$(($C_5$-$C_6$)aryl). One of skill in art can readily choose a suitable substituent based on the stability and pharmacological and synthetic activity of the compounds described herein.

As used herein, the term "suspension" means that a partially solubilized CoQ10 in solvent(s) or mixtures where the CoQ10 is dispersed, emulsified and the solution is heterogeneous and further that the solution is not miscible.

As used herein, the term "surfactants and emulsifiers" means synthetic chemicals (polysorbates, complex esters, ester-ethers) that help to disperse solutes in a solvent.

As used herein, the term "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment.

As used herein, the term "THC" means tetrahydorcurcumin.

As used herein, the terms "treat," "treated," or "treating" mean both therapeutic treatment and prophylactic measures wherein the object is to slow down (lessen) an undesired physiological condition, disorder or disease, or obtain beneficial or desired clinical results. Beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response without excessive levels of side effects. Treatment also includes prolonging survival as compared to expected survival if not receiving treatment. Thus, "treatment of erythropoietic protoporphyria" or "treating erythropoietic protoporphyria" means an activity that alleviates or ameliorates any of the primary phenomena or secondary symptoms associated with the erythropoietic protoporphyria or other condition described herein.

As used herein, the term "ureido" means —NHC(=O)—NH$_2$.

As used herein, the term "Vitamin E" means tocochromanols (a form of terpenoid alcohols) that include tocopherols (having saturated side-chains) and tocotrienols (have unsaturated 3-isoprene side-chains).

At various places in the present specification, substituents of compounds may be disclosed in groups or in ranges. It is specifically intended that embodiments include each and every individual subcombination of the members of such groups and ranges. For example, the term "$C_{1-6}$alkyl" is specifically intended to individually disclose methyl, ethyl, propyl, $C_4$alkyl, $C_5$alkyl, and $C_6$alkyl.

For compounds in which a variable appears more than once, each variable can be a different moiety selected from the Markush group defining the variable. For example, where a structure is described having two R groups that are simultaneously present on the same compound, the two R groups can represent different moieties selected from the Markush groups defined for R. In another example, when an optionally multiple substituent is designated in the form, for example,

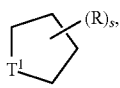

then it is understood that substituent R can occur s number of times on the ring, and R can be a different moiety at each occurrence. In the above example, where the variable $T^1$ is defined to include hydrogens, such as when $T^1$ is CH$_2$, NH, etc., any H can be replaced with a substituent.

It is further appreciated that certain features described herein, which are, for clarity, described in the context of separate embodiments, can also be provided in combination in a single embodiment. Conversely, various features, which are, for brevity, described in the context of a single embodiment, can also be provided separately or in any suitable subcombination.

It is understood that the present embodiments encompasses the use, where applicable, of stereoisomers, diastereomers and optical stereoisomers of the compounds, as well as mixtures thereof. Additionally, it is understood that stereoisomers, diastereomers, and optical stereoisomers of the compounds, and mixtures thereof, are within the scope of the embodiments. By way of non-limiting example, the mixture may be a racemate or the mixture may comprise unequal proportions of one particular stereoisomer over the other. Additionally, the compounds can be provided as a substantially pure stereoisomers, diastereomers and optical stereoisomers (such as epimers).

The compounds described herein can be asymmetric (e.g., having one or more stereocenters). All stereoisomers, such as enantiomers and diastereomers, are intended to be included within the scope of the embodiments unless otherwise indicated. Compounds that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are provided herein. Cis and trans geometric isomers of the compounds are also included within the present embodiments and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

In some embodiments, the composition comprises a compound, or a pharmaceutically acceptable salt, solvate or prodrug thereof, that is at least 90%, at least 95%, at least 98%, or at least 99%, or 100% enantiomeric pure, which means that the ratio of one enantiomer to the other in the composition is at least 90:1 at least 95:1, at least 98:1, or at least 99:1, or is completely in the form of one enantiomer over the other.

Resolution of racemic mixtures of compounds can be carried out by any of numerous methods known in the art, including, for example, chiral HPLC, fractional recrystallization using a chiral resolving acid, which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as (3-camphorsulfonic acid. Other resolving agents suitable for fractional crystallization methods include, but are not limited to, stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Compounds may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds also include hydrates and solvates, as well as anhydrous and non-solvated forms.

Compounds can also include all isotopes of atoms occurring in the intermediates or final compounds. Isotopes include those atoms having the same atomic number but different mass numbers. For example, isotopes of hydrogen include tritium and deuterium.

In some embodiments, the compounds, or salts thereof, are substantially isolated. Partial separation can include, for example, a composition enriched in the compound. Substantial separation can include compositions containing at least about 50%, at least about 60%, at least about 70%, at least about 80%, at least about 90%, at least about 95%, at least about 97%, or at least about 99% by weight of the compound, or salt thereof. Methods for isolating compounds and their salts are routine in the art.

Although the disclosed compounds are suitable, other functional groups can be incorporated into the compound with an expectation of similar results. In particular, thioamides and thioesters are anticipated to have very similar properties. The distance between aromatic rings can impact the geometrical pattern of the compound and this distance can be altered by incorporating aliphatic chains of varying length, which can be optionally substituted or can comprise an amino acid, a dicarboxylic acid or a diamine. The distance between and the relative orientation of monomers within the compounds can also be altered by replacing the amide bond with a surrogate having additional atoms. Thus, replacing a carbonyl group with a dicarbonyl alters the distance between the monomers and the propensity of dicarbonyl unit to adopt an anti-arrangement of the two carbonyl moiety and alter the periodicity of the compound. Pyromellitic anhydride represents still another alternative to simple amide linkages, which can alter the conformation and physical properties of the compound. Modern methods of solid phase organic chemistry (E. Atherton and R. C. Sheppard, Solid Phase Peptide Synthesis A Practical Approach IRL Press Oxford 1989) now allow the synthesis of homodisperse compounds with molecular weights approaching 5,000 Daltons. Other substitution patterns are equally effective.

The compounds also include derivatives referred to as prodrugs.

Compounds containing an amine function can also form N-oxides. A reference herein to a compound that contains an amine function also includes the N-oxide. Where a compound contains several amine functions, one or more than one nitrogen atom can be oxidized to form an N-oxide. Examples of N-oxides include N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g., a peroxycarboxylic acid) (see, Advanced Organic Chemistry, by Jerry March, 4th Edition, Wiley Interscience).

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, analogs, compounds, ligands, structures, or groups thereof, or any members of a claimed group, less than the full measure of this disclosure can be claimed for any reason. Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

Embodiments of compositions comprising various compounds and salts thereof are provided. Where a variable is not specifically recited, the variable can be any option described herein, except as otherwise noted or dictated by context.

In some embodiments, the compound is as described in the appended exemplary compositions, non-limiting claims, or a pharmaceutically acceptable salt, solvate or prodrug thereof.

In some embodiments, a composition comprising one or more compound, or salts thereof, such as pharmaceutically acceptable salts, solvates or prodrugs thereof, which are chosen from compounds of as described herein. Any of the compounds provided for herein can be prepared as salts or pharmaceutically acceptable salts, solvates or prodrugs and/ or as part of a pharmaceutical composition as described in the cited patents or patent application publications herein.

Although the compounds described herein may be shown with specific stereochemistries around certain atoms, such as cis or trans, the compounds can also be made in the opposite orientation or in a racemic mixture. Such isomers or racemic mixtures are encompassed by the present disclosure. Additionally, although the compounds are shown collectively in a table, any compounds, or a pharmaceutically acceptable salt, solvate or prodrug thereof, can be chosen from the table and used in the embodiments provided for herein.

The compositions described herein can be made according to the methods described in the cited patents or patent application publications herein.

The compositions described herein can be administered in any conventional manner by any route where they are active. Administration can be systemic, topical, or oral. For example, administration can be, but is not limited to, parenteral, subcutaneous, intravenous, intramuscular, intraperitoneal, transdermal, oral, buccal, sublingual, or ocular routes, or intravaginal, by inhalation, by depot injections, or by implants. The mode of administration can depend on the conditions or disease to be targeted or treated. The selection of the specific route of administration can be selected or adjusted by the clinician according to methods known to the clinician to obtain the desired clinical response.

In some embodiments, it may be desirable to administer compositions comprising one or more compound, or pharmaceutically acceptable salts, solvates or prodrugs thereof, locally to an area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, wherein the implant is of a porous, non-porous, or gelatinous material, including membranes, such as sialastic membranes, or fibers.

The compositions described herein can be administered either alone or in combination (concurrently or serially) with other pharmaceuticals. Examples of other pharmaceuticals or medicaments are known to one of skill in the art and include, but are not limited to those described herein.

The means and methods for administration are known in the art and an artisan can refer to various pharmacologic references for guidance (see, for example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980)).

The amount of composition to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). The standard dosing for protamine can be used and adjusted (i.e., increased or decreased) depending upon the factors described above. The selection of the specific dose regimen can be selected or adjusted or titrated by the clinician according to methods known to the clinician to obtain the desired clinical response.

The amount of compositions described herein that will be effective in the treatment and/or prevention of a particular disease, condition, or disorder will depend on the nature and extent of the disease, condition, or disorder, and can be determined by standard clinical techniques. In addition, in vitro or in vivo assays may optionally be employed to help identify optimal dosage ranges. The precise dose to be employed in the compositions will also depend on the route of administration, and the seriousness of the disorder, and should be decided according to the judgment of the practitioner and each patient's circumstances. However, a suitable dosage range for oral administration is, generally, from about 0.001 milligram to about 200 milligrams per kilogram body weight, from about 0.01 milligram to about 100 milligrams per kilogram body weight, from about 0.01 milligram to about 70 milligrams per kilogram body weight, from about 0.1 milligram to about 50 milligrams per kilogram body weight, from 0.5 milligram to about 20 milligrams per kilogram body weight, or from about 1 milligram to about 10 milligrams per kilogram body weight. In some embodiments, the oral dose is about 5 milligrams per kilogram body weight.

In some embodiments, suitable dosage ranges for intravenous (i.v.) administration are from about 0.01 mg to about 500 mg per kg body weight, from about 0.1 mg to about 100 mg per kg body weight, from about 1 mg to about 50 mg per kg body weight, or from about 10 mg to about 35 mg per kg body weight. Suitable dosage ranges for other modes of administration can be calculated based on the forgoing dosages as known by those skilled in the art. For example, recommended dosages for intranasal, transmucosal, intradermal, intramuscular, intraperitoneal, subcutaneous, epidural, sublingual, intracerebral, intravaginal, transdermal administration or administration by inhalation are in the range of from about 0.001 mg to about 200 mg per kg of body weight, from about 0.01 mg to about 100 mg per kg of body weight, from about 0.1 mg to about 50 mg per kg of body weight, or from about 1 mg to about 20 mg per kg of body weight. Effective doses may be extrapolated from dose-response curves derived from in vitro or animal model test systems. Such animal models and systems are well known in the art.

The compositions described herein can be formulated for parenteral administration by injection, such as by bolus injection or continuous infusion. The compositions can be administered by continuous infusion subcutaneously over a period of about 15 minutes to about 24 hours. Formulations for injection can be presented in unit dosage form, such as in ampoules or in multi-dose containers, with an optionally added preservative. The compositions can take such forms as suspensions, solutions or emulsions in oily or aqueous vehicles, and can contain formulatory agents such as suspending, stabilizing and/or dispersing agents. In some embodiments, the injectable is in the form of short-acting, depot, or implant and pellet forms injected subcutaneously or intramuscularly. In some embodiments, the parenteral dosage form is the form of a solution, suspension, emulsion, or dry powder.

For oral administration, the compositions described herein can be formulated by combining the compounds with pharmaceutically acceptable carriers well known in the art. Such carriers enable the compounds to be formulated as tablets, pills, dragees, capsules, emulsions, liquids, gels (e.g. softgels), syrups, caches, pellets, powders, granules, slurries, lozenges, aqueous or oily suspensions, and the like, for oral ingestion by a patient to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period. Selectively permeable membranes surrounding an osmotically active driving compound are also suitable for orally administered compounds. Oral compositions can include standard vehicles such as mannitol, lactose, starch, magnesium stearate, sodium saccharine, cellulose, magnesium carbonate, etc. Such vehicles are suitably of pharmaceutical grade.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations, which can be used orally, include, but are not limited to, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

For buccal administration, the compositions can take the form of, such as, tablets or lozenges formulated in a conventional manner.

For administration by inhalation, the compositions described herein can be delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, such as gelatin for use in an inhaler or insufflator can be formulated containing a powder mix of the compound and a suitable powder base such as lactose or starch.

The compositions described herein can also be formulated in rectal compositions such as suppositories or retention enemas, such as containing conventional suppository bases such as cocoa butter or other glycerides. The compositions described herein can also be formulated in vaginal compositions such as vaginal creams, suppositories, pessaries, vaginal rings, and intrauterine devices.

In transdermal administration, the compositions can be applied to a plaster, or can be applied by transdermal, therapeutic systems that are consequently supplied to the organism. In some embodiments, the compositions are present in creams, solutions, powders, fluid emulsions, fluid suspensions, semi-solids, ointments, pastes, gels, jellies, and foams, or in patches containing any of the same.

The compositions described herein can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compositions can be formulated with suitable polymeric or hydrophobic materials (for example as an emulsion in an acceptable oil) or ion exchange resins, or as sparingly soluble derivatives, for example, as a sparingly soluble salt.

In some embodiments, the compositions can be delivered in a controlled release system. In one embodiment, a pump may be used (see Langer, supra; Sefton, CRC Crit. Ref. Biomed. Eng., 1987, 14, 201; Buchwald et al., Surgery, 1980, 88, 507 Saudek et al., N. Engl. J. Med., 1989, 321, 574). In some embodiments, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger et al., J. Macromol. Sci. Rev. Macromol. Chem., 1983, 23, 61; see, also Levy et al., Science, 1985, 228, 190; During et al., Ann. Neurol., 1989, 25, 351; Howard et al., J. Neurosurg., 1989, 71, 105). In yet another embodiment, a controlled-release system can be placed in proximity of the target of the compositions described herein, such as the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, Science, 1990, 249, 1527-1533) may be used.

It is also known in the art that the compositions can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols. In some embodiments, the compositions described herein can be used with agents including, but not limited to, topical analgesics (e.g., lidocaine), barrier devices (e.g., GelClair), or rinses (e.g., Caphosol).

In some embodiments, the compositions described herein can be delivered in a vesicle, in particular a liposome (see, Langer, Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

Suitable compositions include, but are not limited to, oral non-absorbed compositions. Suitable compositions also include, but are not limited to saline, water, cyclodextrin solutions, and buffered solutions of pH 3-9.

The compositions described herein, or pharmaceutically acceptable salts, solvates or prodrugs thereof, can be formulated with numerous excipients including, but not limited to, purified water, propylene glycol, PEG 400, glycerin, DMA, ethanol, benzyl alcohol, citric acid/sodium citrate (pH3), citric acid/sodium citrate (pH5), tris(hydroxymethyl) amino methane HCl (pH7.0), 0.9% saline, and 1.2% saline, and any combination thereof. In some embodiments, excipient is chosen from propylene glycol, purified water, and glycerin.

In some embodiments, the formulation can be lyophilized to a solid and reconstituted with, for example, water prior to use.

When administered to a mammal (e.g., to an animal for veterinary use or to a human for clinical use) the compositions can be administered in isolated form.

When administered to a human, the compositions can be sterile. Water is a suitable carrier when the compound of Formula I-VII is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can take the form of a solution, suspension, emulsion, tablet, pill, pellet, capsule, capsule containing a liquid, powder, sustained-release formulation, suppository, aerosol, spray, or any other form suitable for use. Examples of suitable pharmaceutical carriers are described in Remington's Pharmaceutical Sciences, A. R. Gennaro (Editor) Mack Publishing Co.

In some embodiments, the compositions are formulated in accordance with routine procedures as a pharmaceutical composition adapted for administration to humans Typically, compositions are solutions in sterile isotonic aqueous buffer. Where necessary, the compositions can also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound is to be administered by infusion, it can be dispensed, for example, with an infusion bottle containing sterile pharmaceutical grade water or saline. Where the compound is administered by injection, an ampoule of sterile water for injection or saline can be provided so that the ingredients may be mixed prior to administration.

The pharmaceutical compositions can be in unit dosage form. In such form, the composition can be divided into unit doses containing appropriate quantities of the active component. The unit dosage form can be a packaged preparation, the package containing discrete quantities of the preparations, for example, packeted tablets, capsules, and powders in vials or ampules. The unit dosage form can also be a capsule, cachet, or tablet itself, or it can be the appropriate number of any of these packaged forms.

In some embodiments, a composition is in the form of a liquid wherein the active agent (i.e., one of the facially amphiphilic polymers or oligomers disclosed herein) is present in solution, in suspension, as an emulsion, or as a solution/suspension. In some embodiments, the liquid composition is in the form of a gel. In other embodiments, the liquid composition is aqueous. In other embodiments, the composition is in the form of an ointment.

In some embodiments, the composition is in the form of a solid article. For example, in some embodiments, the ophthalmic composition is a solid article that can be inserted in a suitable location in the eye, such as between the eye and eyelid or in the conjunctival sac, where it releases the active agent as described, for example, U.S. Pat. Nos. 3,863,633; 3,867,519; 3,868,445; 3,960,150; 3,963,025; 4,186,184; 4,303,637; 5,443,505; and 5,869,079. Release from such an article is usually to the cornea, either via the lacrimal fluid that bathes the surface of the cornea, or directly to the cornea itself, with which the solid article is generally in intimate contact. Solid articles suitable for implantation in the eye in such fashion are generally composed primarily of polymers and can be bioerodible or non-bioerodible. Bioerodible polymers that can be used in the preparation of ocular implants carrying one or more of compositions include, but are not limited to, aliphatic polyesters such as polymers and copolymers of poly(glycolide), poly(lactide), poly(epsilon-caprolactone), poly-(hydroxybutyrate) and poly(hydroxyvalerate), polyamino acids, polyorthoesters, polyanhydrides, aliphatic polycarbonates and polyether lactones. Suitable non-bioerodible polymers include silicone elastomers.

The compositions described herein can contain preservatives. Suitable preservatives include, but are not limited to, mercury-containing substances such as phenylmercuric salts (e.g., phenylmercuric acetate, borate and nitrate) and thimerosal; stabilized chlorine dioxide; quaternary ammonium compositions such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

Optionally one or more stabilizers can be included in the compositions to enhance chemical stability where required. Suitable stabilizers include, but are not limited to, chelating agents or complexing agents, such as, for example, the calcium complexing agent ethylene diamine tetraacetic acid (EDTA). For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%. In those embodiments containing a preservative other than EDTA, the EDTA or a salt thereof, more particularly disodium EDTA, can be present in an amount of about 0.025% to about 0.1% by weight.

One or more antioxidants can also be included in the compositions. Suitable antioxidants include, but are not limited to, ascorbic acid, sodium metabisulfite, sodium bisulfite, acetylcysteine, polyquaternium-1, benzalkonium chloride, thimerosal, chlorobutanol, methyl paraben, propyl paraben, phenylethyl alcohol, edetate disodium, sorbic acid, or other agents know to those of skill in the art. Such preservatives are typically employed at a level of from about 0.001% to about 1.0% by weight.

In some embodiments, the compositions are solubilized at least in part by an acceptable solubilizing agent. Certain acceptable nonionic surfactants, for example polysorbate 80, can be useful as solubilizing agents, as can ophthalmically acceptable glycols, polyglycols, e.g., polyethylene glycol 400 (PEG-400), and glycol ethers.

Suitable solubilizing agents for solution and solution/suspension compositions are cyclodextrins. Suitable cyclodextrins can be chosen from α-cyclodextrin, O-cyclodextrin, γ-cyclodextrin, alkylcyclodextrins (e.g., methyl-β-cyclodextrin, dimethyl-β-cyclodextrin, diethyl-β-cyclodextrin), hydroxyalkylcyclodextrins (e.g., hydroxyethyl-β-cyclodextrin, hydroxypropyl-β-cyclodextrin), carboxy-alkylcyclodextrins (e.g., carboxymethyl-β-cyclodextrin), sulfoalkylether cyclodextrins (e.g., sulfobutylether-β-cyclodextrin), and the like. Ophthalmic applications of cyclodextrins have been reviewed in Rajewski et al., Journal of Pharmaceutical Sciences, 1996, 85, 1155-1159.

In some embodiments, the composition optionally contains a suspending agent. For example, in those embodiments in which the composition is an aqueous suspension or solution/suspension, the composition can contain one or more polymers as suspending agents. Useful polymers include, but are not limited to, water-soluble polymers such as cellulosic polymers, for example, hydroxypropyl methylcellulose, and water-insoluble polymers such as cross-linked carboxyl-containing polymers.

One or more acceptable pH adjusting agents and/or buffering agents can be included in the compositions, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

One or more acceptable salts, solvates or prodrugs can be included in the compositions in an amount required to bring osmolality of the composition into an acceptable range. Such salts include, but are not limited to, those having sodium, potassium or ammonium cations and chloride, citrate, ascorbate, borate, phosphate, bicarbonate, sulfate, thiosulfate or bisulfite anions. In some embodiments, salts include sodium chloride, potassium chloride, sodium thiosulfate, sodium bisulfite and ammonium sulfate. In some embodiments, the salt is sodium chloride.

Optionally one or more acceptable surfactants, preferably nonionic surfactants, or co-solvents can be included in the compositions to enhance solubility of the components of the compositions or to impart physical stability, or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40; polysorbate 20, 60 and 80; polyoxyethylene/polyoxypropylene surfactants (e.g., Pluronic® F-68, $F_{84}$ and P-103); cyclodextrin; or other agents known to those of skill in the art. Typically, such co-solvents or surfactants are employed in the compositions at a level of from about 0.01% to about 2% by weight.

In some embodiments, pharmaceutical packs or kits comprising one or more containers filled with one or more compositions described herein are provided. Optionally associated with such container(s) can be a notice in the form prescribed by a governmental agency regulating the manufacture, use or sale of pharmaceuticals or biological products, which notice reflects approval by the agency of manufacture, use or sale for human administration for treating a condition, disease, or disorder described herein. In some embodiments, the kit contains more than one compound described herein. In some embodiments, the kit comprises a compound described herein in a single injectable dosage form, such as a single dose within an injectable device such as a syringe with a needle.

In some embodiments, the methods comprise administering to the subject one or more compositions described herein or a pharmaceutically acceptable salt, solvate or prodrug thereof, or a pharmaceutical composition of the same. In some embodiments, the subject is a subject in need of such treatment. As described herein, in some embodiments, the subject is a mammal, such as, but not limited to, a human.

In some embodiments, also provided are one or more compositions described above, or a pharmaceutically acceptable salt, solvate or prodrug thereof, for use in the manufacture of a medicament for Any medicament having utility in an application described herein can be used in co-therapy, co-administration or co-formulation with a composition as described above. Therefore, the compositions described herein can be administered either before, concurrently with, or after such therapeutics are administered to a subject.

The additional medicament can be administered in co-therapy (including co-formulation) with the one or more of the compounds described herein.

In some embodiments, the response of the disease or disorder to the treatment is monitored and the treatment regimen is adjusted if necessary in light of such monitoring.

Frequency of administration is typically such that the dosing interval, for example, the period between one dose and the next, during waking hours is from about 1 to about 24 hours, from about 2 to about 12 hours, from about 3 to about 8 hours, or from about 4 to about 6 hours. In some embodiments, the dose is administered 1, 2, 3, or 4 times a day. It will be understood by those of skill in the art that an appropriate dosing interval is dependent to some degree on the length of time for which the selected composition is capable of maintaining a concentration of the compound(s) in the subject and/or in the target tissue (e.g., above the $EC_{50}$ (the minimum concentration of the compound which inhibits the transporter's activity by 90%). Ideally, the concentration remains above the $EC_{50}$ for at least 100% of the dosing interval. Where this is not achievable, it is desired that the concentration should remain above the $EC_{50}$ for at least about 60% of the dosing interval or should remain above the $EC_{50}$ for at least about 40% of the dosing interval.

The present disclosure also provides the following non-limiting embodiments:

In order that the embodiments disclosed herein may be more efficiently understood, examples are provided below. It should be understood that these examples are for illustrative purposes only and are not to be construed as limiting the embodiments in any manner.

In some embodiments, the following embodiments are provided:

1. A method of preparing a composition comprising Compound C, comprising:
   contacting Compound A having the formula of

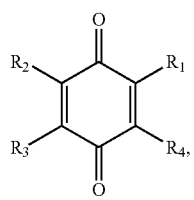

Formula I

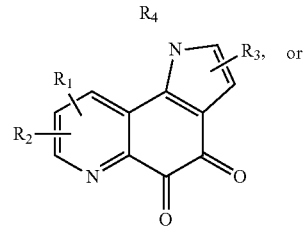

Formula VII

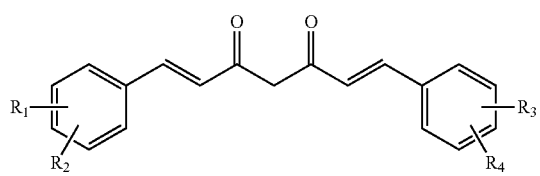

Formula VIII optionally in a solvent, wherein the solvent is free of or is not ethanol, with Compound B having the formula of

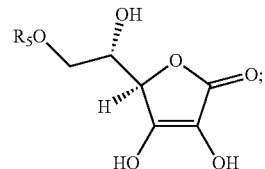

Formula II to form Compound C having the formula of

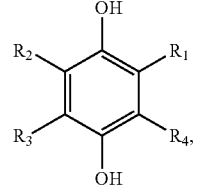

Formula III

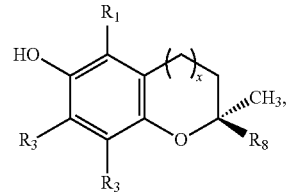

Formula VI

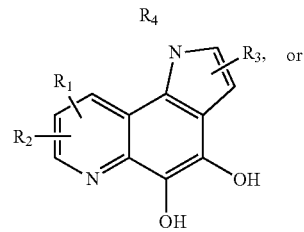

Formula IX

33
-continued

Formula X

[Structure: 1,3-diketone with two phenyl groups bearing R1, R2 and R3, R4 substituents]

wherein:

R₅ is H, OH, NH₂, NO₂, R₆—C(O)—, optionally substituted carbocycle, optionally substituted aryl group, optionally substituted heteroaryl group, branched or unbranched alkyl alcohol, halo, branched or unbranched alkyl, branched or unbranched alkenyl, branched or unbranched alkenyl ester, amide, cyano, alkoxy, haloalkyl, aklylsulfonyl, nitrite, or alkylsulfanyl; and R₁, R₂, R₃, R₄, R₆, and R₈ are each, independently, H, OH, NH₂, NO₂, optionally substituted carbocycle, optionally substituted aryl group, optionally substituted heteroaryl group, branched or unbranched alkyl alcohol, halo, branched or unbranched alkyl, branched or unbranched alkenyl branched or unbranched carboxylic acid, branched or unbranched alkyl ester, branched or unbranched alkenyl ester, amide, cyano, alkoxy, haloalkyl, aklylsulfonyl, nitrite, or alkylsulfanyl; or R₂ and R₃ are together optionally substituted cycloalkyl, optionally substituted cycloheteroalkyl, optionally substituted aryl, or optionally substituted heteroaryl.

2. The method of embodiment 1, wherein Compound A has the formula of

Formula I-I

[Structure: 2,3-dimethoxy-5-methyl-benzoquinone with isoprenoid chain, subscript n]

Formula I-II

[Structure: 2-methyl-1,4-naphthoquinone with isoprenoid chain, subscript o]

Formula I-III

[Structure: 2-methyl-1,4-naphthoquinone with prenyl chain, subscript p]

34
-continued

Formula I-IV

[Structure: benzoquinone with R1, R2, R3 substituents and hydroxy-methyl prenyl chain, subscript q]

Formula I-V

[Structure: benzoquinone with R1, R2, R3 substituents and saturated isoprenoid tail with CH3, subscript r]

Formula VII-I

[Structure: pyrrolo-quinoline dione with R1, R2, R3 substituents]

Formula VIII-I

[Structure: curcumin-like bis-styryl diketone with R1, R2, R3, R4]

or a combination thereof

3. The method of embodiment 1, wherein Compound B has the formula of

Formula II-I

[Structure: ascorbic acid ester with R₆—C(O)—O— group]

4. The method of embodiment 3, wherein Compound C has the formula of

Formula III-I

[Structure: hydroquinone with two methoxy groups, methyl, and prenyl chain with subscript n]

-continued

Formula III-II
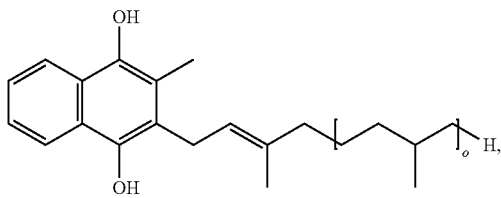

Formula III-III
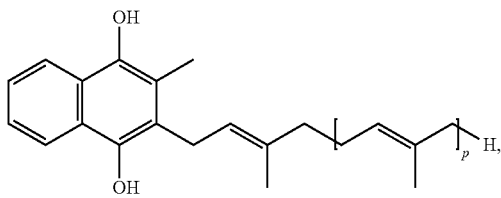

Formula III-IV
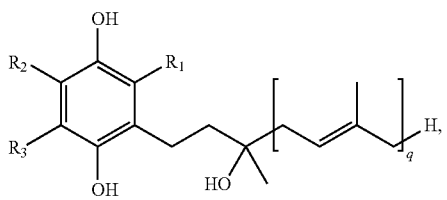

Formula III-V
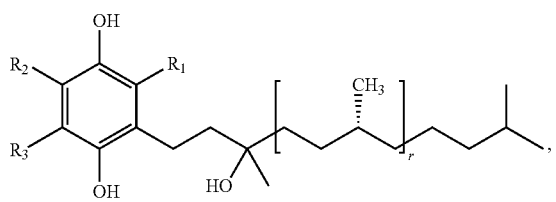

Formula VI-I
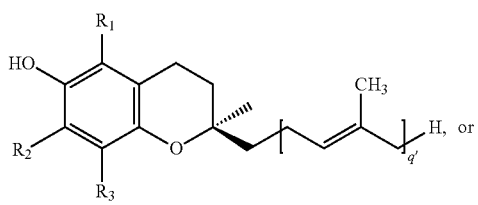

Formula VI-II
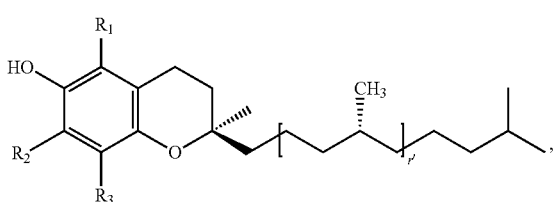

Formula VII-II
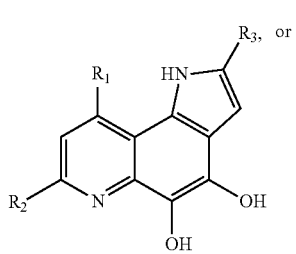

-continued

Formula VIII-II
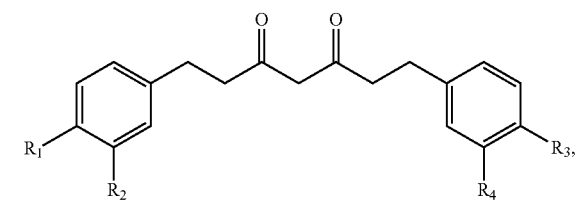

or a combination thereof.

5. The method of any one of embodiments 1-4, wherein the solvent is a non-toxic solvent.

6. The method of embodiment 5, wherein the non-toxic solvent is a non-toxic organic solvent.

7. The method of embodiment 6, wherein the non-toxic organic solvent is a non-toxic terpenoid such as a natural plant based terpenoid.

8. The method of embodiment 7, wherein the non-toxic terpenoid has the formula of Formula V
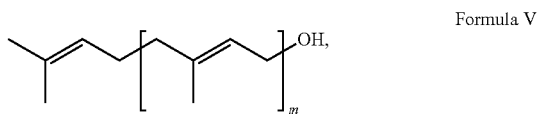

wherein m is 0-10.

9. The method of embodiment 8, wherein the non-toxic terpenoid has the formula of

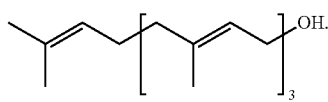

10. The method of embodiment 1, wherein the method comprises:
contacting Compound A having the formula of Formula I-I
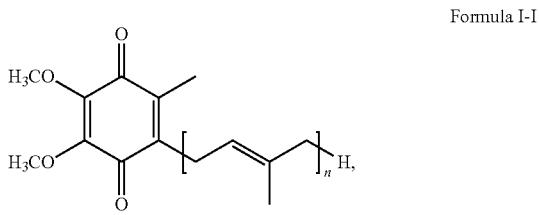

Formula I-II
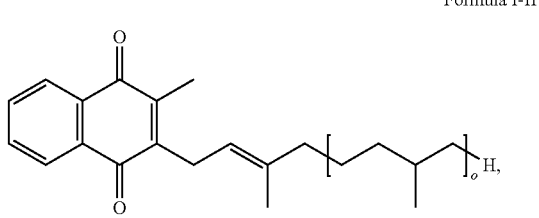

Formula I-III
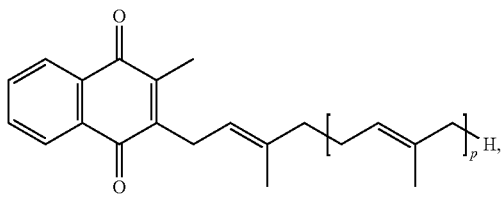
Formula I-IV
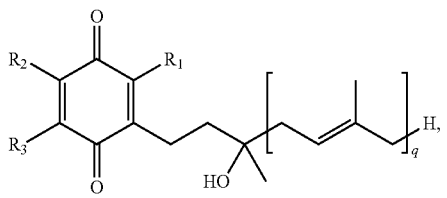
Formula I-V, or a combination thereof in the solvent having the formula of
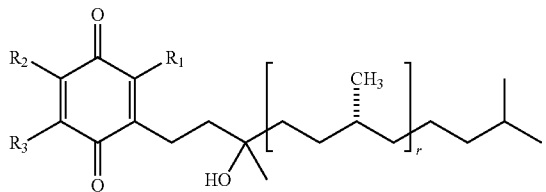
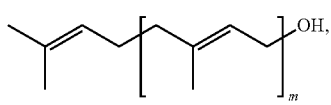
with Compound B having the formula of
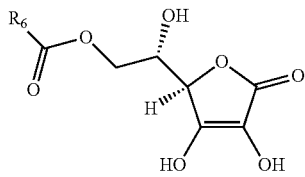
to form Compound C having the formula of
Formula III-I
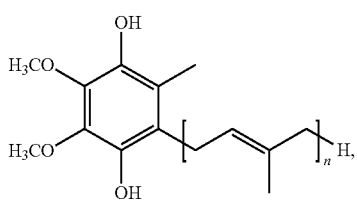
Formula III-II
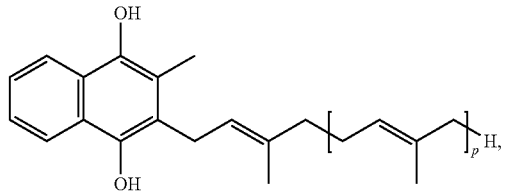
Formula III-III
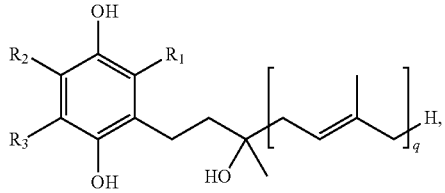
Formula III-IV
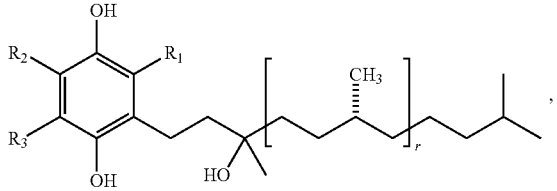
Formula III-V
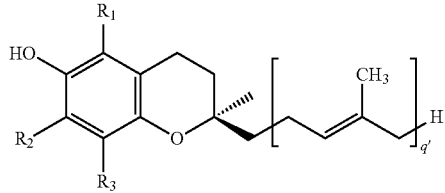
Formula VI-I, or
Formula VI-II
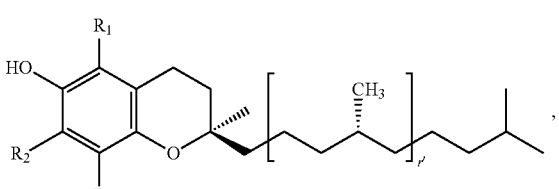
or a combination thereof.

11. The method of embodiment 10, wherein the method comprises: contacting Compound A having the formula of Formula I-I
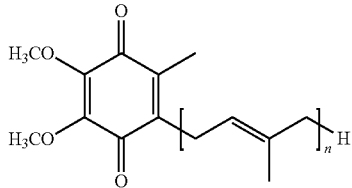

in the solvent having the formula of

Formula V
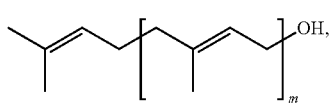

with Compound B having the formula of

Formula II-I
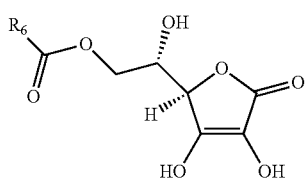

to form Compound C having the formula of

Formula III-I
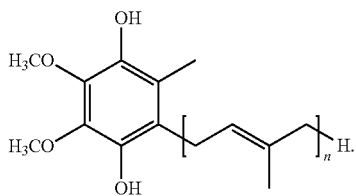

12. The method of embodiment 11, wherein the method comprises:
contacting Compound A having the formula of Formula I-I
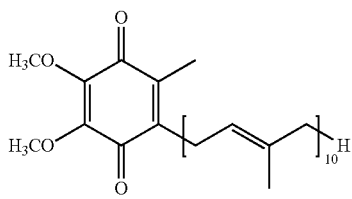

in the solvent having the formula of

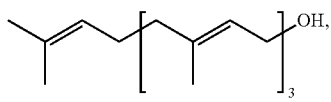

with Compound B having the formula of

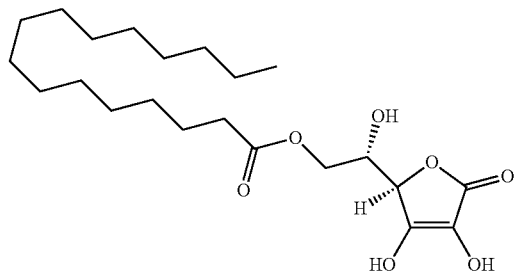 [SMILES: CCCCCCCCCCCCCCCC(=O)OC[C@H](O)[C@H]1OC(=O)C(O)=C1O]

to form the compound having the formula of

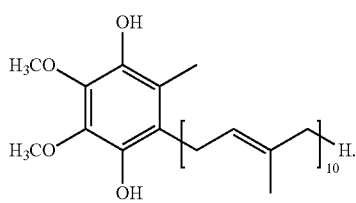

13. A method of preparing a compound having the formula of

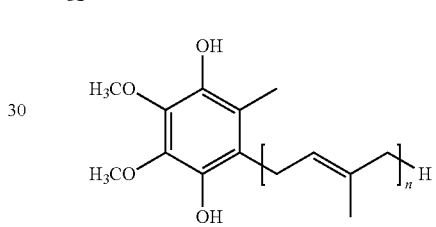

Formula III-I comprising:
contacting Compound A having the formula of

Formula I-I
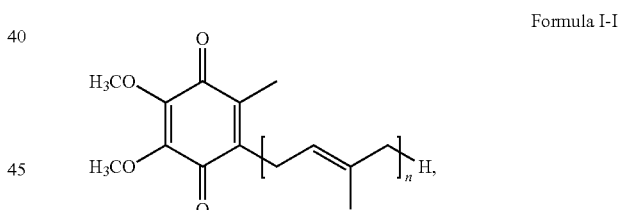

in the solvent having the formula of

Formula V
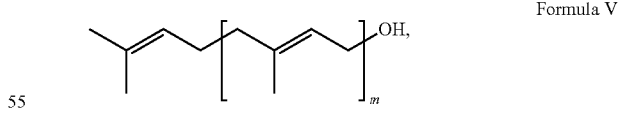

with Compound B having the formula of

Formula II-I
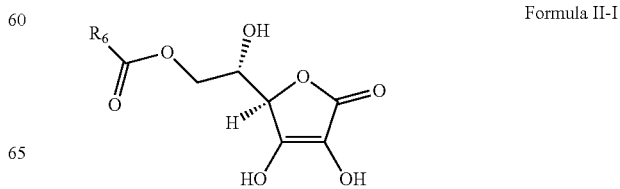

to form the compound having the formula of

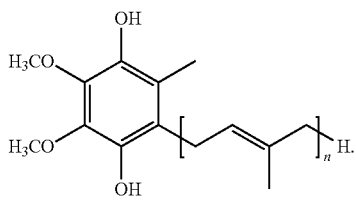
Formula III-I

14. A method of preparing a compound having the formula of

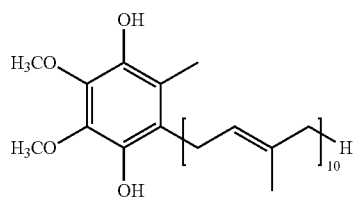

comprising: reducing Compound A having the formula of

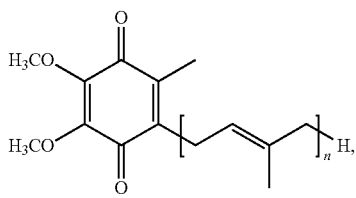
Formula I-I in the solvent having the formula c

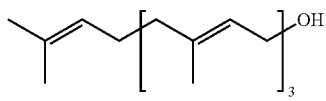

with Compound B having the formula of

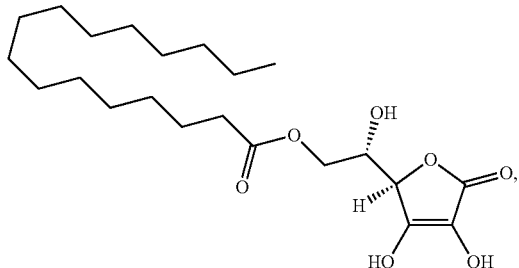 [SMILES: CCCCCCCCCCCCCCCC(=O)OC[C@H](O)[C@H]1OC(=O)C(O)=C1O]

to form the compound having the formula of

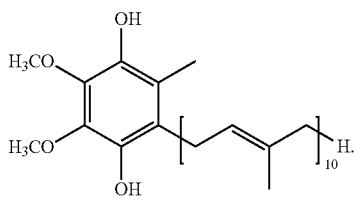

15. The method of any one of embodiments 1-14, wherein the method comprising:
    a. heating the solvent in a mixing vessel to about 35-75° C., preferably 45-65° C.;
    b. adding Compound A to the solvent of the step a to form a translucent solution;
    c. adding Compound B to the solution of step b to form a mixture and stirring the mixture until no visible second compound on the surface of the mixture;
    d. replacing the air in the vessel with an inert gas and sealing the vessel air tight; and
    e. stirring the mixture of step d for a period of time at an elevated temperature.
16. The method of embodiment 15, wherein the inert gas is Nitrogen or Argon.
17. The method of embodiment 16, wherein the inert gas is Argon.
18. The method of any one of embodiments 15-17, wherein the elevated temperature is in a range of about 30-100° C., about 40-80° C., or about 50-70° C.
19. The method of embodiment 18, wherein the elevated temperature is in a range of about 50-70° C.
20. The method of any one of embodiments 15-17, wherein the period of time is about 1 to about 13 days, about 2 to about 10 days or about 3 to about 6 days.
21. The method of embodiment 20, wherein the period of time is about 3 to about 6 days.
22. The method of any one of embodiments 1-21, wherein the starting weight ratio of Compound A:Compound B; the solvent is in a range of about 4:0.5:4 to about 4:4:4.
23. The method of any one of embodiments 1-21, wherein the starting weight ratio of Compound A:Compound B; the solvent is about 4:2:4.
24. A composition comprising:
    Compound A having the formula of

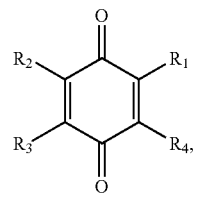
Formula I

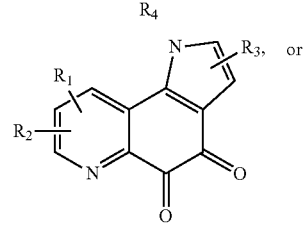
Formula VII

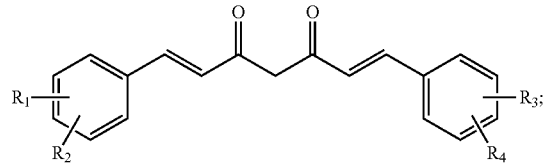
Formula VIII

Compound B having the formula of

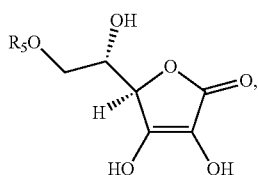

Formula II and
  optionally a non-toxic solvent, wherein the optional non-toxic solvent is free of or is not ethanol,
  wherein:
  $R_5$ is H, OH, $NH_2$, $NO_2$, $R_6$—C(=O)—, optionally substituted carbocycle, optionally substituted aryl group, optionally substituted heteroaryl group, branched or unbranched alkyl alcohol, halo, branched or unbranched alkyl, branched or unbranched alkenyl, branched or unbranched alkenyl ester, amide, cyano, alkoxy, haloalkyl, aklylsulfonyl, nitrite, or alkylsulfanyl; and
  $R_1$, $R_2$, $R_3$, $R_4$, and $R_6$, are each, independently, H, OH, $NH_2$, $NO_2$, optionally substituted carbocycle, optionally substituted aryl group, optionally substituted heteroaryl group, branched or unbranched alkyl alcohol, halo, branched or unbranched alkyl, branched or unbranched alkenyl, branched or unbranched carboxylic acid, branched or unbranched alkyl ester, branched or unbranched alkenyl ester, amide, cyano, alkoxy, haloalkyl, aklylsulfonyl, nitrite, or alkylsulfanyl; or $R_2$ and $R_3$ are together optionally substituted cycloalkyl, optionally substituted cycloheteroalkyl, optionally substituted aryl, or optionally substituted heteroaryl.

25. A composition comprising:
  Compound A having the formula of

![Formula I structure]

Formula I

![Formula VII structure]

Formula VII

![Formula VIII structure]

Formula VIII

Compound B having the formula of

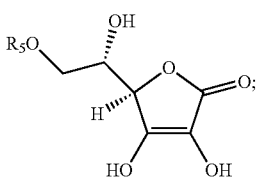

Formula II

Compound C having the formula of

![Formula III structure]

Formula III

![Formula VI structure]

Formula VI

![Formula IX structure]

Formula IX

![Formula X structure]

Formula X

Compound D having the formula of

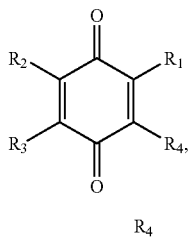

Formula IV and
  optionally a solvent with the proviso that the non-toxic solvent is not ethanol.
  wherein:
  $R_5$ is H, OH, $NH_2$, $NO_2$, $R_6$—C(=O)—, optionally substituted carbocycle, optionally substituted aryl group, optionally substituted heteroaryl group, branched or unbranched alkyl alcohol, halo, branched or unbranched alkyl, branched or unbranched alkenyl, branched or unbranched alkenyl ester, amide, cyano, alkoxy, haloalkyl, aklylsulfonyl, nitrite, or alkylsulfanyl; and $R_1$, $R_2$, $R_3$, $R_4$, $R_6$, and $R_8$ are each, independently, H, OH, $NH_2$, $NO_2$, optionally substituted carbocycle, optionally substituted aryl group, optionally substituted heteroaryl group, branched or unbranched alkyl alcohol, halo, branched or unbranched alkyl, branched or unbranched alkenyl, branched or unbranched carboxylic acid, branched or unbranched alkyl ester, branched or unbranched alkenyl ester, amide, cyano, alkoxy, haloalkyl, aklylsulfonyl, nitrite, or alkylsulfanyl; or $R_2$ and $R_3$ are together optionally substituted cycloalkyl, optionally substituted cycloheteroalkyl, optionally substituted aryl, or optionally substituted heteroaryl.

26. A composition comprising:
Compound C having the formula of

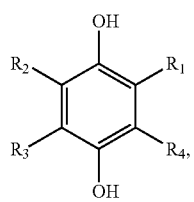

Formula III

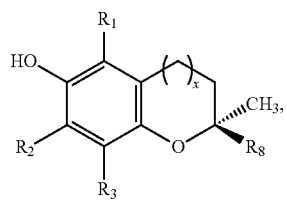

Formula VI

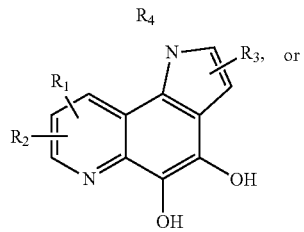

Formula IX

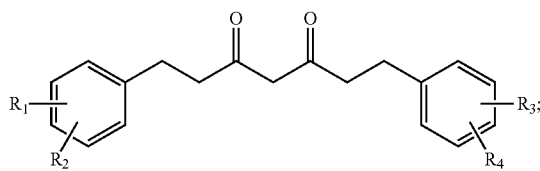

Compound D having the formula of

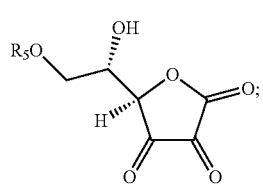

Formula IV and
optionally a solvent wherein the optional non-toxic solvent is free of or is not ethanol,
wherein:
$R_5$ is H, OH, $NH_2$, $NO_2$, $R_6$—C(=O)—, optionally substituted carbocycle, optionally substituted aryl group, optionally substituted heteroaryl group, branched or unbranched alkyl alcohol, halo, branched or unbranched alkyl, amide, cyano, alkoxy, haloalkyl, aklylsulfonyl, nitrite, or alkylsulfanyl; and $R_1$, $R_2$, $R_3$, $R_4$, $R_6$, and $R_8$ are each, independently, H, OH, $NH_2$, $NO_2$, optionally substituted carbocycle, optionally substituted aryl group, optionally substituted heteroaryl group, branched or unbranched alkyl alcohol, halo, branched or unbranched alkyl, branched or unbranched alkenyl, branched or unbranched carboxylic acid, branched or unbranched alkyl ester, branched or unbranched alkenyl ester, amide, cyano, alkoxy, haloalkyl, aklylsulfonyl, nitrite, or alkylsulfanyl; or $R_2$ and $R_3$ are together optionally substituted cycloalkyl, optionally substituted cycloheteroalkyl, optionally substituted aryl, or optionally substituted heteroaryl.

27. The composition of any one of embodiments 24-26, wherein the solvent is a non-toxic plant derived solvent.
28. The composition of any one of embodiments 24-27, wherein the non-toxic solvent is a non-toxic organic solvent.
29. The composition of any one of embodiments 24-28 wherein the non-toxic organic solvent is a non-toxic terpene or a terpenoid thereof.
30. The composition of embodiment 29, wherein the non-toxic terpenoid has the formula of

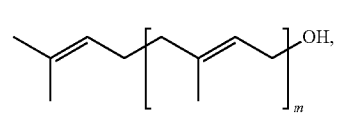

Formula V wherein m is 0-10.

31. The composition of embodiments 29, wherein the non-toxic terpenoid has the formula of

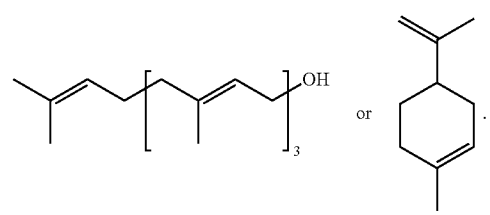

32. The composition of any one of embodiments 24-31, wherein $R_4$ has the formula of

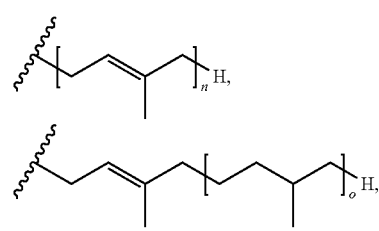

-continued

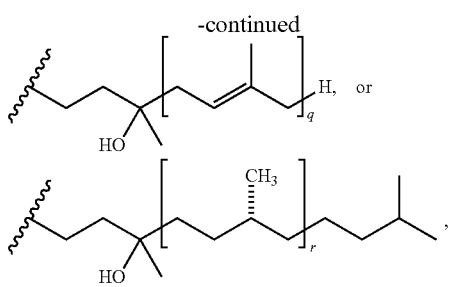

wherein n, o, q, and r are each, independently, 1-20.

33. The composition of any one of embodiments 24-32, wherein $R_1$, $R_2$, and $R_3$ are each, independently, H, branched or unbranched alkyl alcohol, branched or unbranched alkyl, branched or unbranched alkenyl, or branched or unbranched alkoxy.
34. The composition of embodiment 33, wherein $R_1$, $R_2$, and $R_3$, are each, independently, branched or unbranched $C_1$-$C_6$ alkyl alcohol, branched or unbranched $C_1$-$C_6$ alkyl, branched or unbranched alkenyl, or branched or unbranched $C_1$-$C_6$ alkoxy.
35. The composition of any one of embodiments 24, 25, and 27-34, wherein Compound A has the formula of Formula I-I

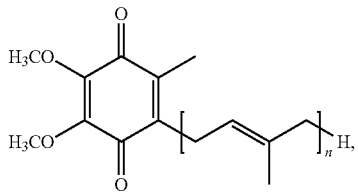

wherein n is 1-20.

36. The composition of embodiment 35, wherein n is 6-10.
37. The composition of embodiment 36, wherein Compound A has the formula of

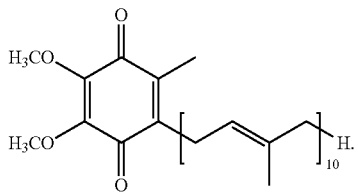

38. The composition of any one of embodiments 24-33, wherein $R_2$ and $R_3$ are together optionally substituted aryl or optionally substituted heteroaryl.
39. The composition of embodiment 38, wherein Compound A has the formula of Formula I-II

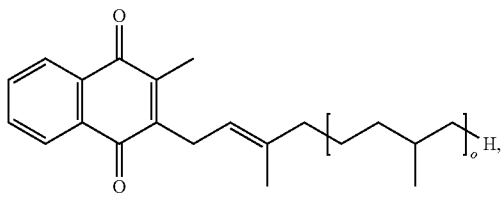

wherein o is 1-20.

40. The composition of embodiment 39, wherein o is 3.
41. The composition of embodiment 38, wherein Compound A has the formula of Formula I-III

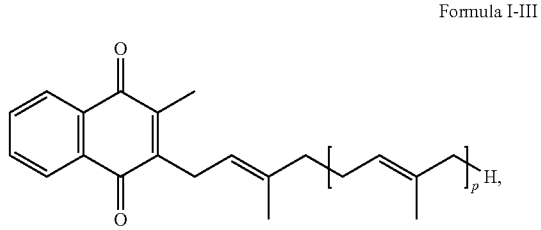

wherein p is 1-20.

42. The composition of embodiment 41, wherein p is 3 or 6.
43. The composition of any one of embodiments 24, 25, and 27-34, wherein Compound A has the formula of Formula I-IV

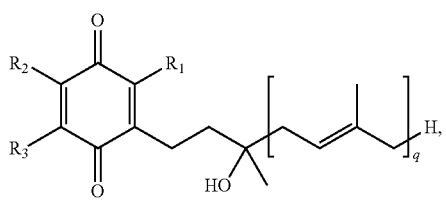

wherein q is 1-20.

44. The composition of embodiment 43, wherein q is 3.
45. The composition embodiment 44, wherein at least one of $R_1$, $R_2$, and $R_3$ is $CH_3$.
46. The composition embodiment 45, wherein Compound A has the formula of

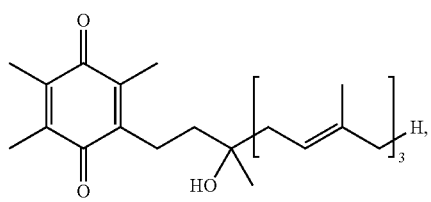

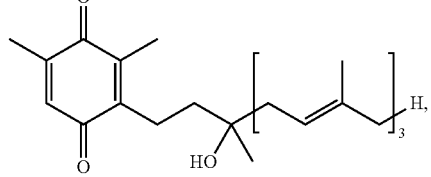

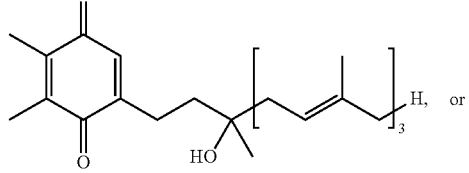

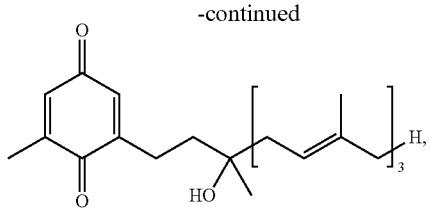

or a combination thereof.

47. The composition of any one of embodiments 24, 25, and 27-34, wherein Compound A has the formula of Formula I-V

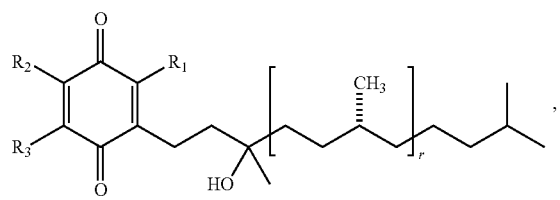

wherein r is 1-20.

48. The composition of embodiment 47, wherein r is 2.
49. The composition of embodiment 48, wherein at least one of $R_1$, $R_2$, and $R_3$ is $CH_3$.
50. The composition of embodiment 49, wherein Compound A has the formula of,

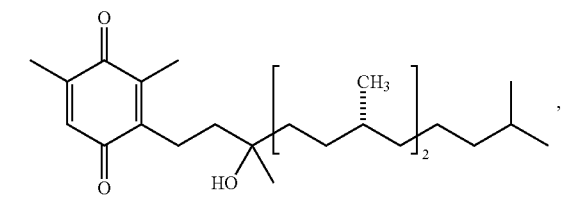

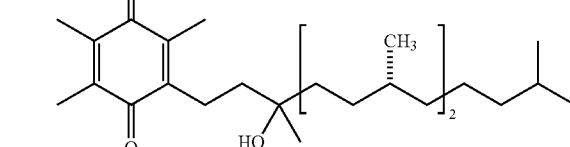

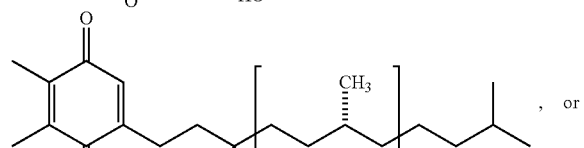

, or

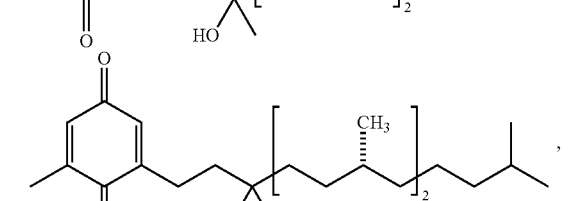

or a combination thereof.

51. The composition of any one of embodiments 24, 25, and 27-50, wherein Compound B has the formula of Formual II-I

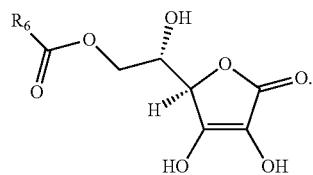

52. The composition of embodiment 51, wherein $R_6$ is branched or unbranched $C_1$-$C_{30}$ alkyl.
53. The composition of embodiment 52, wherein Compound B has the formula of

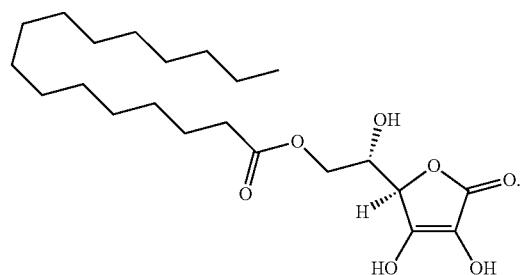 [SMILES: CCCCCCCCCCCCCCCC(=O)OC[C@H](O)[C@H]1OC(=O)C(O)=C1O]

54. The composition of any one of embodiments 25-34, wherein Compound C has the formula of Formula III-I

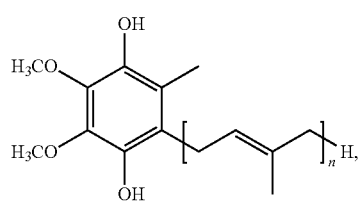

wherein n is 1-20.

55. The composition of embodiment 54, wherein n is 6-10.
56. The composition of embodiment 55, wherein Compound C has the formula of

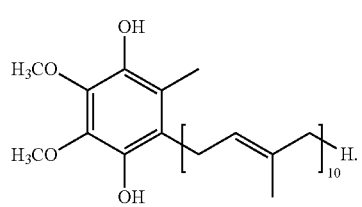

57. The composition of any one of embodiments 25-32, wherein Compound C has the formula of Formula III-II

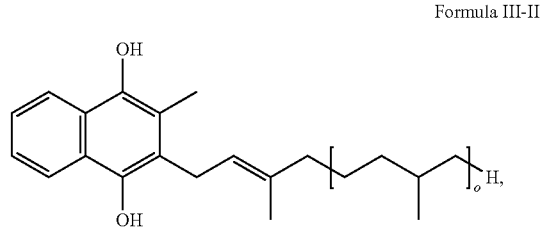

wherein o is 1-20.

58. The composition of embodiment 57, wherein o is 3.
59. The composition of embodiment 58, wherein Compound C has the formula of Formula III-III

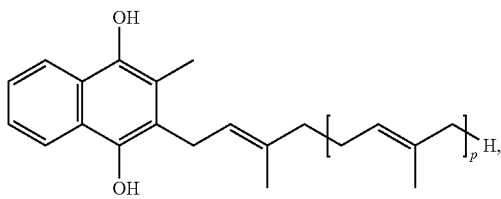

wherein p is 1-20.

60. The composition of embodiment 59, wherein p is 3 or 6.
61. The composition of any one of embodiments 25-34, wherein Compound C has the formula of Formula III-IV

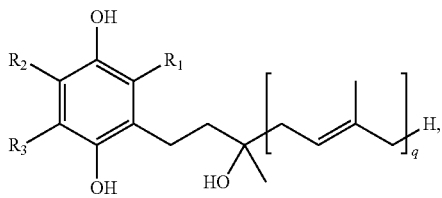

wherein q is 1-20.

62. The composition of embodiment 61, wherein q is 3.
63. The composition embodiment 62, wherein at least one of $R_1$, $R_2$, and $R_3$ is $CH_3$.
64. The composition embodiment 63, wherein Compound C has the formula of

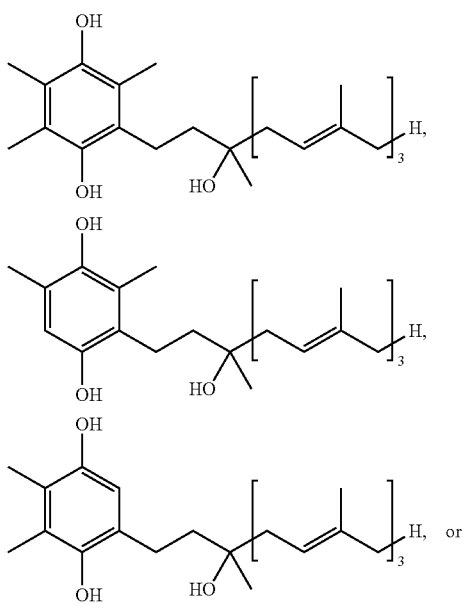

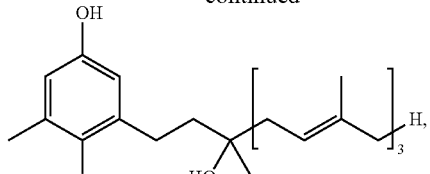

or a combination thereof.

65. The composition of any one of embodiments 25-34, wherein Compound C has the formula of Formula III-V

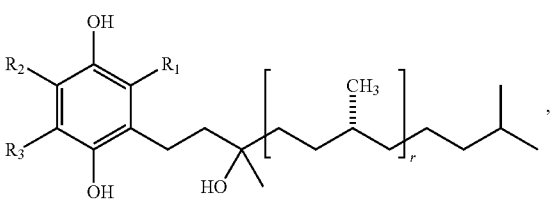

wherein r is 1-20.

66. The composition of embodiment 47, wherein r is 2.
67. The composition of embodiment 48, wherein at least one of $R_1$, $R_2$, and $R_3$ is $CH_3$.
68. The composition of embodiment 49, wherein Compound C has the formula of

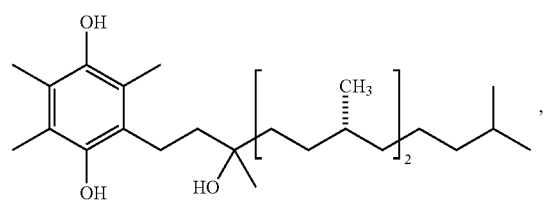

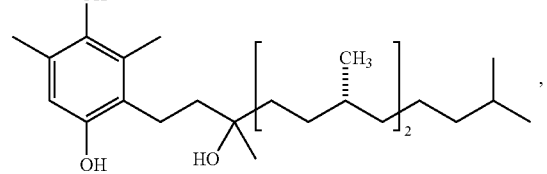

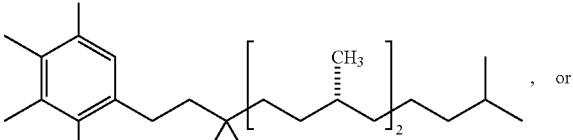

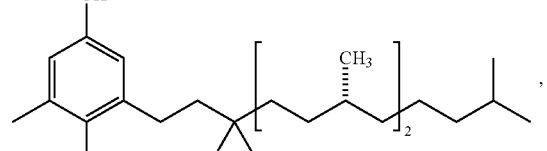

or a combination thereof.

69. The composition of any one of embodiments 52-34, wherein Compound C has the formula of

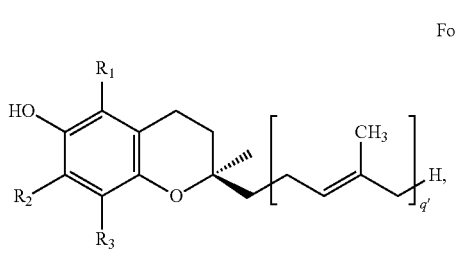

Formula VI-I wherein q' is 1-20.

70. The composition of embodiment 69, wherein q' is 3.
71. The composition embodiment 70, wherein at least one of $R_1$, $R_2$, and $R_3$ is $CH_3$.
72. The composition embodiment 71, wherein Compound C has the formula of

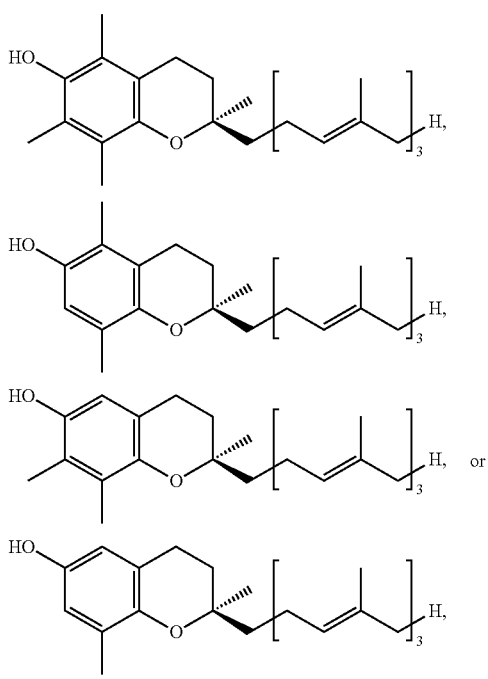

or a combination thereof.

73. The composition of any one of embodiments 25-34, wherein Compound C has the formula of Formula VI-II

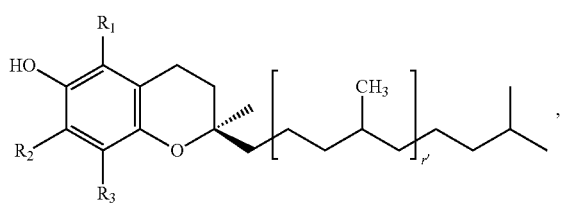

wherein r' is 1-20.

74. The composition of embodiment 73, wherein r' is 2.
75. The composition of embodiment 74, wherein at least one of $R_1$, $R_2$, and $R_3$ is $CH_3$.
76. The composition of embodiment 75, wherein Compound C has the formula of

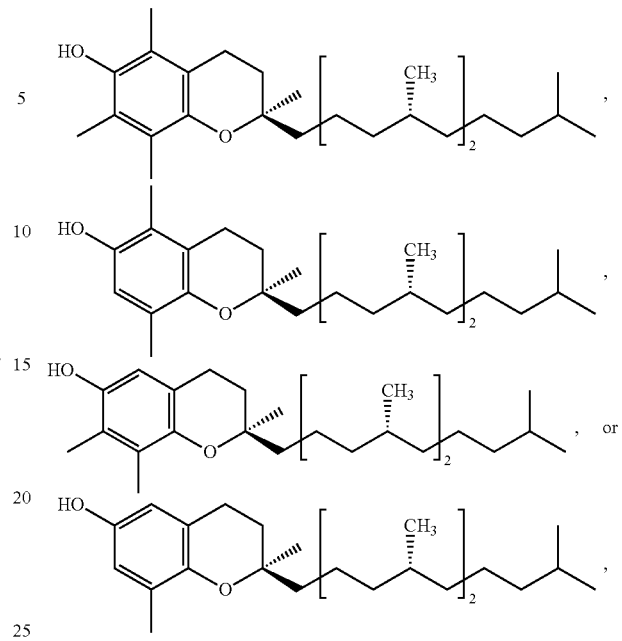

or a combination thereof.

77. The composition of any one of embodiments 25-34 and 54-76, wherein Compound D has the formula of Formula IV-I

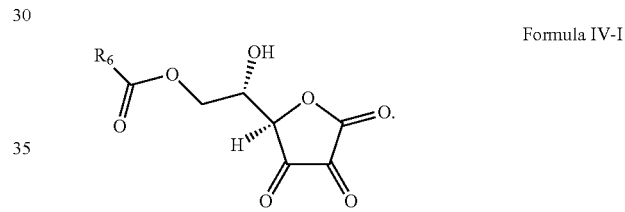

78. The composition of embodiment 77, wherein $R_6$ is branched or unbranched $C_1$-$C_{30}$ alkyl.
79. The composition of embodiment 78, wherein Compound D has the formula of

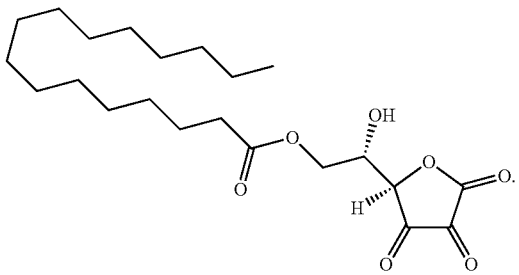 [SMILES: CCCCCCCCCCCCCCCC(=O)OC[C@H](O)[C@H]1OC(=O)C(=O)C1=O]

80. The composition of embodiment 24, wherein the composition comprises:
Compound A having the formula of Formula I-I

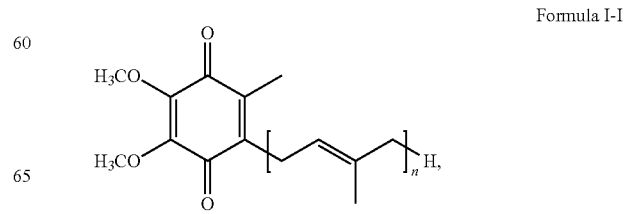

-continued

Formula I-II
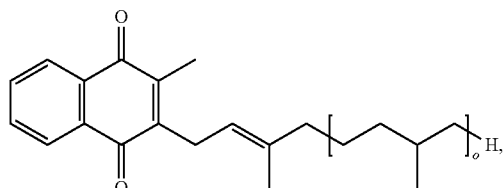

Formula I-III
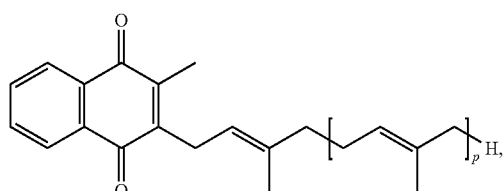

Formula I-IV
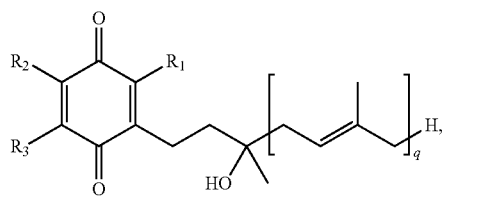

Formula I-V
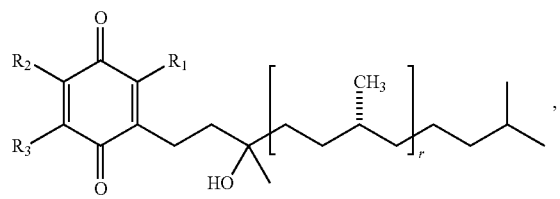

or a combination thereof;
Compound B having the formula of

Formula II-I
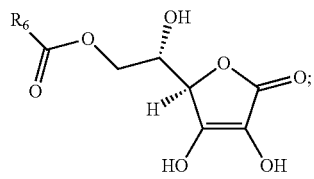

and
the solvent having the formula of

Formula V
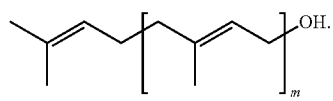

81. The composition of embodiment 24, wherein the composition comprises:
Compound A having the formula of Formula I-I
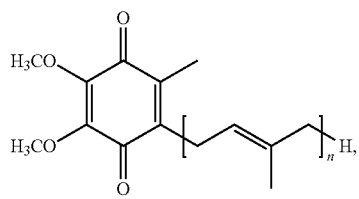

Compound B having the formula of

Formula II-I
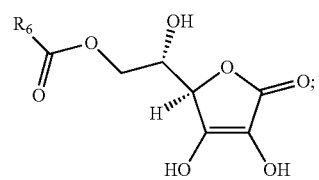

and
the solvent having the formula of

Formula V
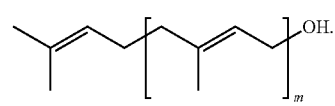

82. The composition of embodiment 81, wherein n is 10.
83. The composition of embodiment 82, wherein m is 3.
84. A composition comprising:
Compound A having the formula of

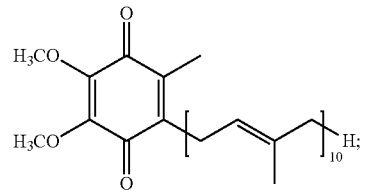

Compound B having the formula of

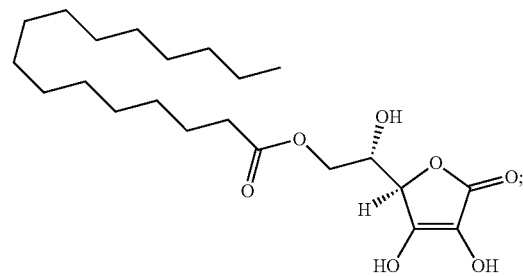 [SMILES: CCCCCCCCCCCCCCCC(=O)OC[C@H](O)[C@H]1OC(=O)C(O)=C1O]

and
a solvent having the formula of

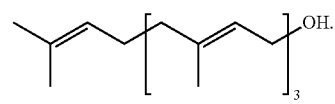

85. The composition of embodiment 24, wherein the composition comprises:
Compound A having the formula of Formula I-II
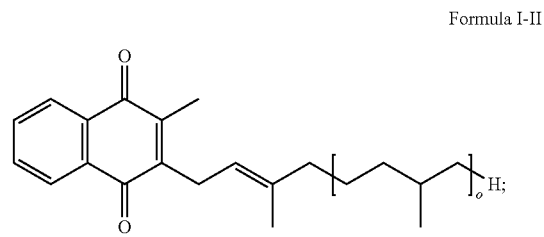

Compound B having the formula of

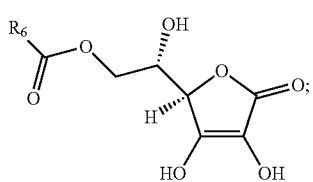
Formula II-I and
the solvent having the formula of

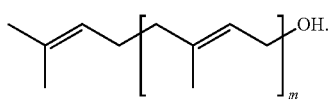
Formula V

86. The composition of embodiment 85, wherein o is 3.
87. The composition of embodiment 86, wherein m is 3.
88. A composition comprising:
Compound A having the formula of

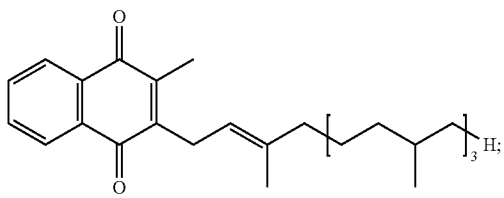

Compound B having the formula of

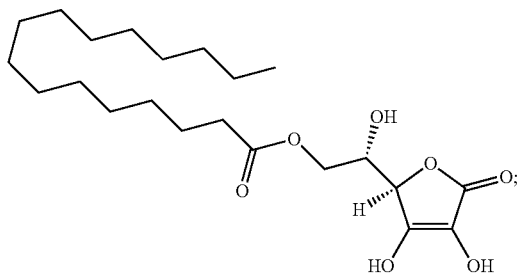 [SMILES: CCCCCCCCCCCCCCCC(=O)OC[C@H](O)[C@H]1OC(=O)C(O)=C1O]

and
a solvent having the formula of

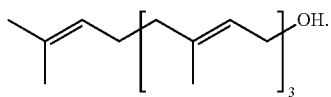

89. The composition of embodiment 24, wherein the composition comprises:
Compound A having the formula of

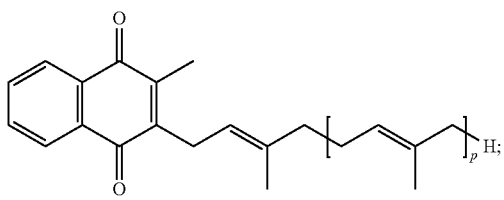
Formula I-III

Compound B having the formula of

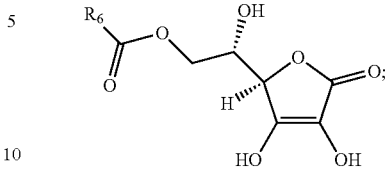
Formula II-I and
the solvent having the formula of

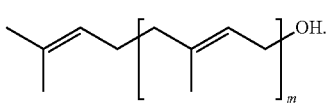
Formula V

90. The composition of embodiment 89, wherein p is 3 or 6.
91. The composition of embodiment 70, wherein m is 3.
92. A composition comprising:
Compound A having the formula of

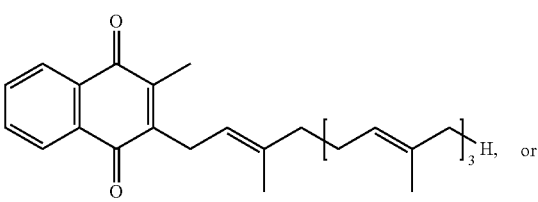, or

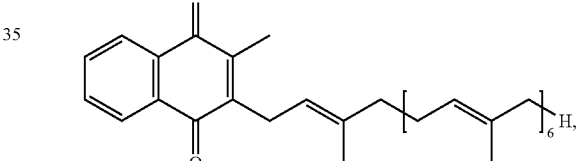

or a combination thereof;
Compound B having the formula of

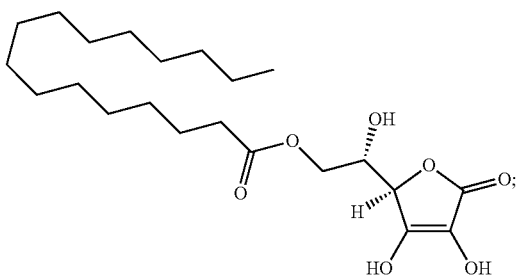 [SMILES: CCCCCCCCCCCCCCCC(=O)OC[C@H](O)[C@H]1OC(=O)C(O)=C1O]

and
a solvent having the formula of

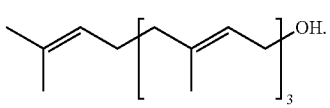

93. The composition of embodiment 24, wherein the composition comprises:

Compound A having the formula of

Formula I-IV

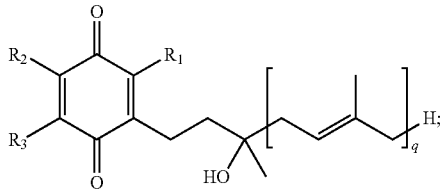

Compound B having the formula of

Formula II-I

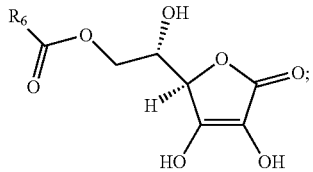

and
the solvent having the formula of

Formula V

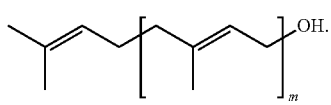

94. The composition of embodiment 93, wherein q is 3.
95. The composition of embodiment 94, wherein m is 3.
96. A composition comprising:
   Compound A having the formula of

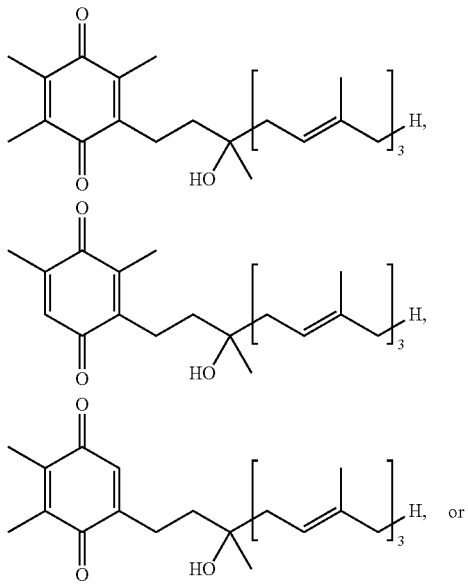

or a combination thereof;
Compound B having the formula of

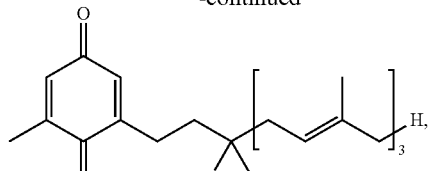

and
a solvent having the formula of

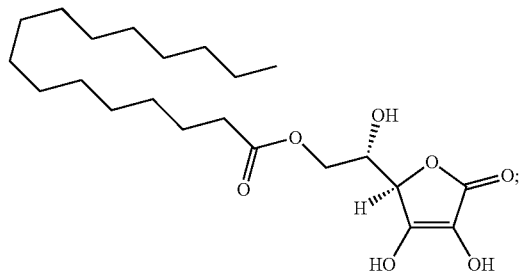 [SMILES: CCCCCCCCCCCCCCCC(=O)OC[C@H](O)[C@H]1OC(=O)C(O)=C1O]

97. The composition of embodiment 24, wherein the composition comprises:
   Compound A having the formula Formula I-V

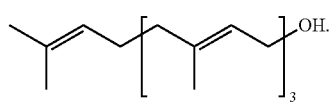

Compound B having the formula of

Formula II-I

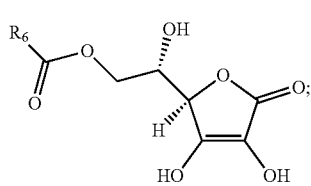

and
the solvent having the formula of

Formula V

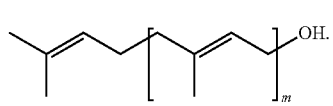

98. The composition of embodiment 97, wherein r is 2.
99. The composition of embodiment 98, wherein m is 3.

100. A composition comprising:
Compound A having the formula of

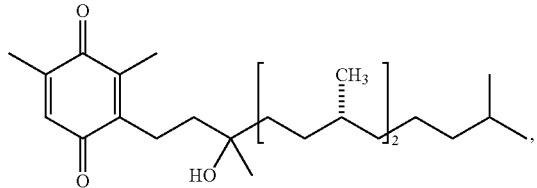

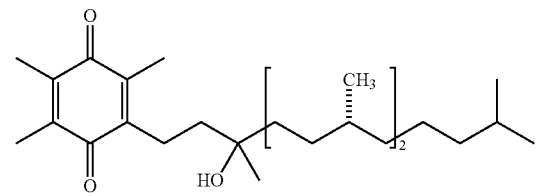

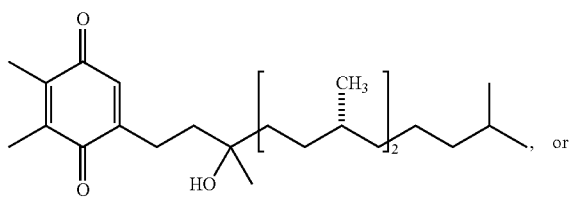, or

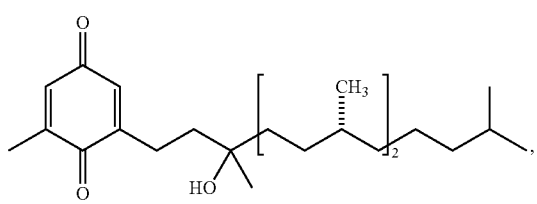

or a combination thereof;
Compound B having the formula of

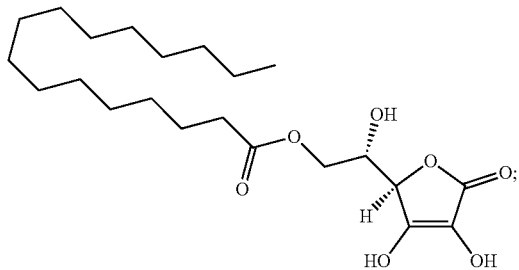 [SMILES: CCCCCCCCCCCCCCCC(=O)OC[C@H](O)[C@H]1OC(=O)C(O)=C1O]

and
a solvent having the formula of

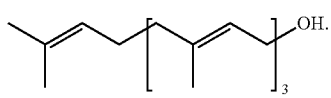

101. The composition of embodiment 25, wherein the composition comprises:

Compound A having the formula of

Formula I-I

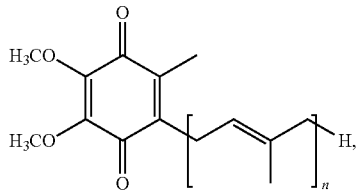

Formula I-II

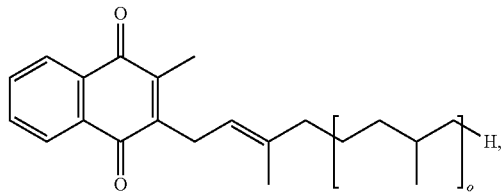

Formula I-III

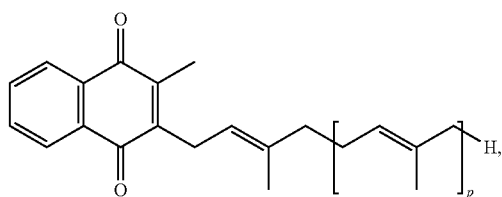

Formula I-IV

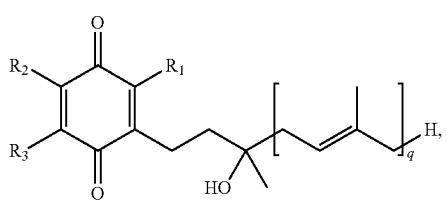

Formula I-V, or a combination thereof;
Compound B having the formula of

Formula II-I

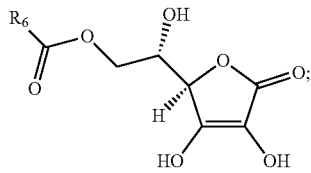

Compound C having the formula of

Formula III-I

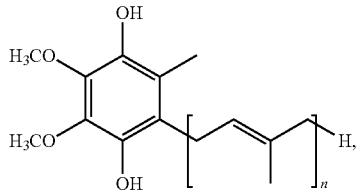

-continued

Formula III-II

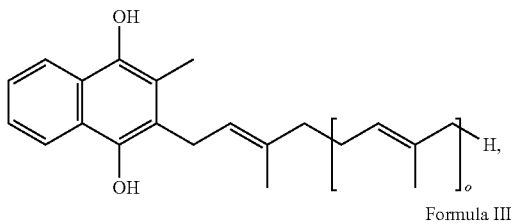

Formula III-III

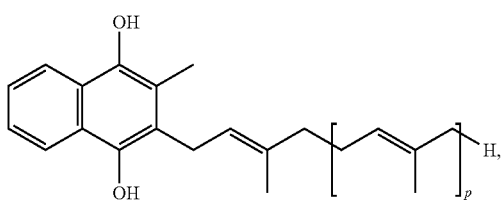

Formula III-IV

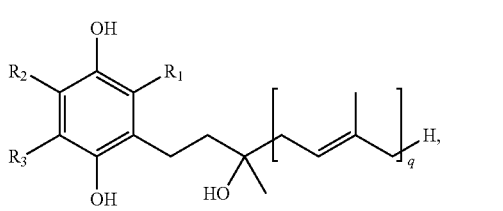

Formula III-V

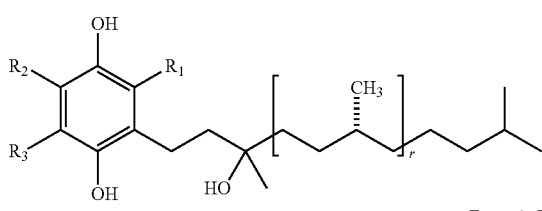

Formula VI-I

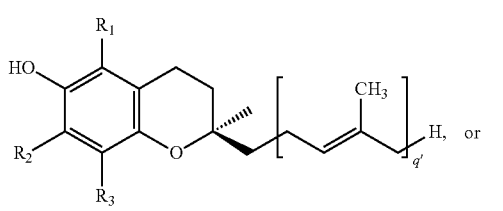

Formula VI-II

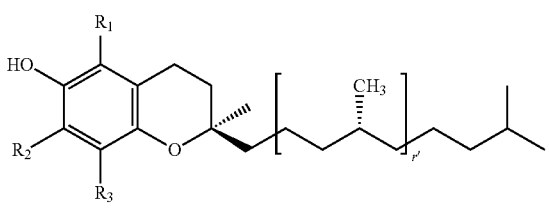

or a combination thereof;

Compound D having the formula of

Formula IV-I

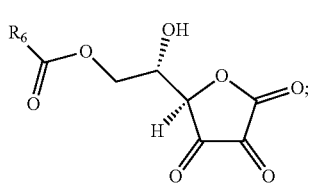

and the solvent having the formula of

Formula V

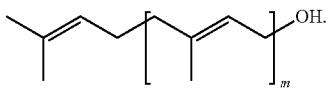

102. The composition of embodiment 25, wherein the composition comprises:

Compound A having the formula of

Formula I-I

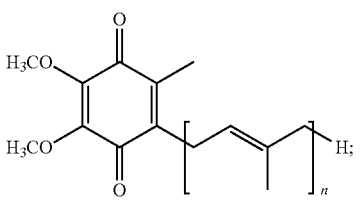

Compound B having the formula of

Formula II-I

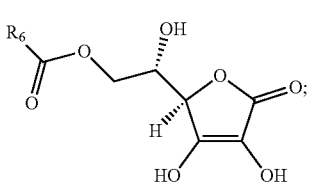

Compound C having the formula of

Formula III-I

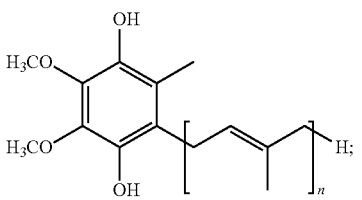

Compound D having the formula of

Formula IV-I

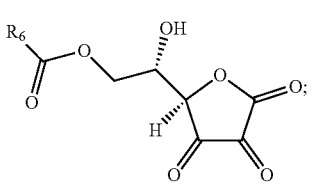

and the solvent having the formula of

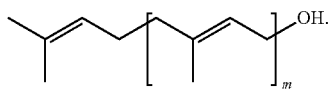

Formula V

103. The composition of embodiment 102, wherein n is 10.
104. The composition of embodiment 103, wherein m is 3.
105. A composition comprising:
    Compound A having the formula of

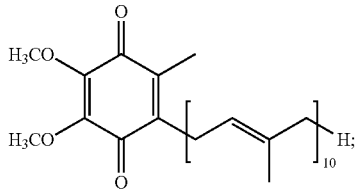

Compound B having the formula of

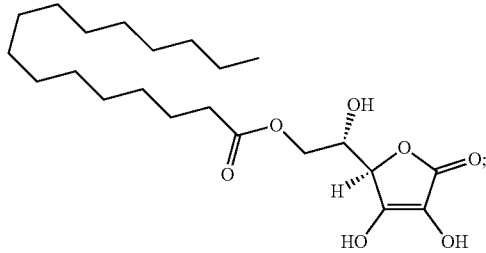 [SMILES: CCCCCCCCCCCCCCCC(=O)OC[C@H](O)[C@H]1OC(=O)C(O)=C1O]

Compound C having the formula of

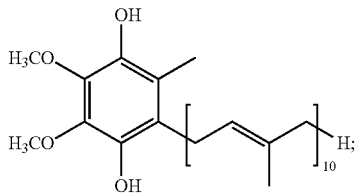

Compound D having the formula of

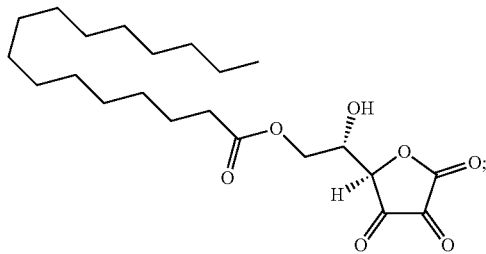 [SMILES: CCCCCCCCCCCCCCCC(=O)OC[C@H](O)[C@H]1OC(=O)C(=O)C1=O]

and
    a solvent having the formula of

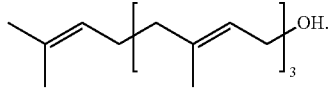

106. The composition of embodiment 25, wherein the composition comprises:
    Compound A having the formula of

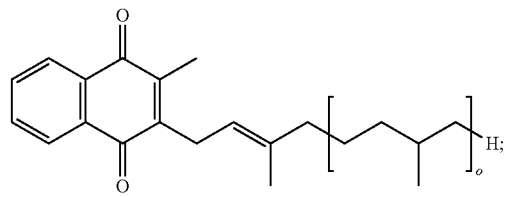

Formula I-II

Compound B having the formula of

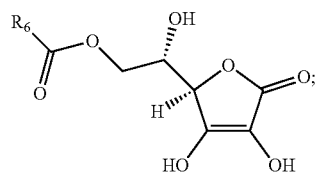

Formula II-I

Compound C having the formula of

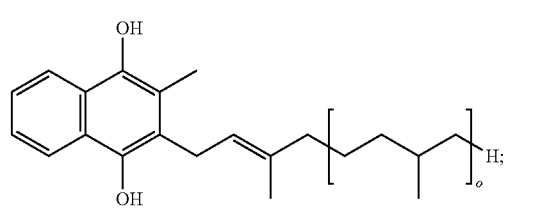

Formula III-II

Compound D having the formula of

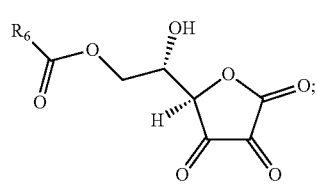

Formula IV-I and
    the solvent having the formula of

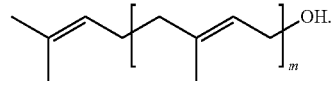

107. The composition of embodiment 106, wherein o is 3.
108. The composition of embodiment 107, wherein m is 3.

109. A composition comprising:
  Compound A having the formula of

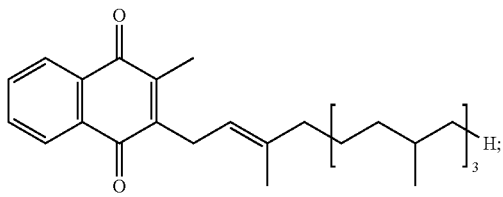

Compound B having the formula of

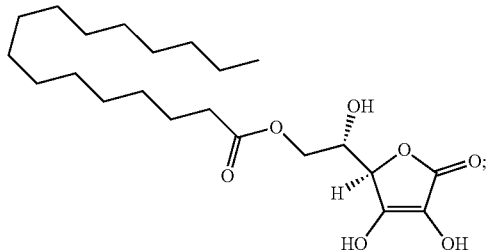 [SMILES: CCCCCCCCCCCCCCCC(=O)OC[C@H](O)[C@H]1OC(=O)C(O)=C1O]

Compound C having the formula of

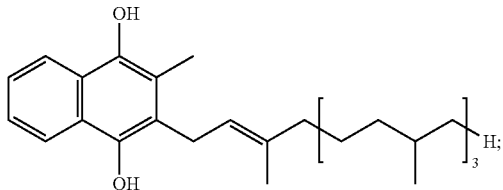

Compound D having the formula of

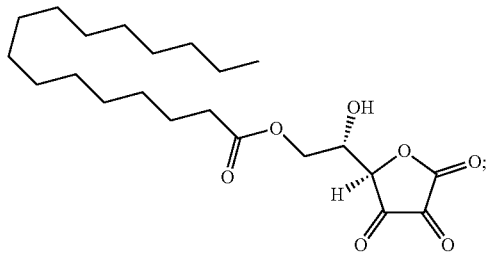 [SMILES: CCCCCCCCCCCCCCCC(=O)OC[C@H](O)[C@H]1OC(=O)C(=O)C1=O]

and
  a solvent having the formula of

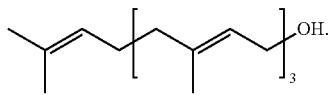

110. The composition of embodiment 24, wherein the composition comprises:
  Compound A having the formula of Formula I-III

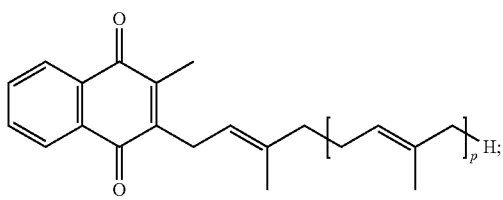

Compound B having the formula of

Formula II-I

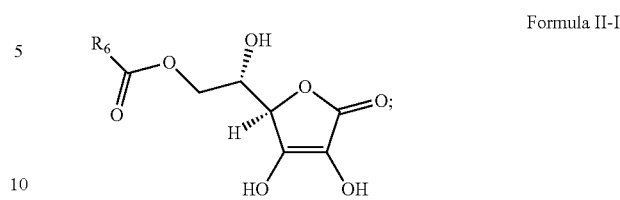

Compound C having the formula of

Formula III-III

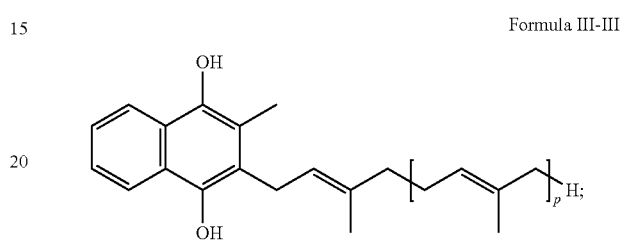

Compound D having the formula of

Formula IV-I

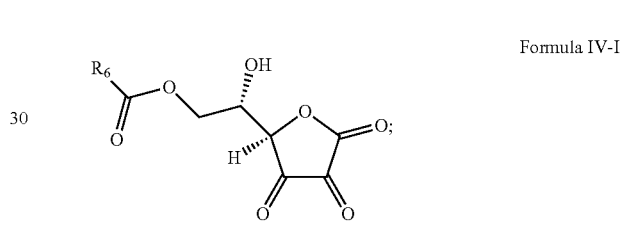

and
  the solvent having the formula of

Formula V

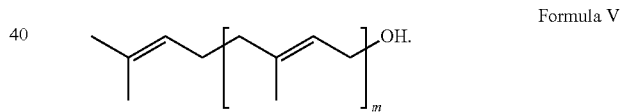

111. The composition of embodiment 110, wherein p is 3 or 6.
112. The composition of embodiment 111, wherein m is 3.
113. A composition comprising:
  Compound A having the formula of

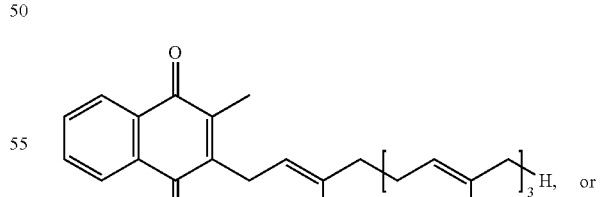

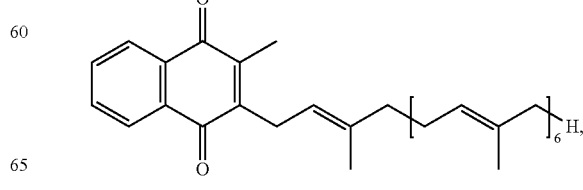

or a combination thereof;

Compound B having the formula of

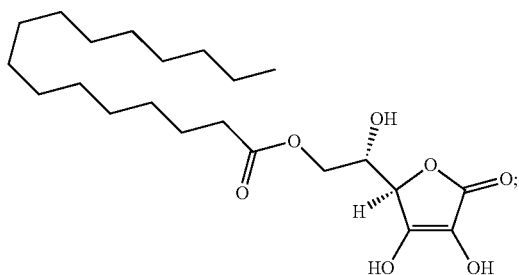 [SMILES: CCCCCCCCCCCCCCCC(=O)OC[C@H](O)[C@H]1OC(=O)C(O)=C1O]

Compound C having the formula of

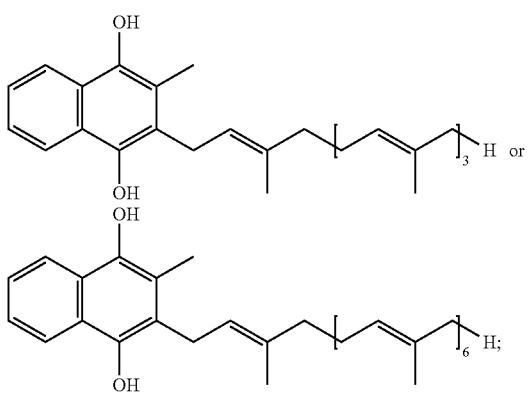

Compound D having the formula of

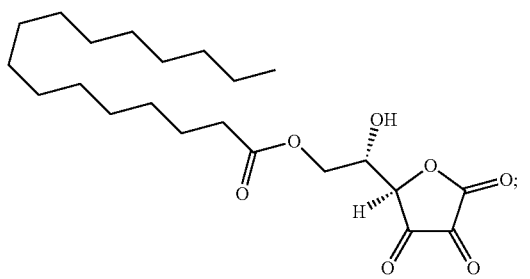 [SMILES: CCCCCCCCCCCCCCCC(=O)OC[C@H](O)[C@H]1OC(=O)C(=O)C1=O]

and
a solvent having the formula of

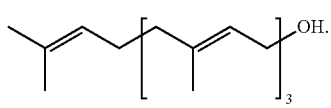

114. The composition of embodiment 25, wherein the composition comprises:
Compound A having the formula of Formula I-IV

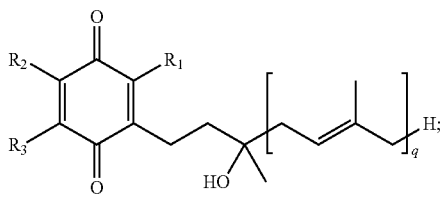

Compound B having the formula of

Formula II-I

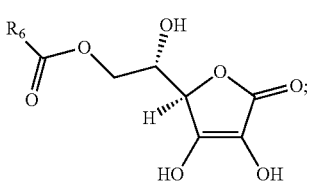

Compound C having the formula of

Formula III-IV Formula III-III

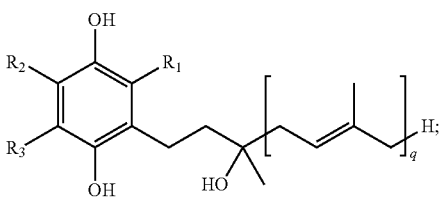

Compound D having the formula of

Formula IV-I

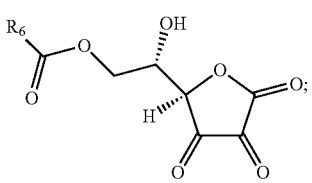

and
the solvent having the formula of

Formula V

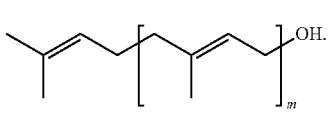

115. The composition of embodiment 114, wherein q is 3.
116. The composition of embodiment 115, wherein m is 3.
117. A composition comprising:
Compound A having the formula of

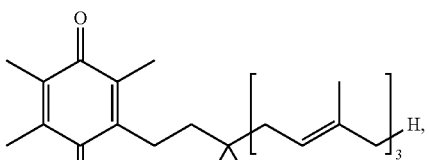

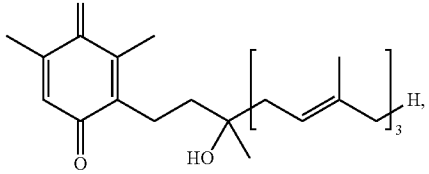

-continued

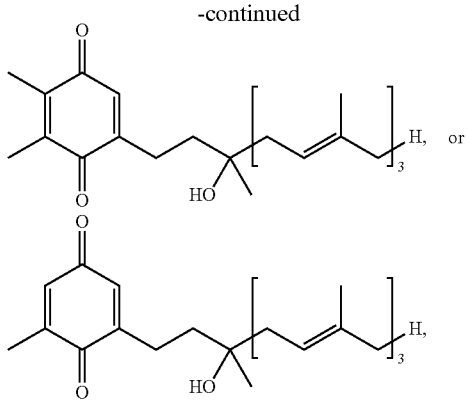

or a combination thereof;
Compound B having the formula of

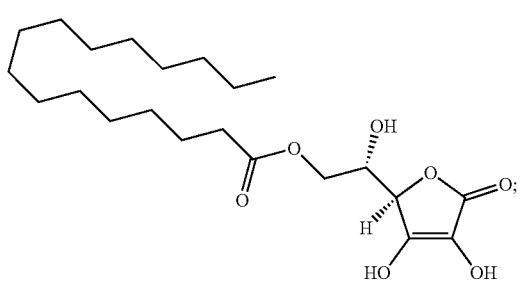 [SMILES: CCCCCCCCCCCCCCCC(=O)OC[C@H](O)[C@H]1OC(=O)C(O)=C1O]

Compound C having the formula of

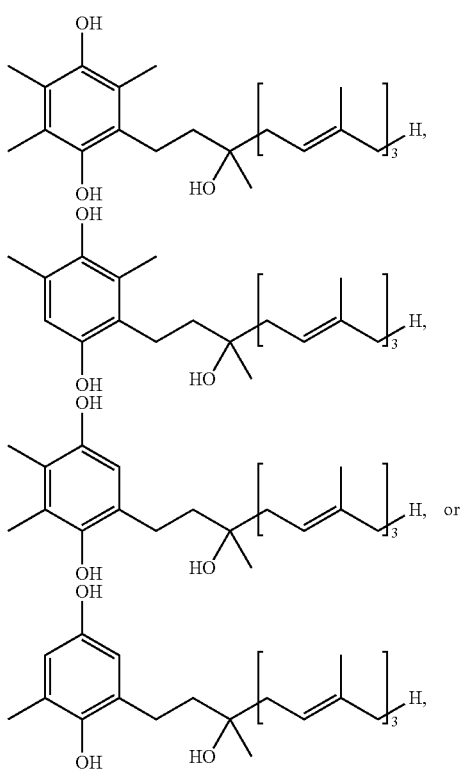

or a combination thereof;

Compound D having the formula of

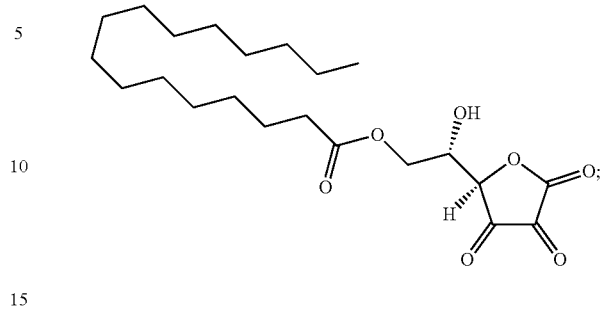

and
a solvent having the formula of

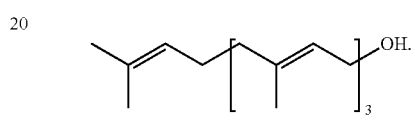

118. The composition of embodiment 25, wherein the composition comprises:
Compound A having the formula Formula I-V

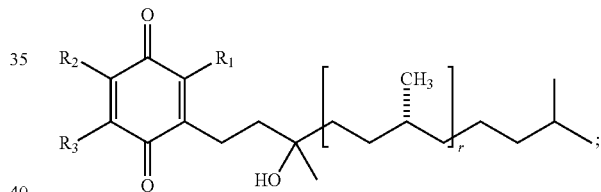

Compound B having the formula of

Formula II-I

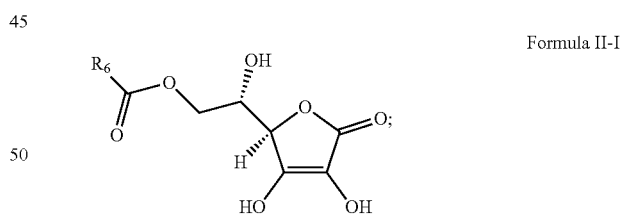

Compound C having the formula

Formula III-V

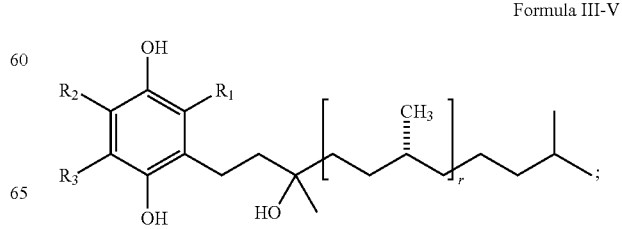

Compound D having the formula of

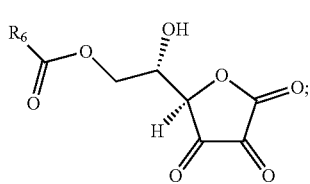

and the solvent having the formula of

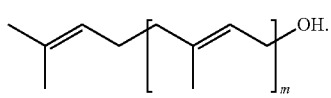

119. The composition of embodiment 118, wherein r is 2.
120. The composition of embodiment 119, wherein m is 3.
121. A composition comprising:

Compound A having the formula of

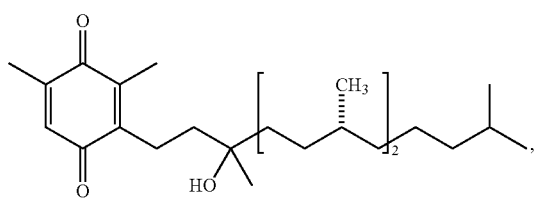

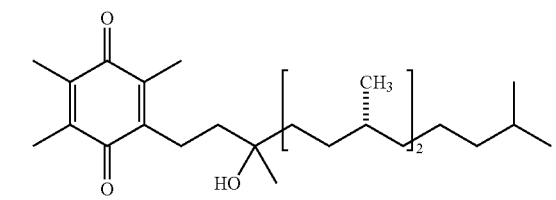

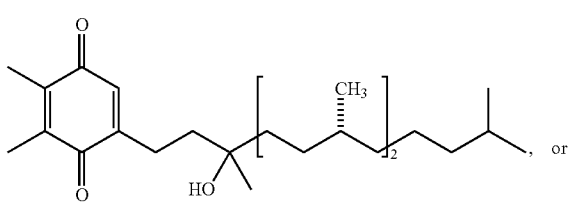

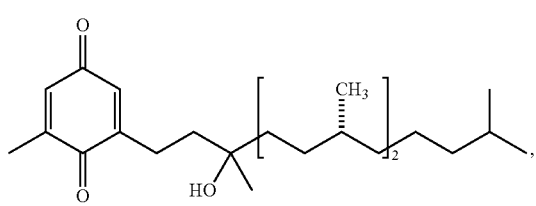

or a combination thereof;

Compound B having the formula of

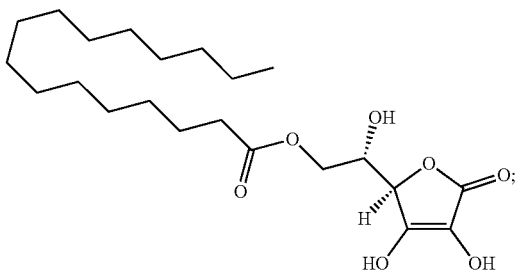 [SMILES: CCCCCCCCCCCCCCCC(=O)OC[C@H](O)[C@H]1OC(=O)C(O)=C1O]

Compound C having the formula of

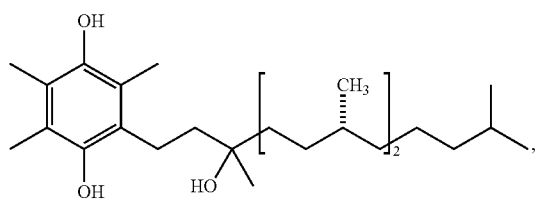

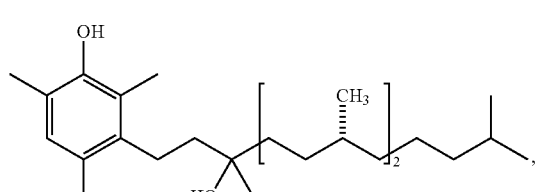

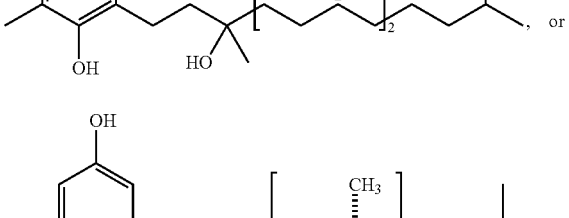

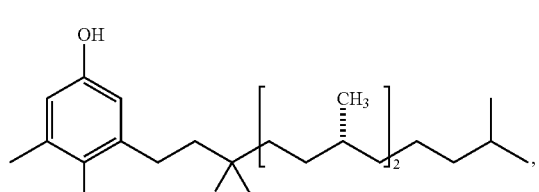

or a combination thereof;
Compound D having the formula of

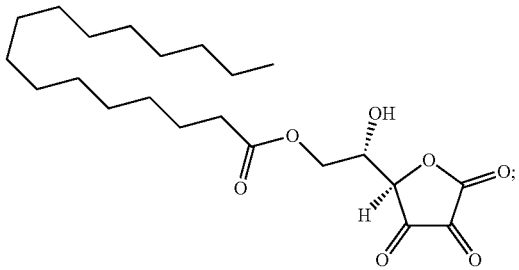 [SMILES: CCCCCCCCCCCCCCCC(=O)OC[C@H](O)[C@H]1OC(=O)C(=O)C1=O]

and a solvent having the formula of

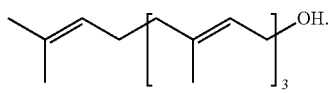

122. The composition of embodiment 25, wherein the composition comprises:
Compound A having the formula of Formula I-IV

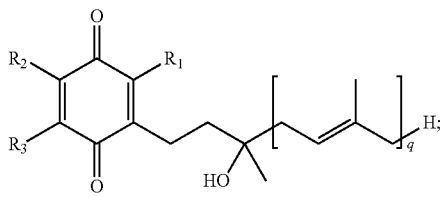

Compound B having the formula of

Formula II-I

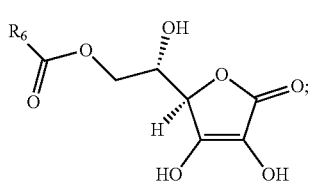

Compound C having the formula

Formula VI-I

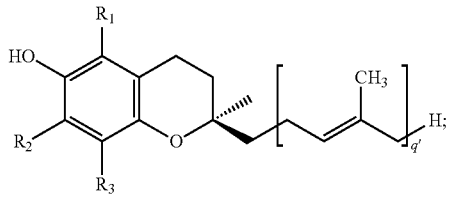

Compound D having the formula of

Formula IV-I

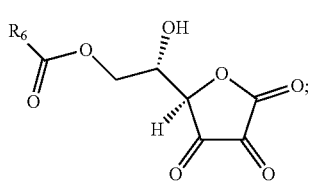

and
the solvent having the formula of

Formula V

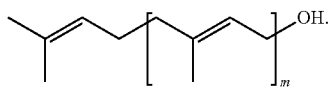

123. The composition of embodiment 122, wherein q is 3.
124. The composition of embodiment 123, wherein m is 3.

125. A composition comprising:
Compound A having the formula of

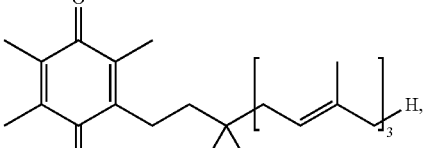

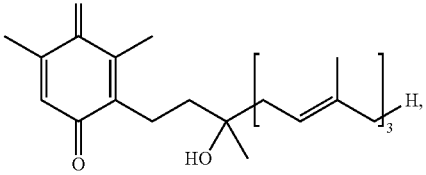

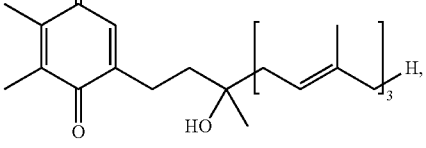

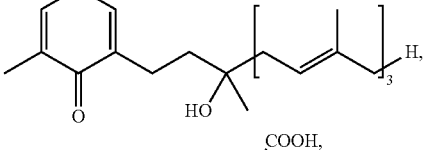

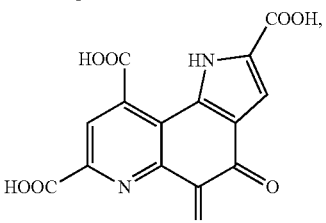

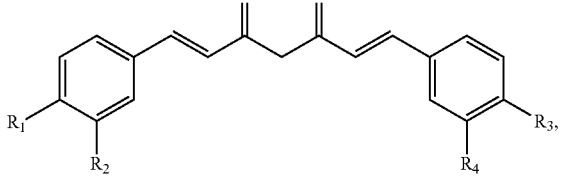

or a combination thereof;
Compound B having the formula of

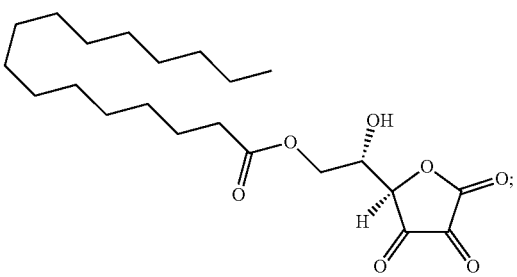 [SMILES: CCCCCCCCCCCCCCCC(=O)OC[C@H](O)[C@H]1OC(=O)C(=O)C1=O]

Compound C having the formula of

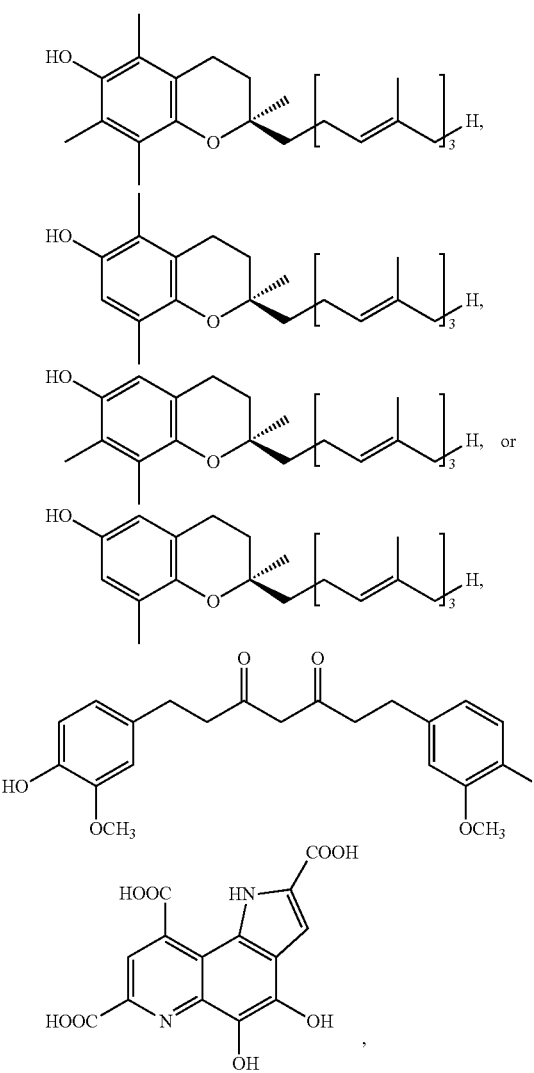

or a combination thereof;
Compound D having the formula of

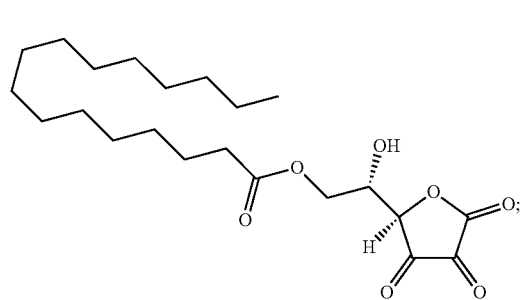 [SMILES: CCCCCCCCCCCCCCCC(=O)OC[C@H](O)[C@H]1OC(=O)C(=O)C1=O]

and
a solvent having the formula of

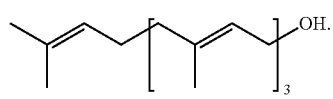

126. The composition of embodiment 25, wherein the composition comprises:
Compound A having the formula Formula I-V

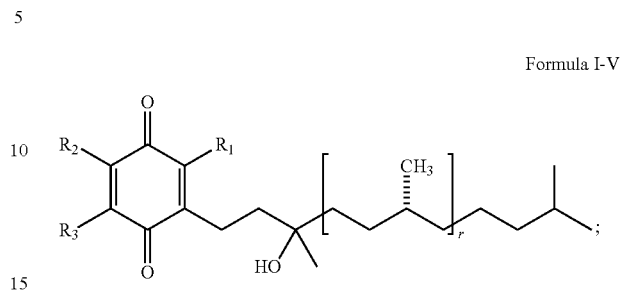

Compound B having the formula of

Formula II-I

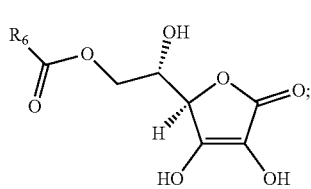

Compound C having the formula

Formula VI-II

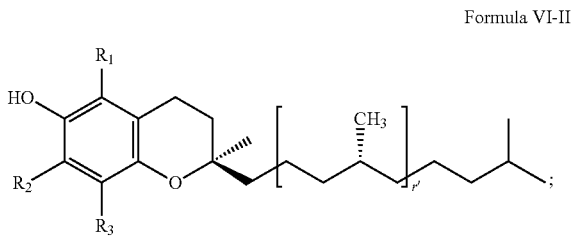

Compound D having the formula of

Formula IV-I

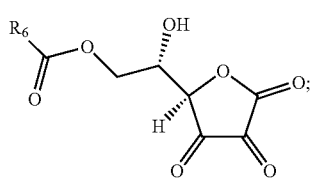

and
the solvent having the formula of

Formula V

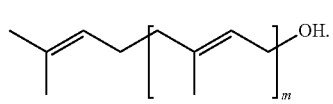

127. The composition of embodiment 126, wherein r is 2.
128. The composition of embodiment 127, wherein m is 3.

129. A composition comprising:

Compound A having the formula of

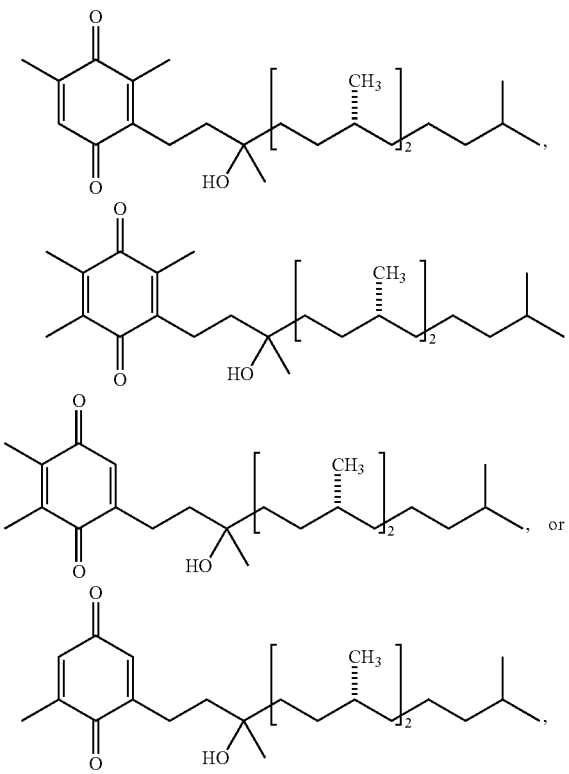

or a combination thereof;

Compound B having the formula of

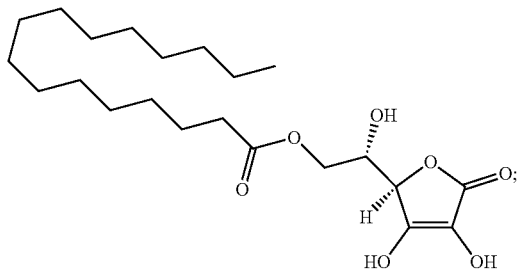 [SMILES: CCCCCCCCCCCCCCCC(=O)OC[C@H](O)[C@H]1OC(=O)C(O)=C1O]

Compound C having the formula of

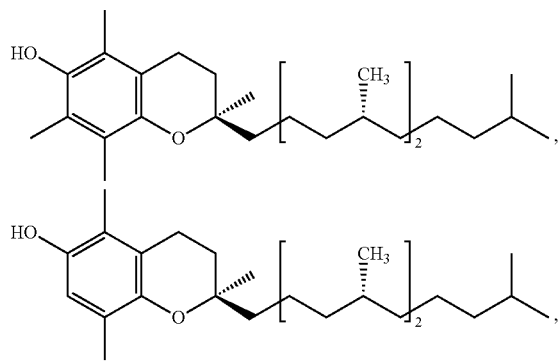

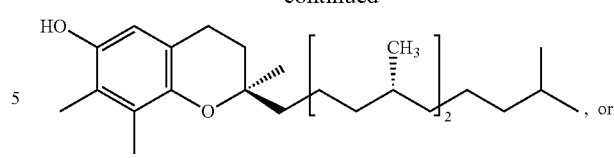

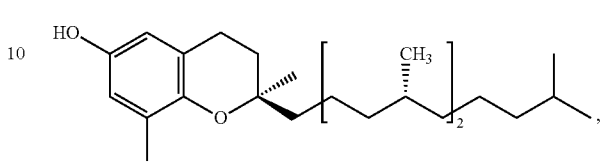

or a combination thereof;

Compound D having the formula of

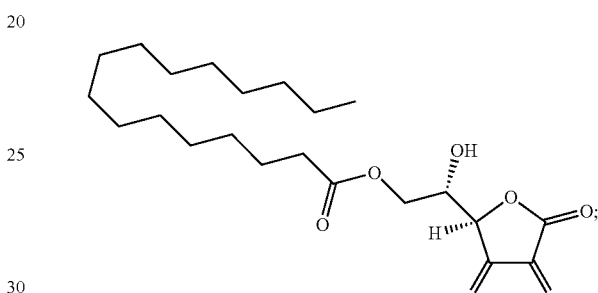

and a solvent having the formula of

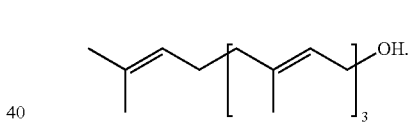

130. The composition of embodiment 26, wherein the composition comprises:

the compound of Formula III or Formula VI having the formula of

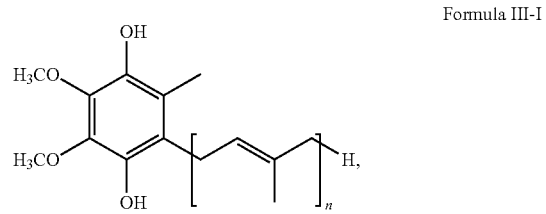

-continued

Formula III-III

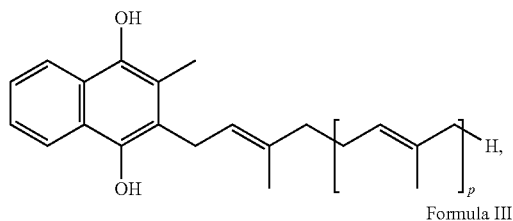

Formula III-IV

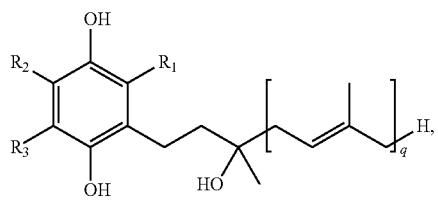

Formula III-V

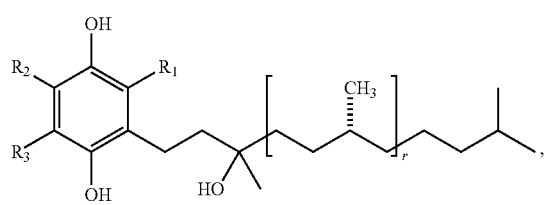

Formula VI-I

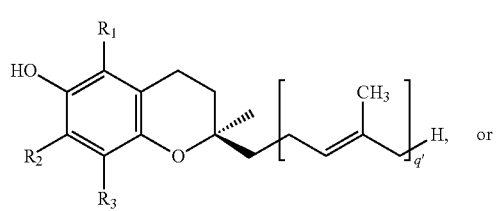

Formula VI-II

[structure]

or a combination thereof;

Compound D of Formula IV having the formula of

Formula IV-I

[structure]

and
the solvent having the formula of

Formula V

[structure]

131. The composition of embodiment 26, wherein the composition comprises:

the compound of Formula III having the formula of

Formula III-I

[structure]

the compound of Formula IV having the formula of

Formula IV-I

[structure]

and
the solvent having the formula of

Formula V

[structure]

132. The composition of embodiment 131, wherein n is 10.
133. The composition of embodiment 132, wherein m is 3.
134. A composition comprising:
a compound having the formula of

[structure]

a compound having the formula of

[structure]

and
a solvent having the formula of

[structure]

135. The composition of embodiment 26, wherein the composition comprises:
the compound of Formula III having the formula of

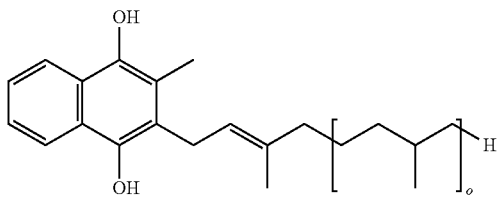

Formula III-II;
the compound of Formula IV having the formula of

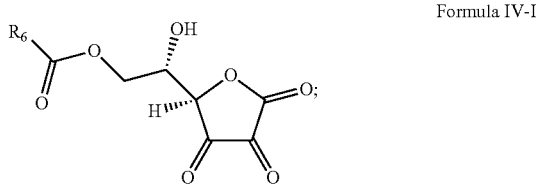

Formula IV-I and
the solvent having the formula of

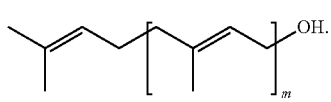

Formula V

136. The composition of embodiment 135, wherein o is 3.
137. The composition of embodiment 136, wherein m is 3.
138. A composition comprising:
a compound having the formula of

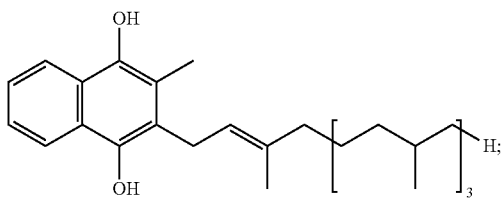

a compound having the formula of

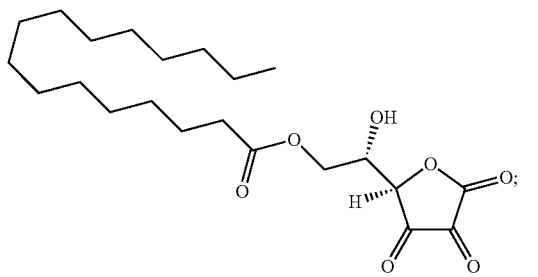 [SMILES: CCCCCCCCCCCCCCCC(=O)OC[C@H](O)[C@H]1OC(=O)C(=O)C1=O]

and
a solvent having the formula of

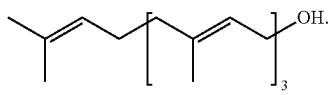

139. The composition of embodiment 26, wherein the composition comprises:
the compound of Formula III having the formula of

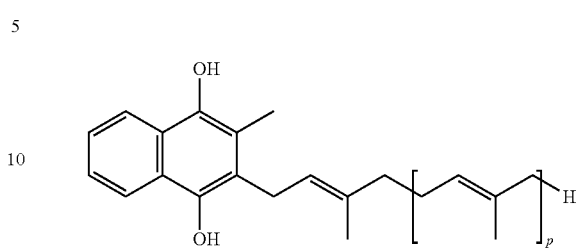

Formula III-III;
the compound of Formula IV having the formula of

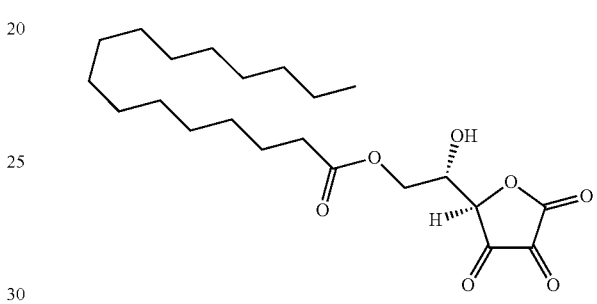

Formula IV-I; and
the solvent having the formula of

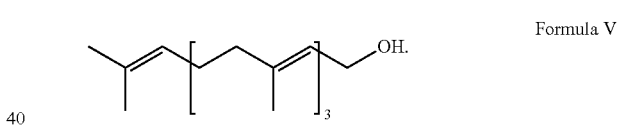

Formula V

140. The composition of embodiment 139, wherein p is 3 or 6.
141. The composition of embodiment 140, wherein m is 3.
142. A composition comprising:
a compound of Formula III having the formula of

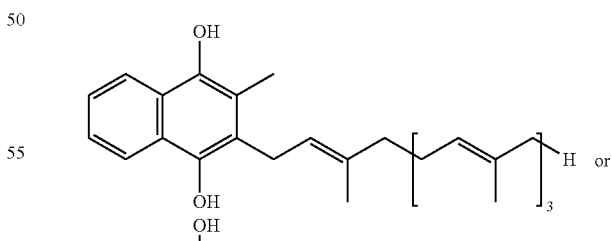

or

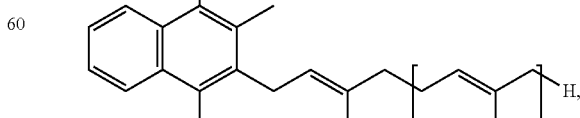

or a combination thereof;

85

Compound D having the formula of

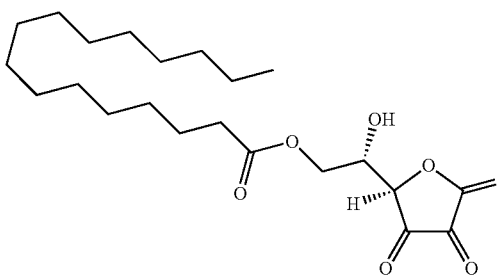

and
a solvent having the formula of

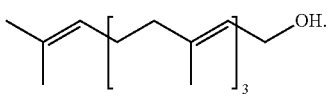

143. The composition of embodiment 26, wherein the composition comprises:
the compound of Formula III having the formula of

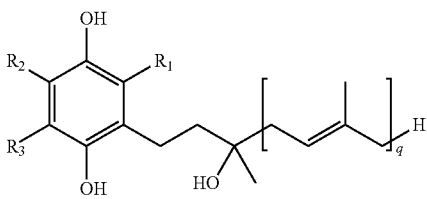

III-IV Formula
the compound of Formula IV having the formula of

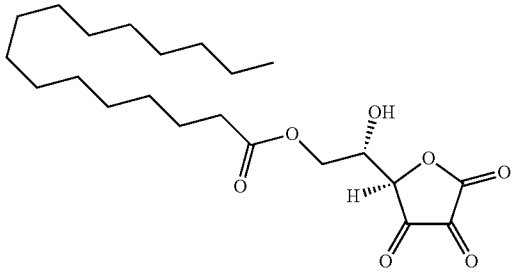 [SMILES: CCCCCCCCCCCCCCCC(=O)OC[C@H](O)[C@H]1OC(=O)C(=O)C1=O]

Formula IV-I, or a combination thereof; and
the solvent having the formula of

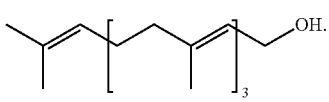

144. The composition of embodiment 143, wherein q is 3.
145. The composition of embodiment 144, wherein m is 3.

86

146. A composition comprising:
a compound having the formula of

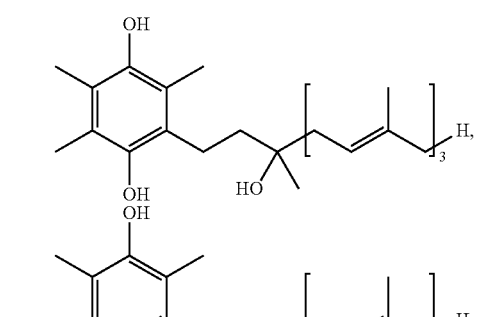

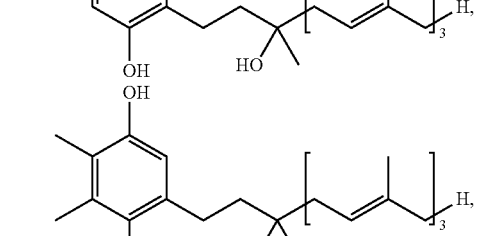

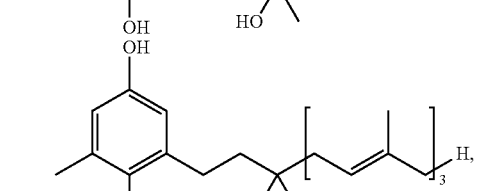

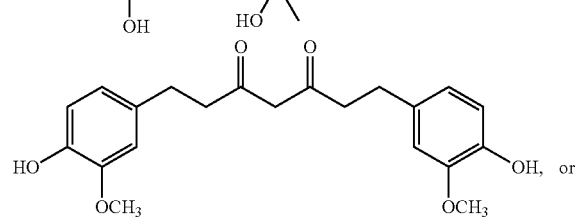

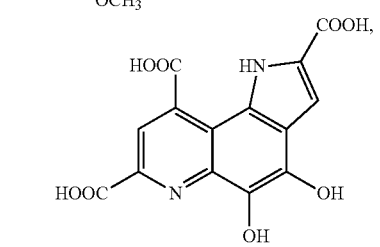

or a combination thereof;
a compound having the formula of

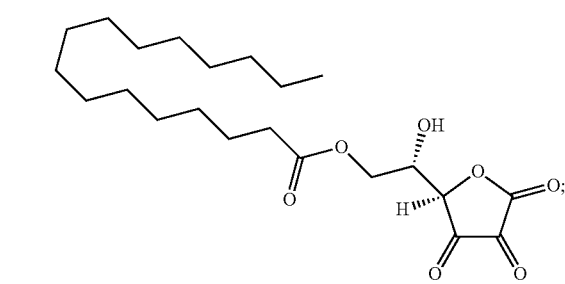 [SMILES: CCCCCCCCCCCCCCCC(=O)OC[C@H](O)[C@H]1OC(=O)C(=O)C1=O]

and a solvent having the formula of

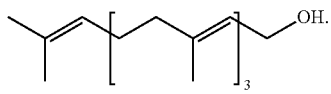

147. The composition of embodiment 26, wherein the composition comprises:
the compound of Formula III having the formula

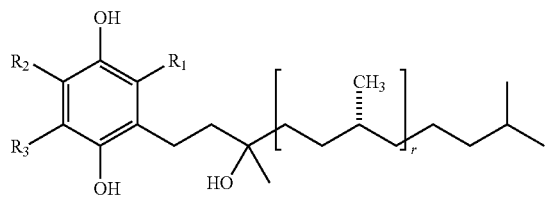

Formula III-V;
the compound of Formula IV having the formula of

Formula IV-I

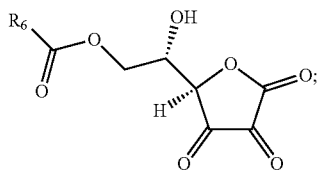

and
the solvent having the formula of

Formula V

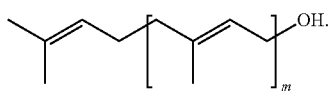

148. The composition of embodiment 147, wherein r is 2.
149. The composition of embodiment 148, wherein m is 3.
150. A composition comprising:
a compound having the formula of

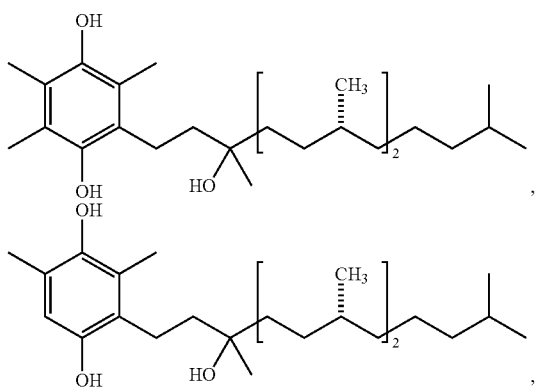

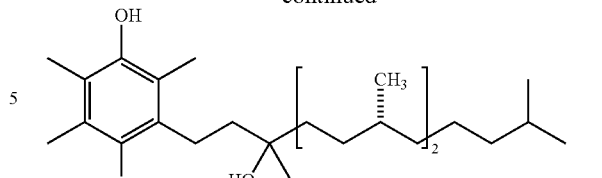

, or

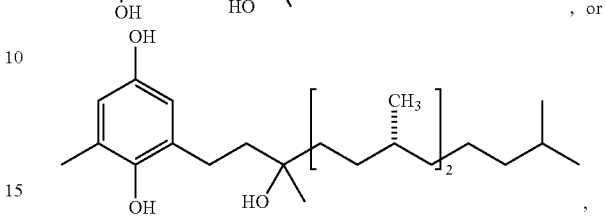

, or combinations thereof;
Compound D having the formula of

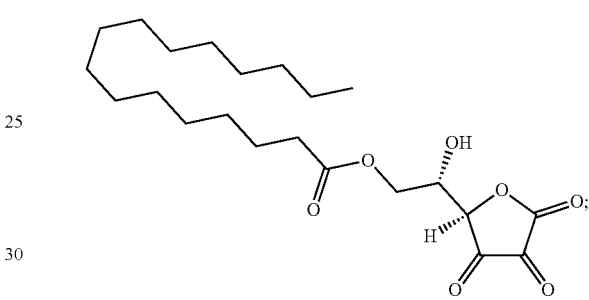

and
a solvent having the formula of

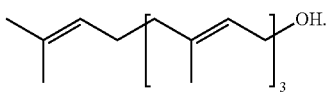

151. The composition of embodiment 26, wherein the composition comprises:
the compound of Formula VI having the formula of Formula VI-I

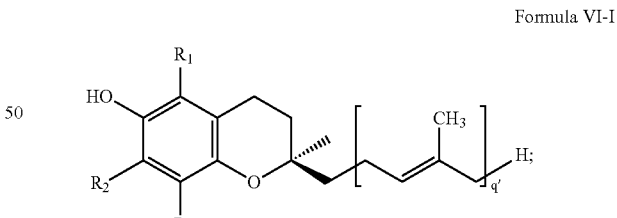

the compound of Formula IV having the formula of

Formula IV-I

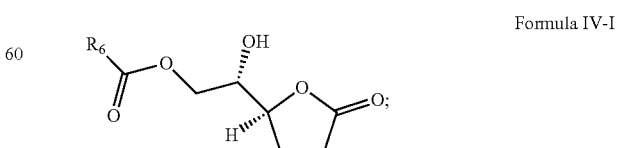

and the solvent having the formula of

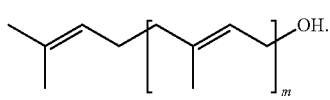
Formula V

152. The composition of embodiment 151, wherein q' is 3.
153. The composition of embodiment 152, wherein m is 3.
154. A composition comprising:
a compound having the formula of

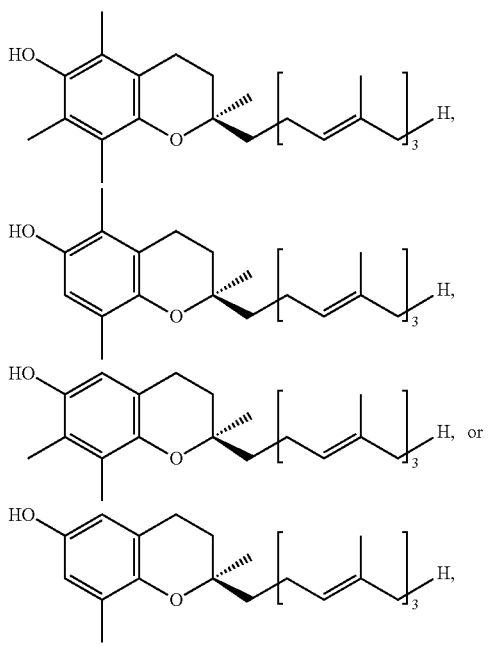

or a combination thereof;
a compound having the formula of

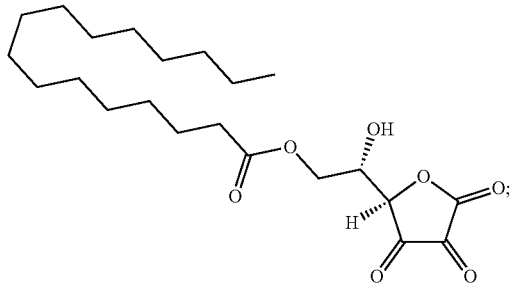 [SMILES: CCCCCCCCCCCCCCCC(=O)OC[C@H](O)[C@H]1OC(=O)C(=O)C1=O]

and
a solvent having the formula of

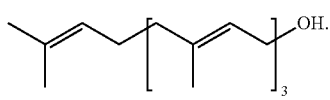

155. The composition of embodiment 26, wherein the composition comprises:

the compound of Formula VI having the formula

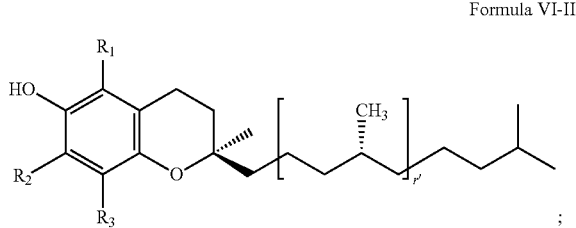
Formula VI-II the compound having the formula of

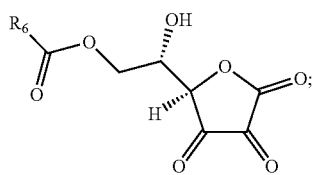
Formula IV-I and
the solvent having the formula of

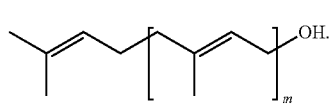
Formula V

156. The composition of embodiment 155, wherein r' is 2.
157. The composition of embodiment 156, wherein m is 3.
158. A composition comprising:
a compound having the formula of

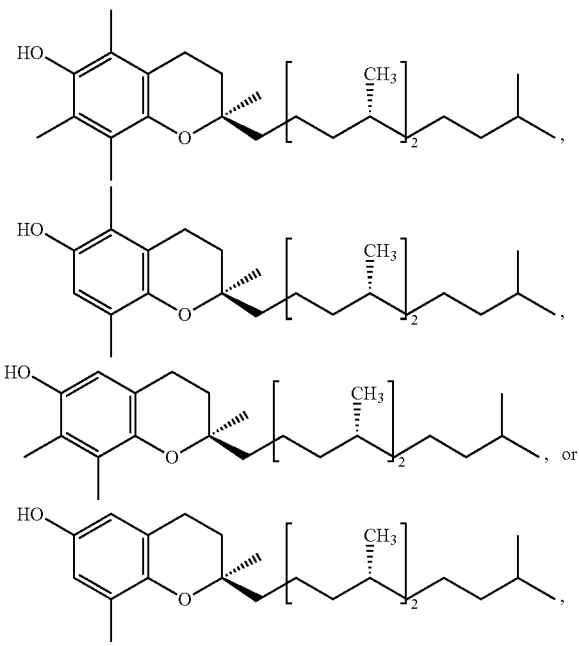

or a combination thereof;

a compound having the formula of

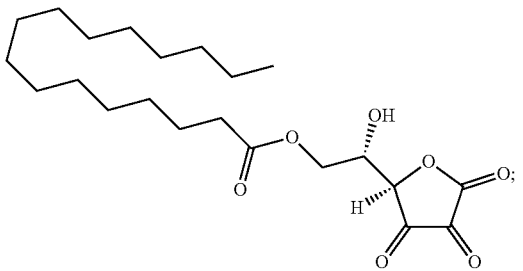 [SMILES: CCCCCCCCCCCCCCCC(=O)OC[C@H](O)[C@H]1OC(=O)C(=O)C1=O]

and
a solvent having the formula of

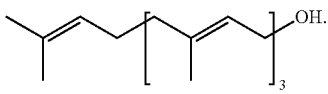

159. The compositions of any one of embodiments 24, 25, and 27-129, or the method of any one of embodiments 1-23, wherein The total amount of Compound A and Compound C is present in an amount of about 1 wt. % to about 80 wt. %.

160. The compositions of embodiment 159, wherein the total amount of Compound A and Compound C is present in an amount of about 20 wt. % to about 60 wt. %.

161. The compositions of embodiment 160, wherein the total amount of Compound A and Compound C is present in an amount of about 33 wt. % to about 42 wt. %.

162. The compositions of any one of embodiments 24, 25, and 27-129, or the method of any one of embodiments 1-23, wherein Compound B is present in an amount of about 1 wt. % to about 40 wt. %.

163. The compositions of embodiment 162, wherein Compound B is present in an amount of about 5 wt. % to about 30 wt. %.

164. The compositions of embodiment 163, wherein Compound B is present in an amount of about 10 wt. % to about 25 wt. %.

165. The compositions of any one of embodiments 159-164, wherein the solvent is present in an amount of about 10 wt. % to about 50 wt. %.

166. The compositions of embodiment 165, wherein the solvent is present in an amount of about 20 wt. % to about 45 wt. %.

167. The compositions of embodiment 166, wherein the solvent is present in an amount of about 30 wt. % to about 40 wt. %.

168. The compositions of any one of embodiments 159-164, wherein the weight ratio of Compound A: the solvent is in a range of about 99.9:0.1 to about 0.1:99.9.

169. The compositions of embodiment 168, wherein the weight ratio of the total amount of Compound A and Compound C: the solvent is in a range of about 5:1 to about 1:5.

170. The compositions of any one of embodiments 24, 25, and 27-129, or the method of any one of embodiments 1-23, wherein the weight ratio of the total amount of Compound A and Compound C:Compound B is in a range of about 5:1 to about 1:5.

171. The compositions of embodiment 170, wherein the weight ratio of the total amount of Compound A and Compound C:Compound B is in a range of about 3:1 to about 1:3, preferable 4:2.

172. The compositions of embodiment 171, wherein the weight ratio of the total amount of Compound A and Compound C:Compound B is in a range of about 2:1 to about 1:2.

173. The compositions of any one of embodiments 25, 27-79, and 101-129, wherein the weight ratio of Compound A:Compound C is in a range of about 99.9:0.1 to about 0.1:99.9.

174. The compositions of embodiment 173, wherein the weight ratio of Compound A:Compound C is in a range of about 40:60 to about 1:99.

175. The compositions of embodiment 174, wherein the weight ratio of Compound A:Compound C is in a range of about 20:80 to about 1:99, about 20:80 to about 2:98, about 20:80 to about 3:97, about 20:80 to about 4:96, about 20:80 to about 15:95, about 20:80 to about 6:94, about 20:80 to about 7:93, about 20:80 to about 8:92, about 20:80 to about 9:91, about 15:85 to about 2:98, about 15:85 to about 3:97, about 15:85 to about 4:96, about 15:85 to about 15:95, about 15:85 to about 6:94, about 15:85 to about 7:93, about 15:85 to about 8:92, about 15:85 to about 9:91, about 13:87 to about 2:98, about 13:87 to about 3:97, about 13:87 to about 4:96, about 13:87 to about 15:95, about 13:87 to about 6:94, about 13:87 to about 7:93, about 13:87 to about 8:92, or about 13:87 to about 9:91.

176. The compositions of embodiment 175, wherein the weight ratio of Compound A:Compound C is in a range of about 10:90 to about 1:99, about 10:90 to about 2:98, about 10:90 to about 3:97, about 10:90 to about 4:96, about 10:90 to about 15:95, about 10:90 to about 6:94, about 10:90 to about 7:93, about 10:90 to about 8:92, or about 10:90 to about 9:91.

177. The compositions of any one of embodiments 25, 27-79, and 101-129, wherein the weight ratio of Compound B:Compound C is in a range of about 99.9:0.1 to about 0.1:99.9.

178. The compositions of embodiment 177, wherein the weight ratio of Compound B:Compound C is in a range of about 40:60 to about 1:99.

179. The compositions of embodiment 178, wherein the weight ratio of Compound B:Compound C is in a range of about 20:80 to about 1:99.

180. The compositions of embodiment 179, wherein the weight ratio of Compound B:Compound C is in a range of about 10:90 to about 1:99.

181. The composition of any one of embodiments 24-180, the composition further comprises an antioxidant in an effective amount to reduce or prevent the oxidation of the compound for Formula III or Formula VI.

182. The composition of embodiment 181, wherein the antioxidant is α-tocopherol, β-tocopherol, γ-tocopherol, δ-tocopherol, α-tocotrienol, β-tocotrienol, γ-tocotrienol, δ-tocotrienol, or glutathione, or a combination thereof.

183. The composition of any one of embodiments 24-182, wherein the composition further comprises vitamin B6.

184. The composition of embodiment 183, wherein the composition comprises

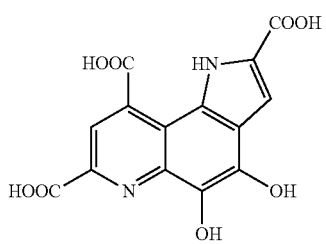 [SMILES: O=C(O)c1cc(C(=O)O)c2c(n1)c(O)c(O)c1cc(C(=O)O)[nH]c12]

and vitamin B6.

185. The composition prepared by the method of any one of embodiments 1-12 and 15-23 or comprising a compound prepared by the method of any one of embodiments 13-14, or a composition of any one of embodiments 24-184, wherein the composition is formulated in a form suitable for oral consumption or oral administration.

186. The composition of embodiment 185, wherein the form is a softgel, a capsule, 2-piece liquid-filled capsule, a bar, confectionary, chocolate, a powder, an oral suspension, a tablet, a pill, a hard-shell, a truffle, a ganache, a truffle ganache, a gum, or a chewable form.

187. The composition of embodiment 186, wherein the form is a softgel.

188. The composition of any one of embodiments 185-187, wherein the composition is formulated directly without any purification, isolation, crystallization or desolvenization.

189. A method of mitigating or treating statin-induced CoQ10 diseases comprising administering to a subject who has been treated with a statin a composition of any one of embodiments 24-37, 80-84, 101-105, 130-134, 159-184 and 185-188, a composition prepared by the method of any one of embodiments 1-12 and 15-23, or a composition comprising a compound prepared by the method of any one of embodiments 13-14.

190. A method of improving cardiac functions, increasing energy, increasing bone mineralization, prevention of joint osteophyte growth prevention and reversion of gall and kidney stones, reversal of arterial calcification, preventing statin-induced myopathy, preventing blood-thinning med-induced dementia, increasing myogenesis, preventing sarcopenia, preventing cancer-induced cachexia, increasing zest and thrive, preventing fibromyalgia, decreasing fatigue, preventing energy deficits, or improving general metabolic synthesis of proteins, CoQ10, or Vitamin K2 comprising administering to a subject a composition of any one of embodiments 24-184 and 185-188, or a composition prepared by the method of any one of embodiments 1-12 and 15-23, or a composition comprising a compound prepared by the method of any one of embodiments 13-14.

191. A method of increasing bioavailability and bioaccessibility of comprising administering to a subject a composition of any one of embodiments 24-184 and 185-188, or a composition prepared by the method of any one of embodiments 1-12 and 15-23, or a composition comprising a compound prepared by the method of any one of embodiments 13-14.

192. A method of increasing absorption into a endothelial or internal surface skin of a dermatological composition, comprising administering to a subject a dermatological composition comprising a composition of any one of embodiments 24-184 and 185-188, or a composition prepared by the method of any one of embodiments 1-12 and 15-23, or a composition comprising a compound prepared by the method of any one of embodiments 13-14.

193. The method of embodiment 192, wherein the method increases the efficacy of the dermatological composition, wherein the method reduces soft and/or hard tissue calcification.

194. The method of any one of embodiments 189-193, the dermatological composition comprises a compound having the formula of

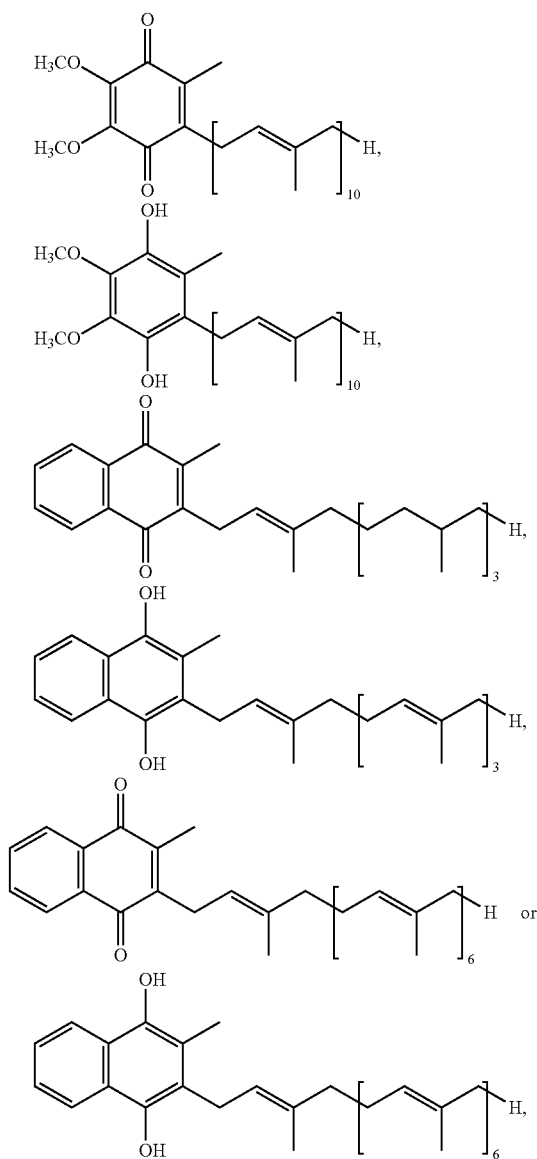

or a salt form thereof.

195. A method of improving mitochondrial function or increasing mitochondrial reproduction comprising administering to a subject a composition of any one of embodiments 24-184 and 185-188, or a composition prepared by the method of any one of embodiments 1-12 and 15-23, or a composition comprising a compound prepared by the method of any one of embodiments 13-14.

196. The method of embodiment 195, the composition comprises a compound or a salt form thereof having the formula of

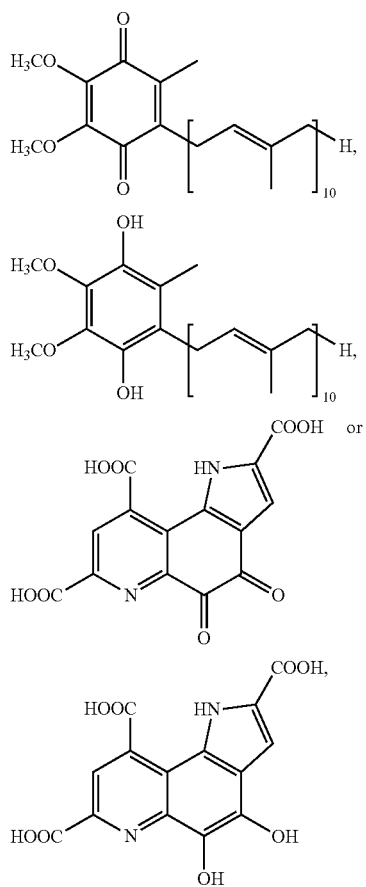

or a combination thereof.

197. A method of improving neurological regeneration comprising administering to a subject a composition of any one of embodiments 24-184 and 185-188, or a composition prepared by the method of any one of embodiments 1-12 and 15-23, or a composition comprising a compound prepared by the method of any one of embodiments 13-14.

198. The method of embodiment 197, the composition comprises a compound or a salt form thereof having the formula of

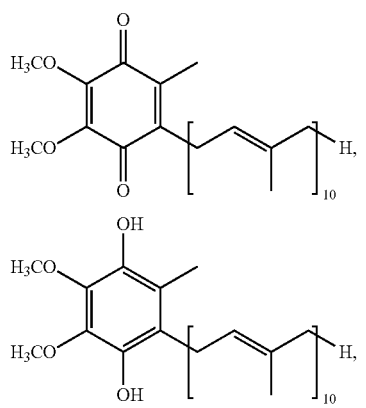

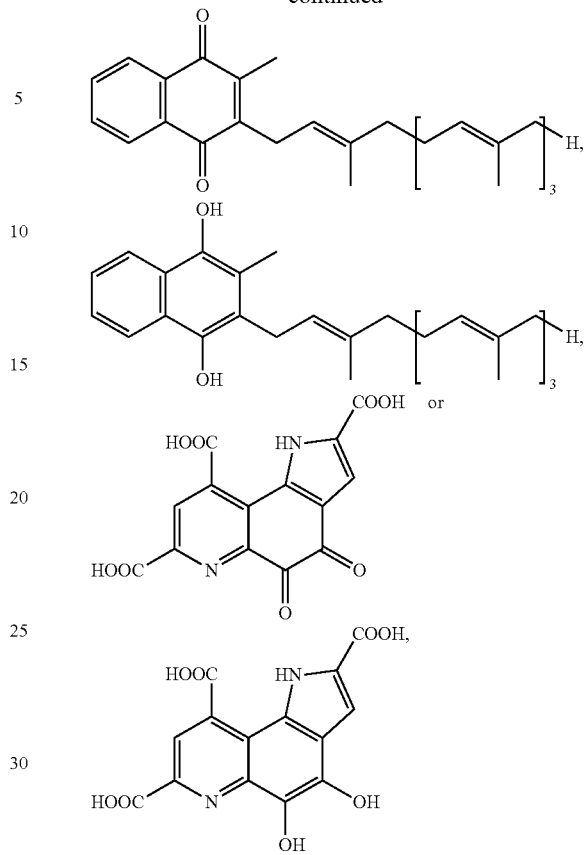

or a combination thereof.

199. A method of mitigating or treating nonalcoholic fatty liver comprising administering to a subject a composition of any one of embodiments 24-184 and 185-188, or a composition prepared by the method of any one of embodiments 1-12 and 15-23, or a composition comprising a compound prepared by the method of any one of embodiments 13-14.

200. The method of embodiment 199, wherein the method comprises reducing liver inflammation or improving liver recovery in congestive and fatty hepatic disease.

201. The method of any one of embodiments 199-200, the composition comprises a compound or a salt form thereof having the formula of

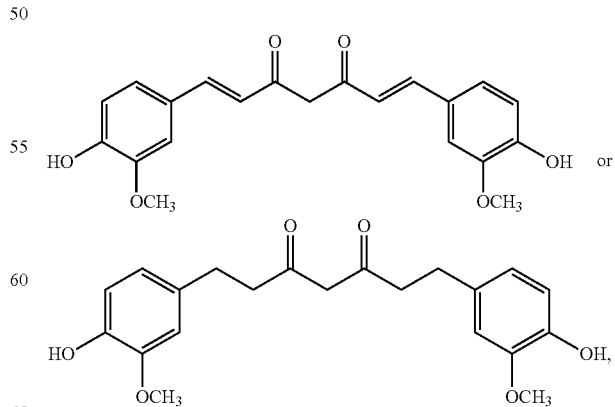

or a combination thereof.

202. The method of any one of embodiments 189-201, wherein the subject is a subject in need thereof.
203. A composition of any one of embodiments 24-37, 80-84, 101-105, 130-134, 159-184 and 185-188 or a composition prepared by the method of any one of embodiments 1-12 and 15-23 or comprising a compound prepared by the method of any one of embodiments 13-14 for use in mitigating or treating statin-induced CoQ10 diseases in a subject, wherein the use comprises administering the composition to the subject.
204. Use of the composition of any one of embodiments 24-37, 80-84, 101-105, 130-134, 159-184 and 185-188 or a composition prepared by the method of any one of embodiments 1-12 and 15-23 or comprising a compound prepared by the method of any one of embodiments 13-14 in the manufacture of a formulation for the treatment of statin-induced CoQ10 diseases in a subject, wherein the use comprises administering the formulation to the subject.
205. A composition of any one of embodiments 24-184 and 185-188 or a composition prepared by the method of any one of embodiments 1-12 and 15-23 or comprising a compound prepared by the method of any one of embodiments 13-14 for use in improving cardiac functions, increasing energy, increasing bone mineralization, prevention of joint osteophyte growth prevention and reversion of gall and kidney stones, reversal of arterial calcification, preventing statin-induced myopathy, preventing blood-thinning med-induced dementia, increasing myogenesis, preventing sarcopenia, preventing cancer-induced cachexia, increasing zest and thrive, preventing fibromyalgia, decreasing fatigue, preventing energy deficits, or improving general metabolic synthesis of proteins, CoQ10, or Vitamin K2 in a subject, wherein the use comprises administering the composition to the subject.
206. Use of a composition of any one of embodiments 24-184 and 185-188 or a composition prepared by the method of any one of embodiments 1-12 and 15-23 or comprising a compound prepared by the method of any one of embodiments 13-14 in the manufacture of a formulation for improving cardiac functions, increasing energy, increasing bone mineralization, prevention of joint osteophyte growth prevention and reversion of gall and kidney stones, reversal of arterial calcification, preventing statin-induced myopathy, preventing blood-thinning med-induced dementia, increasing myogenesis, preventing sarcopenia, preventing cancer-induced cachexia, increasing zest and thrive, preventing fibromyalgia, decreasing fatigue, preventing energy deficits, or improving general metabolic synthesis of proteins, CoQ10, or Vitamin K2 in a subject, wherein the use comprises administering the composition to the subject.
207. A composition of any one of embodiments 24-184 and 185-188 or a composition prepared by the method of any one of embodiments 1-12 and 15-23 or comprising a compound prepared by the method of any one of embodiments 13-14 for use in increasing bioavailability and bioaccessibility in a subject, wherein the use comprises administering the composition to the subject.
208. Use of a composition of any one of embodiments 24-184 and 185-188 or a composition prepared by the method of any one of embodiments 1-12 and 15-23 or comprising a compound prepared by the method of any one of embodiments 13-14 in the manufacture of a formulation for increasing bioavailability and bioaccessibility in a subject, wherein the use comprises administering the composition to the subject.
209. A composition of any one of embodiments 24-184 and 185-188 or a composition prepared by the method of any one of embodiments 1-12 and 15-23 or comprising a compound prepared by the method of any one of embodiments 13-14 for use in increasing absorption into a endothelial or internal surface skin of a dermatological composition in a subject, wherein the use comprises administering the composition to the subject.
210. Use of a composition of any one of embodiments 24-184 and 185-188 or a composition prepared by the method of any one of embodiments 1-12 and 15-23 or comprising a compound prepared by the method of any one of embodiments 13-14 in the manufacture of a formulation for increasing absorption into a endothelial or internal surface skin of a dermatological composition in a subject, wherein the use comprises administering the composition to the subject.
211. The use of increasing the topical and dermatological efficacy to skin applications of any one of embodiments 209-210, where the method comprises reducing soft and/or hard tissue calcification.
212. The use of any one of embodiments 203-211, the composition comprises a compound having the formula of

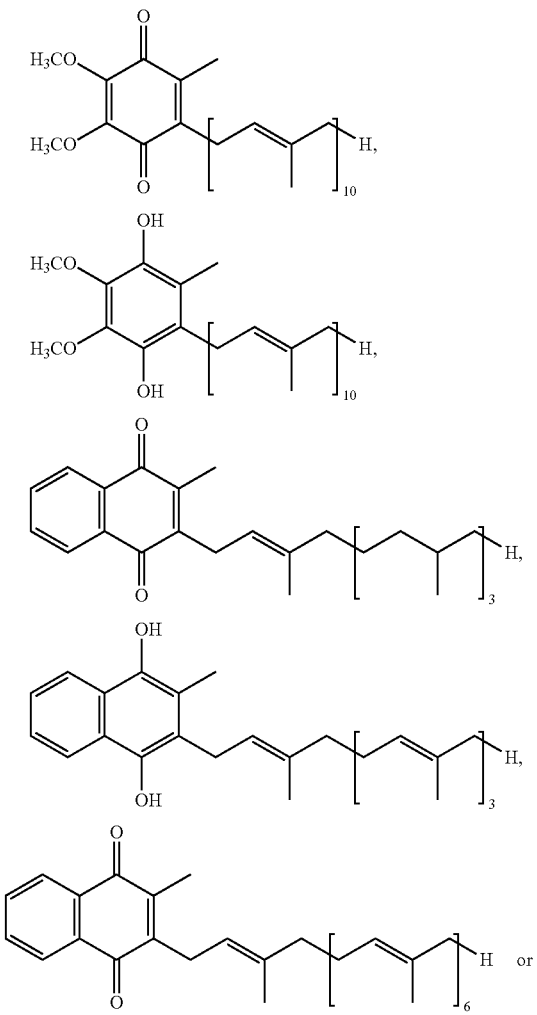

-continued

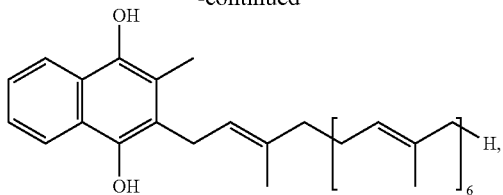

or a salt form thereof.

213. A composition of any one of embodiments 24-184 and 185-188 or a composition prepared by the method of any one of embodiments 1-12 and 15-23 or comprising a compound prepared by the method of any one of embodiments 13-14 for use in improving mitochondrial function or increasing mitochondrial reproduction in a subject, wherein the use comprises administering the composition to the subject.

214. Use of a composition of any one of embodiments 24-184 and 185-188 or a composition prepared by the method of any one of embodiments 1-12 and 15-23 or comprising a compound prepared by the method of any one of embodiments 13-14 in the manufacture of a formulation for improving mitochondrial function or increasing mitochondrial reproduction in a subject, wherein the use comprises administering the composition to the subject.

215. The use of any one of embodiments 213-214, the composition comprises a compound or a salt form thereof having the formula of

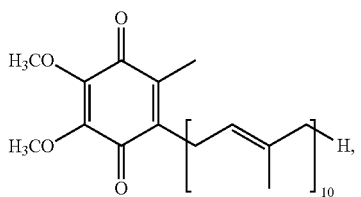

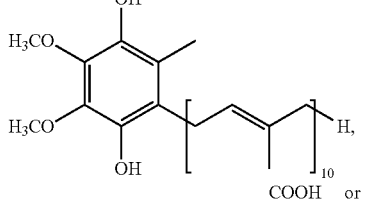

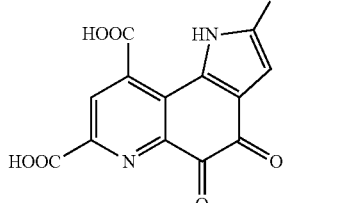

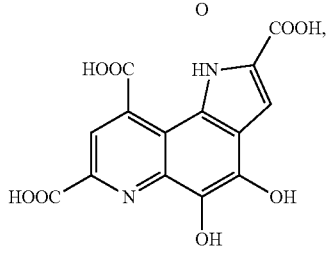

or a combination thereof.

216. A composition of any one of embodiments 24-184 and 185-188 or a composition prepared by the method of any one of embodiments 1-12 and 15-23 or comprising a compound prepared by the method of any one of embodiments 13-14 for use in improving neurological regeneration in a subject, wherein the use comprises administering the composition to the subject.

217. Use of a composition of any one of embodiments 24-184 and 185-188 or a composition prepared by the method of any one of embodiments 1-12 and 15-23 or comprising a compound prepared by the method of any one of embodiments 13-14 in the manufacture of a formulation for improving neurological regeneration in a subject, wherein the use comprises administering the composition to the subject.

218. The use of any one of embodiments 216-217, the composition comprises a compound or a salt form thereof having the formula of

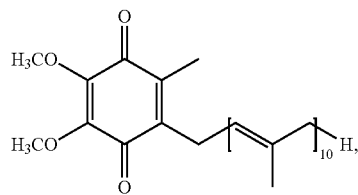

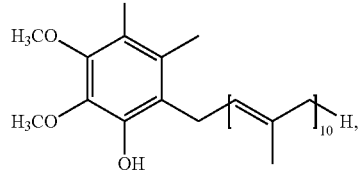

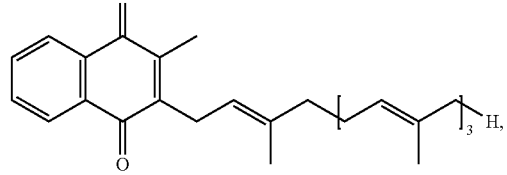

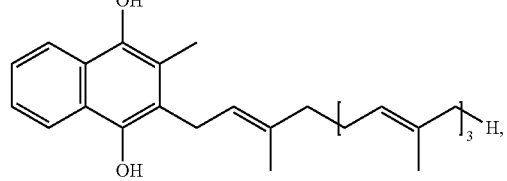

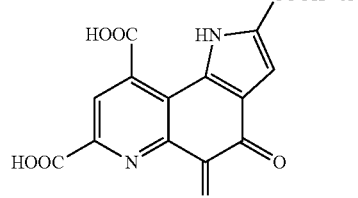

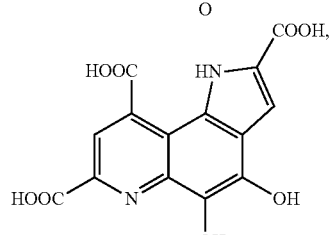

or a combination thereof.

219. A composition of any one of embodiments 24-184 and 185-188 or a composition prepared by the method of any one of embodiments 1-12 and 15-23 or comprising a compound prepared by the method of any one of embodiments 13-14 for use in mitigating nonalcoholic fatty liver in a subject, wherein the use comprises administering the composition to the subject.

220. Use of a composition of any one of embodiments 24-184 and 185-188 or a composition prepared by the method of any one of embodiments 1-12 and 15-23 or comprising a compound prepared by the method of any one of embodiments 13-14 in the manufacture of a formulation for mitigating nonalcoholic fatty liver in a subject, wherein the use comprises administering the composition to the subject.

221. The use of any one of embodiment 219-220, wherein the method comprises reducing inflammation or improving liver recovery in congestive and fatty hepatic disease.

222. The use of any one of embodiments 219-221, the composition comprises a compound or a salt form thereof having the formula of or a combination thereof.

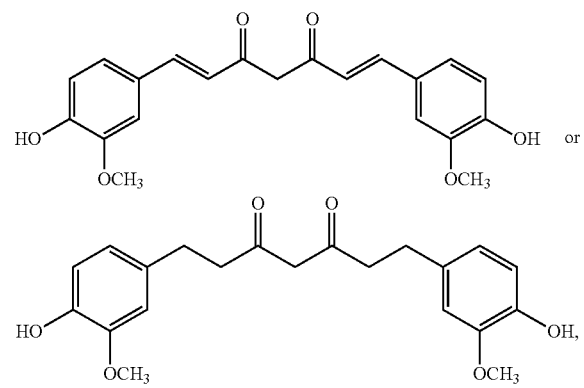

223. The use of any one of embodiments 203-222, wherein the subject is a subject in need thereof.

224. The composition of any one of embodiments 1-223, wherein the composition further comprises an omega-3 fatty acids, also called Omega-3 oils, ω-3 fatty acids or n-3 fatty acids such as are polyunsaturated fatty acids (PUFAs) characterized by the presence of a double bond three atoms away from the terminal methyl group in their chemical structure such as α-linolenic acid (ALA), eicosapentaenoic acid (EPA) and docosahexaenoic acid (DHA).

225. The composition of any one of embodiments 1-224, wherein the composition further comprises a vitamin D, such as vitamin D1 (also known as mixture of molecular compounds of ergocalciferol with lumisterol, 1:1), vitamin D2 (also known as ergocalciferol), vitamin, D3 (also known as cholecalciferol), vitamin D4 (also known as 22-dihydroergocalciferol, and vitamin D5 (also known as sitocalciferol).

226. The composition of any one of embodiments 1-224, wherein the Compound C were prepared from Compound A without using inorganic reducing reagent such as, sodium dithionite, sodium hyposulfite, or zinc in combination with sulfuric acid or any other similar acid.

227. In some embodiments as described herein, compositions comprising a compound having the formula of

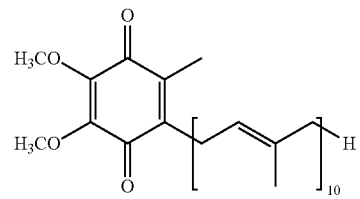

do not comprise a compound having the formula of

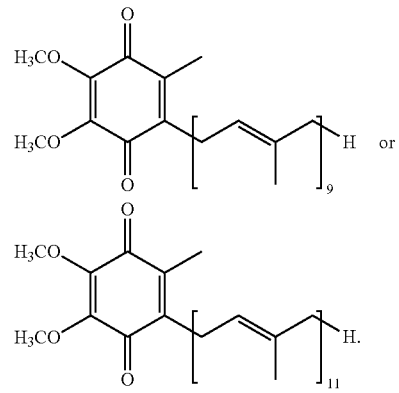

228. In some embodiments as described herein, compositions comprising Compound C having the formula of

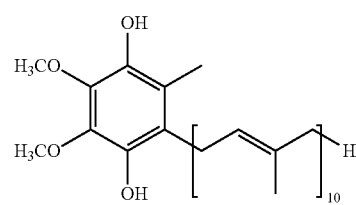

do not comprise a compound having the formula of

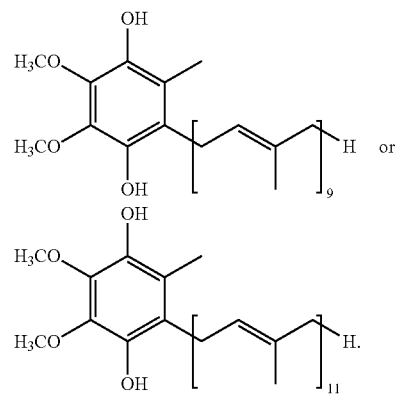

The following examples are illustrative, but not limiting, of compositions, methods of preparation thereof, and methods of use thereof described herein. Other suitable modifications and adaptations of the variety of conditions and parameters normally encountered in therapy, synthesis, and other embodiments disclosed herein are within the spirit and scope of the embodiments provided for herein.

EXAMPLES

Geranylgeraniol (GG) is a diterpene alcohol that is required for the synthesis of CoQ10. GG (CAS 24034-73-9; $C_{20}H_{34}O$; MW-290) is a light liquid that has four repeating isoprenyl units. At least two GG molecules are embedded in the side-chain of a CoQ10 molecule. While plants, insects and mammals produce GG, only mammals (particularly humans) utilize GG for the synthesis of CoQ10. Therefore, GG has an implicit endogenous usage for the biosynthesis of CoQ10.

The discovery of GG for the synthesis of Vitamin E (in plants) has been known; however, the discovery of GG for the synthesis of vitamins K2 (in mammals) is a recent advent (Nakagawa, et al., 2010; Nickerson, et al., 2013; Hirota, et al., 2015; Al Rajabi, et al., 2012; Harshman, et al., 2019). The vitamin K2 series of compounds—also known as menaquinones—are understood as fermentation products of microbial origin that require exogenous plant-derived vitamin K1 (phylloquinone). These fermentation-converted menaquinones have typical 7 to 13 isoprenyl units, designated as MK7, MK8, and so forth. These menaquinones are found in fermented foods and are also produced in the human gastrointestinal (GI) tract. The bioavailability of these fermentation-derived menaquinones to our bodies was not well understood since the mouth-to-anus alimentary canal is not considered "inside" our body. However, MK4 (for which the entire 4 isoprenyl side-chain comes from endogenously supplied intact GG) is a biosynthesized product within the body (e.g. in the kidney, liver, brain).

Figure 2:
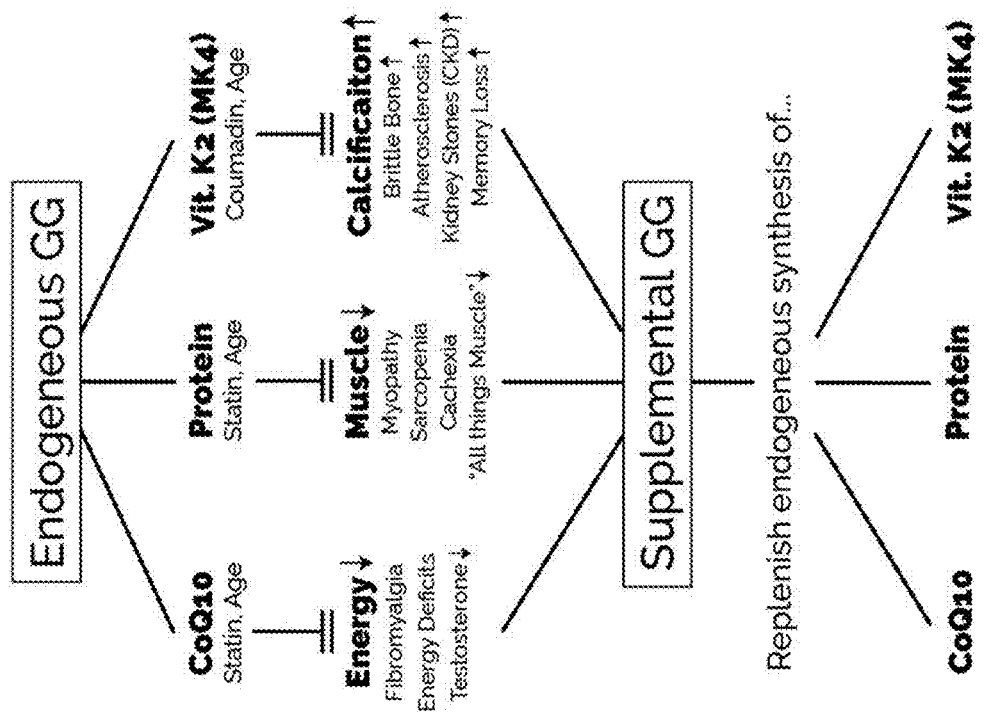
FIG. 2: Utility of GG in systemic protein synthesis from Marcuzzi et al. and Campia, et al. (International journal of molecular sciences. 2016; 17(3):365; British journal of pharmacology. 2009, 158(7):1777-86).

The utility of GG for myogenesis is well known, responsible for systemic protein synthesis (Marcuzzi, et al., 2016; Campia, et al., 2009). GG is neither an amino acid nor a peptide but it is a prosthetic agent or arm for protein synthesis. This is a "global" biochemical event in the body because 80% of a human 25 k genes are responsible for protein syntheses. Sarcopenia (age-induced), myopathy (med-induced), cachexia (cancer patients), muscular diseases and dystrophies, testosterone-depleted muscle growth are related to GG decrease or depletion. Put together, GG is responsible for numerous endogenous syntheses—CoQ10, MK4, protein—such that supplemental GG will bring essential nutrient replenishment and thereby support growth in a person. CoQnol has been designated as "ubiquinol" but it is accurate that GG is the true "ubiquitous alcohol." See FIG. 2.

It is desired that CoQone be reduced to the active CoQnol. However, CoQnol is unstable in oxygen-rich environments and readily oxidized back to CoQone. Removal of oxygen by nitrogen is often employed. However, nitrogen is lighter than air and may escape the reaction vessel. Additionally, nitrogen is not completely inert. Noble gases—which are by definition inert—may be used. Of these noble gases, only argon, krypton and xenon are heavier than air. For reduction to occur, it is desirable to use nitrogen (for continuous headspace displacement) and argon (for static headspace displacement). These are suitable examples of gases to assist in the reduction of CoQone and to prevent CoQnol from oxidation. Surprisingly and unexpectedly, the use of argon (heavier than air) for headspace displacement was not employed in softgel or hard-shell encapsulation.

CoQone is a powder and needed to be in a soluble medium to allow physical contact with a lipid reductant for reduction to occur. A known lipid reductant (reducing agent) is ascorbyl palmitate (AP) or Vitamin C palmitate. However, CoQone is exceedingly difficult to solubilize much less, dissolve. Different strategies were disclosed to solubilize CoQone. To date successful solubilizer ingredients dilute CoQone 7-50× such that excipients often contribute ≥85% of fill weight. This renders CoQ10 in softgels of about 2-15% potency, meaning a softgel of 1000-1200 mg (Oblong 20 size) fill weight may typically contain 20-100 mg CoQ10. This dilution is disadvantageous and presents a barrier to CoQ10 potency and efficacy. For example, in the best case scenario, an unacceptably large consumption of 3 or 4 softgels (Oblong 20) are required to deliver a 100-300 mg/d CoQ10 that concomitantly requires the consumption of enormous (2-5 g/d of mainly synthetic) fillers and excipients.

This example of solubilization strategy involves copious amount of fillers and/or excipients as summarized below (Chopra, 8,753,675; Goldman, 6,056,971).
  a) surfactant emulsifiers (polysorbates, complex esters, ester-ethers, etc.)
  b) polyol solvents (glycerin, propylene glycol, etc.)
  c) disruptors to CoQ10 crystallization (beeswax)
  d) glyceride diluents (MG, DG, TG; popularly MCT)
  e) monoterpene solubilizers (monoterpenes; as in limonene)
  f) antioxidants (AT, mixed Ts, T3s, rosemary oil)

The sole intent of applying fillers and excipients is to present the hard-to-solubilize CoQ10 into solution. These strategies are impractical because of the heavy usage of fillers and excipients that afforded a mere 2-15% CoQone concentration. It is further questionable that solubilization is effected, crystallization is disrupted, and oxidation is arrested (Passwater, March 2019; Passwater, April 2019). At best, these processes are partial with a large concomitant addition (>85%) of exogenous materials.

The desire to obtain CoQnol comes from this reduced state of CoQ10 being utilized as the in vivo co-enzyme responsible for cellular energy production described earlier. CoQnol is well-embedded in the lipid-membranes of the organelle mitochondria where ATP energy is manufactured.

Further, it is known that CoQnol is a powerful biomembrane lipid antioxidant and work synergistically with vitamin E (tocopherols and tocotrienols). Together these lipid antioxidants can be recycled by vitamin C ascorbate.

However, CoQnol is unstable and readily converted back to the oxidized CoQone in the presence of air or oxygen and this was well studied for about 25 years (Roginsky, et al., 1996). This paper provided the following knowledge.
  a) CoQone can be reduced by ascorbate to CoQnol
  b) 10-15% reduction may happen with "moderate" oxygen
  c) 50-90% reduction may happen with the absence (or near absence) of oxygen
  d) Extent of CoQone reduction is controlled by oxygen
  e) Physical availability of CoQone to ascorbate is important for reduction This study was performed with the intention to emulate physiologic conditions of GI tract (pH 7.4, 37.0+/−1.5 C) in an oxygen-rich environment. What this paper did not address was the non-physiologic lipid medium (meaning the absence of pH activity) or the non-physiologic elevated temperatures. It is further presumed that because of the oxidizability of CoQnol its instability would occur and persist above RT of 22-26 C and even worse above body temperatures of 36-38 C.

Surprisingly and unexpectedly this teaching and presumption of CoQnol instability is limiting and incorrect beyond that of physiology. It does not hold true in inert environment inside a reaction vessel or an encapsulated delivery system like softgels. For example, in the absence of air or oxygen, CoQone conversion to CoQnol can reach 80-95%. The reaction temperatures can be 30-75 C, preferably 40-70 C, more preferably 50-65 C. The present invention teaches that elevated temperatures are to be employed for the reduction of CoQone. This present invention is contrarian to the teachings of all prior art.

This invention is further directed to a highly efficient method of CoQone-to-CoQnol reduction wherein a diterpenoid GG solubilizes and dissolves CoQone and AP, such that two ingredients are in homogenous contact with each other and that the reaction is conducted at elevated temperatures in an inert environment of nitrogen-filled or argon-filled reactor headspace.

A natural compound diterpenoid (C20) may be used to solubilize CoQone and AP without additional excipient or filler. It is known in the art that monoterpenoids (C10) may be used to solubilize CoQ10. However, the diterpenoid GG dissolves both oxidant (CoQone) and reductant (AP), allowing intimate molecular contact of two lipid soluble molecules in a true homogenous solution.

This invention is unique because it combines two hitherto unknown features, namely to allow for the complete dissolution of redox ingredients (CoQone and AP) to provide physical accessibility, and to conduct reaction in elevated temperature under anaerobic condition.

This process allowed for a minimal (4-6 times less) addition of a solubilizer diterpenoid without any fatty acid glycerides (MG, DG, TG, PL, other fatty acid materials), nor emulsifiers nor surfactants or any of the filler/excipient strategies commonly employed. Thus it was possible to increase concentration of the active ingredient CoQ10 by about 10-fold to 20-fold.

It was disclosed in a prior art (Fantuzzi 8,124,072) that CoQ10 was solubilized in monoterpenes. Because of the weaker solvency of monoterpenes compared to diterpenes, the weight ratio of Terpenoid:CoQ10 is more than 4× higher for limonene than GG to dissolve CoQ10. Surprisingly and unexpectedly diterpenoids are superior to monoterpenoids to dissolve CoQ10 by 4-fold to 6-fold. Further, this patent (U.S. Pat. No. 8,124,072) teaches only CoQ10 dissolution without CoQnol reduction enablement.

In this invention, it is found that a substantially lower amount of AP reductant may be used by 100% or more. Furthermore, it is found that a plant-based diterpenoid GG can efficiently solubilized CoQone such that CoQone concentration increases to 40% or more in the formulation. This means the overall CoQ10 concentration in the softgel may be increased by 10-fold to 20-fold. This feature dramatically allows a converted and stabilized CoQnol at the highest concentration or potency available for encapsulation. Reduction of CoQone to CoQnol was achieved about 85% to about 95% at a typical reaction time of 3-6d. It was further shown that such converted CoQnol remained stable in a hermetically sealed softgel and hard-shell capsules or in any enclosed environment application generally with excluded or minimized air or oxygen.

Example 1: Preparation Compositions by Conversion of CoQone to CoQnol with AP and GG in a Fixed Ratio This example sets forth a composition and a method for converting CoQone to CoQnol by utilizing the reducing properties of AP and the solubilizing properties of GG. The weight ratio of components was kept static throughout the length of this example.

Procedure:
Prepare the following components in their respective weight ratios:
CoQone (about 30-50%)
AP (about 5-40%)
GG (about 30-50%)
GG was added to an appropriately sized mixing vessel and heated to about 52° C. (±3°) while stirring. CoQone was added to the mixing vessel with GG to form a mixture. The mixture was stirred at about 52° C.). (±3° until CoQone was completely melted and solubilized in GG to attain a translucent solution. Then AP was added to the translucent solution, which was stirred until no visible dry AP was left on the surface. The mixing vessel was then flushed with a neutral, non-oxygenated gas until atmospheric air was displaced and the mixing vessel was sealed airtight. This mixture was then stirred at elevated temperature for several days with periodic flushing of neutral, non-oxygenated gas until target conversion rate was achieved.

The final mixture has the following components and ratios (by weight):

| | |
|---|---|
| CoQone | about 40% |
| AP | about 20% |
| GG | about 40% |

The weight ratios of CoQone to CoQnol in the mixture were determined by HPLC using a modified method disclosed by Mattila (Mattila et al., 2000), which is incorporated by reference in its entirety. Samples were extracted from the mixing vessel under inert gas flush and the mixing vessel was then flushed with inert gas prior to resealing. Samples were dissolved in chloroform and then analyzed on a Waters Symmetry $C_{18}$ column (5 μm, 4.6×250 mm) at about 35° C. The mobile phase (1.8 mL/min) was methanol:ethanol:2-propanol (53:25:22) with UV detection at 275 nm for CoQone and 290 nm for CoQnol. The retention times were about 5.7 min for CoQnol and about 8.8 min for CoQone, respectively. The HPLC method described herein was utilized in subsequent examples.

Figure 3:
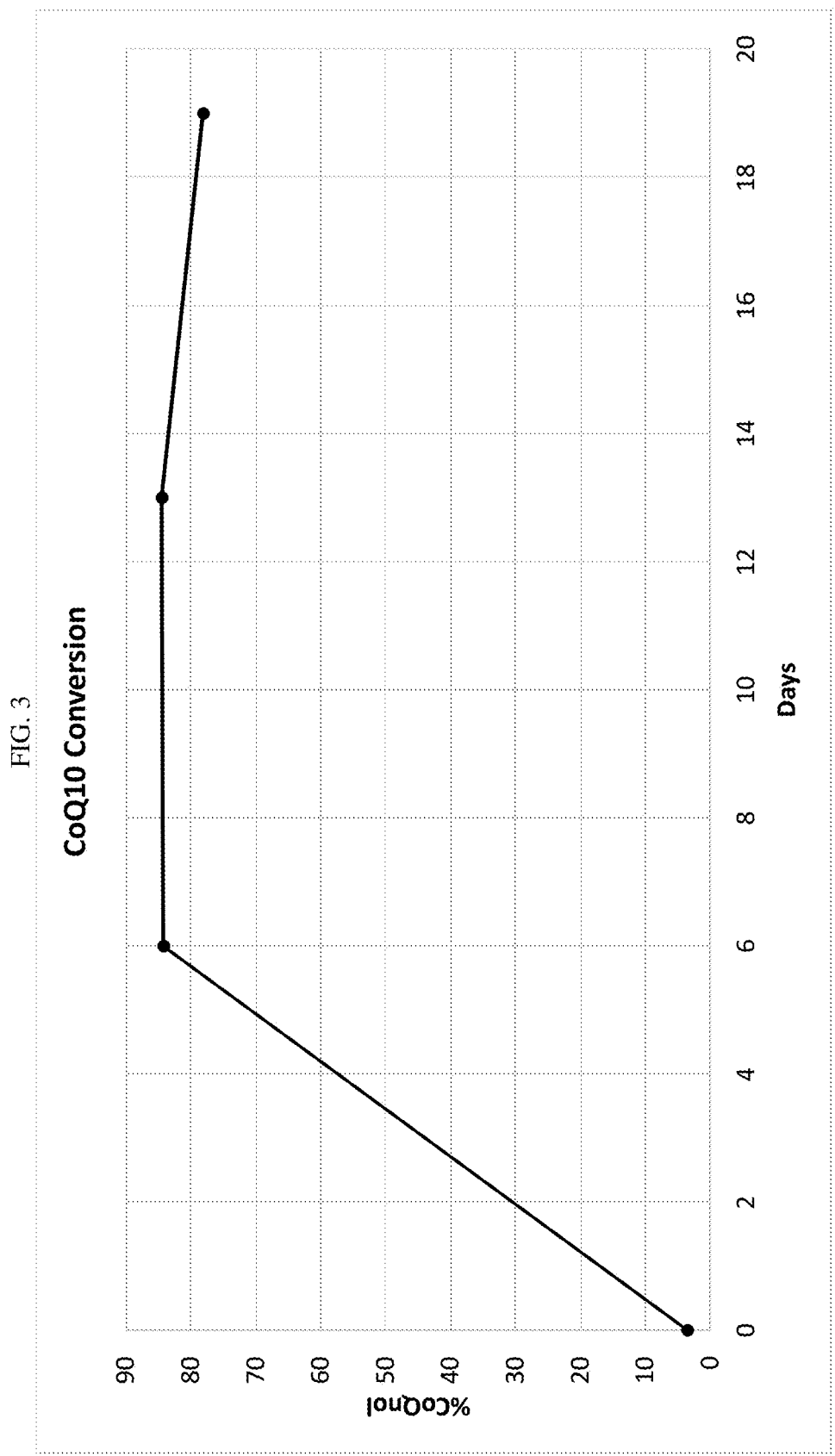
FIG. 3: CoQnol conversion rate over a period of abut 20 days in a fixed CoQ:AP:GG ratio of about 4:2:4

A final conversion rate of about 85% from CoQone to CoQnol was obtained in about 6 to about 13 days and in a fixed CoQ:AP:GG ratio of about 4:2:4 as shown in FIG. 3.

Example 2: Preparation Compositions by Conversion of CoQone to CoQnol with AP and GG in Dynamic Ratios This example sets forth a composition and a method for converting CoQone to CoQnol utilizing the reducing properties of AP and the solubilizing properties of GG. The weight ratio of components was changed during the length of the study.

Procedure:
Prepare the following components in their respective ratio (by weight):
CoQone (about 30-50%)
AP (about 5-40%)
GG (about 30-50%)
GG was added to an appropriately sized mixing vessel and heated to about 52° C. (±3°) while stirring. CoQone was added to the mixing vessel with GG to form a mixture. The mixture was stirred at about 52° C.). (±3° until CoQone was completely melted and solubilized in GG to attain a translucent solution. Then AP was added to the translucent solution, which was stirred until no visible dry AP was left on the surface. The mixing vessel was then flushed with a neutral, non-oxygenated gas until atmospheric air was displaced and the mixing vessel was sealed air-tight. To the mixture were periodically added additional AP, which was then mixed in until no visible dry AP was left and the mixture was flushed with more neutral gas.

This mixture was then stirred at the elevated temperature for several days with periodic flushing of neutral, non-oxygenated gas until target conversion rate was achieved.

The mixture had shown the following weight ratios of CoQone:AP:GG on a daily basis.

| Day 0  | about 4:0.5:4 |
| Day 1  | about 4:0.5:4 |
| Day 2  | about 4:1:4   |
| Day 3  | about 4:1.5:4 |
| Day 4  | about 4:2:4   |
| Day 6  | about 4:2.5:4 |
| Day 7  | about 4:3:4   |
| Day 8  | about 4:3.5:4 |
| Day 9  | about 4:4:4   |
| Day 10 | about 4:4:4   |

Figure 4:
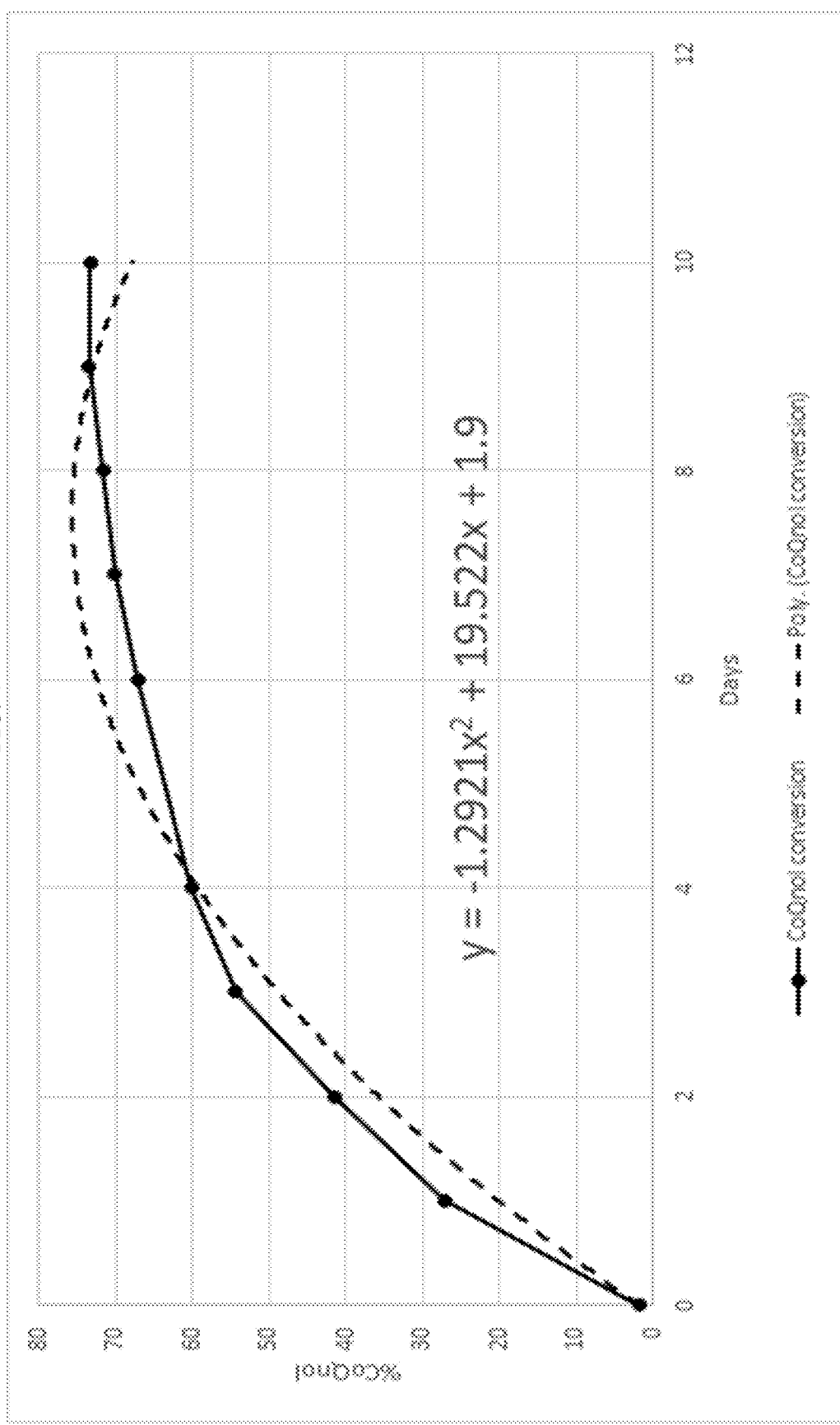
FIG. 4: CoQnol conversion rate over a period of about 10 days with an incremental addition of AP into a fixed ratio of CoQ (both CoQnol and CoQone) to GG.

A final conversion rate of about 75% from CoQone to CoQnol was achieved in about 9-10 days with an incremental addition of AP into a fixed ratio of CoQ (both CoQnol and CoQone) to GG. It was determined that a CoQone:AP:GG ratio may best be shown for CoQnol conversion by AP based on second order polynomial superimposition (dashed line). The polynomial fit suggested a preferable about 3-6 days reaction time for optimal CoQnol reduction, and more preferable about 4 days reaction time (intersection point). This plot showed the further supported a preferable ratio of CoQone:AP:GG ratio is about 4:2:4. See FIG. 4.

Example 3: Stability of CoQ10 at Elevated Temperatures

This example showed that long periods of heating and intermittent exposure to atmospheric oxygen caused controlled degradation of CoQ10 in the formulation comprising AP and GG.

Procedure:
Prepare the following components in their respective ratio amounts:
CoQone (about 30-50%)
AP (about 5-40%)
GG (about 30-50%)
GG was added to an appropriately sized mixing vessel and heated to about 52° C. (±3°) while stirring. CoQone was added to the mixing vessel with GG to form a mixture. The mixture was stirred at about 52° C.). (±3° until CoQone was completely melted and solubilized in GG to attain a translucent solution. Then AP was added to the translucent solution, which was stirred until no visible dry AP was left on the surface. The mixing vessel was then flushed with a neutral, non-oxygenated gas until atmospheric air was displaced and the mixing vessel was sealed airtight. This mixture was then mixed at elevated temperature for 10 days with periodic flushing of neutral, non-oxygenated gas where the CoQnol conversion rate and the total amount of CoQ (both CoQnol and CoQone) were monitored.

The final mixture had the following components and ratios (by weight):

| CoQ | about 33.3% |
| AP  | about 33.3% |
| GG  | about 33.3% |

Figure 5:
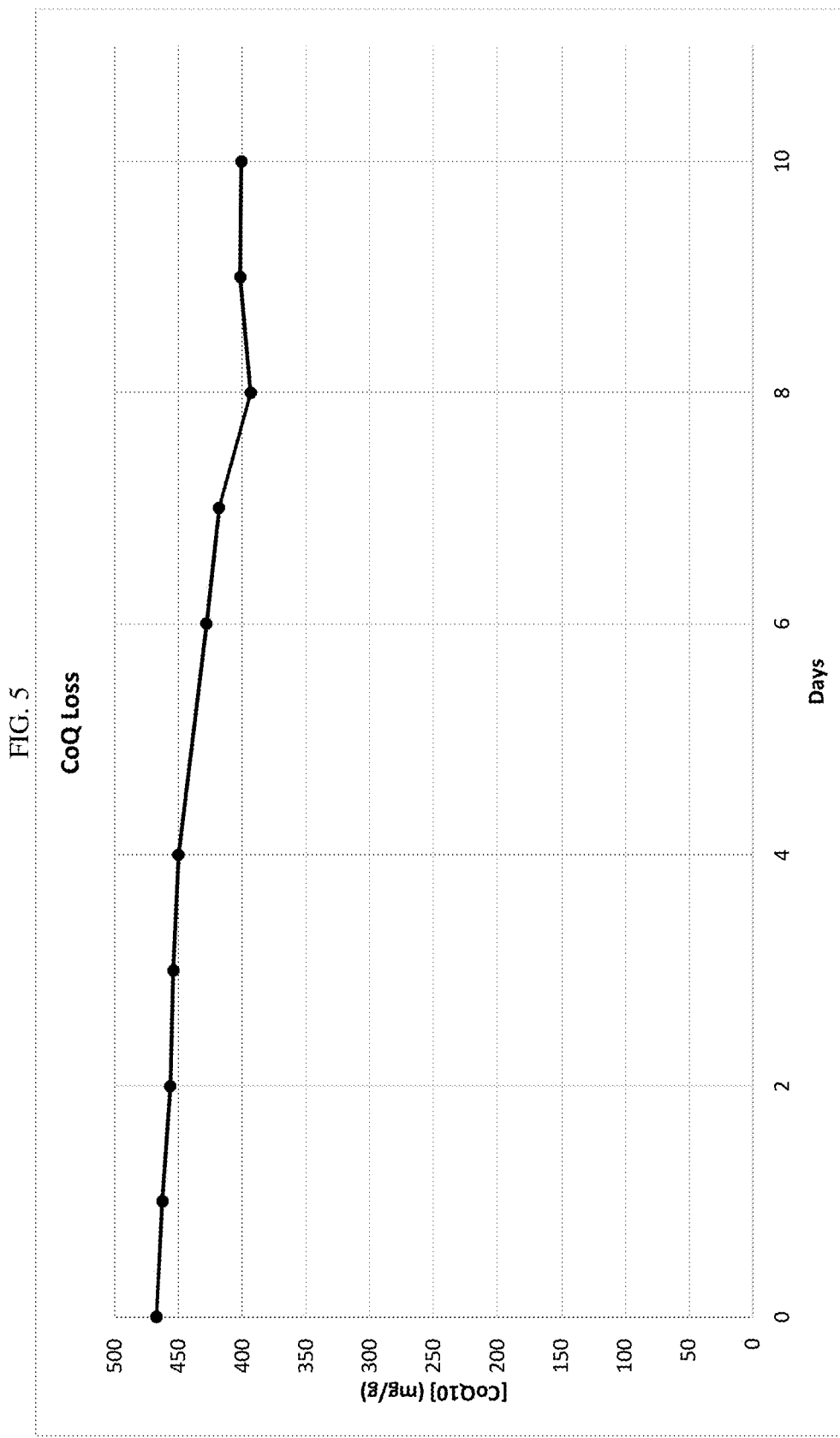
FIG. 5: CoQ loss rate over a period of 10 days at about 50-55° C. in a fixed initial ratio of CoQ:AP:GG at about 1:1:1

The final mixture after the duration of the study had about 15% loss of total CoQ (both CoQone and CoQnol) in about 8-10 days at about 50-55° C. in a fixed initial ratio of CoQ:AP:GG at about 1:1:1. However, there was less than about 5% loss of total CoQ10 in about 3-5 days in a about initial ratio of CoQ:AP:GG at 1:1:1 at about 50-55° C. The results are shown FIG. 5.

Example 4: Non-Conversion of CoQone to CoQnol when Solubilized in GG

This example showed that the combination of CoQone and GG as binary mixture alone did not exhibit any conversion of CoQone to CoQnol, but GG would readily and completely dissolve CoQone.

Procedure:
Prepare the following components in their respective ratio (by weight):
CoQone (about 25-60%)
GG (about 40-75%)
GG was added to an appropriately sized mixing vessel and heated to about 52° C. (±3°) while stirring. CoQone was added to the mixing vessel with GG to form a mixture. The mixture was stirred at about 52° C.). (±3° until CoQone was completely melted and solubilized in GG to attain a translucent solution. The mixing vessel was then flushed with a neutral, non-oxygenated gas until atmospheric air was displaced and the mixing vessel was sealed airtight. This mixture was then mixed for several days.

The initial mixture had the following components and ratios (by weight):

| CoQone | about 25% |
| GG     | about 75% |

The final mixture did not show any conversion of CoQone to CoQnol after about 3 weeks nor was there any degradation CoQ. GG completely dissolved CoQ10. Therefore, GG was a non-reactive solubilizing solvent for CoQ.

Example 5: Slow Conversion of CoQone to CoQnol when CoQone was Mixed Directly with AP This example showed the combination of CoQone and AP alone brought a slow conversion of CoQone to CoQnol. This was limited by kinetics at elevated temperatures—the desirable increased of CoQnol conversion and the undesirable increased of total CoQ degradation.

Procedure:
Prepare the following components in their respective ratio (by weight):
CoQone (about 50-80%)
AP (about 20-50%)

CoQone was added to an appropriately sized mixing vessel and melted at about 52° C.). (±3° while stirring. AP was added to the mixing vessel with CoQone to form a mixture. The mixture was gently stirred at about 52° C.). (±3° until no apparent dry AP was visible. The mixing vessel was then flushed with a neutral, non-oxygenated gas until atmospheric air was displaced and the mixing vessel was sealed airtight. This mixture was then mixed at elevated temperature for several days with periodic flushing of inert gas with the CoQone to CoQnol conversion rate being monitored.

The final mixture had the following components and ratios (by weight):

| | |
|---|---|
| CoQ | about 67-80% |
| AP | about 20-33% |

Figure 6:
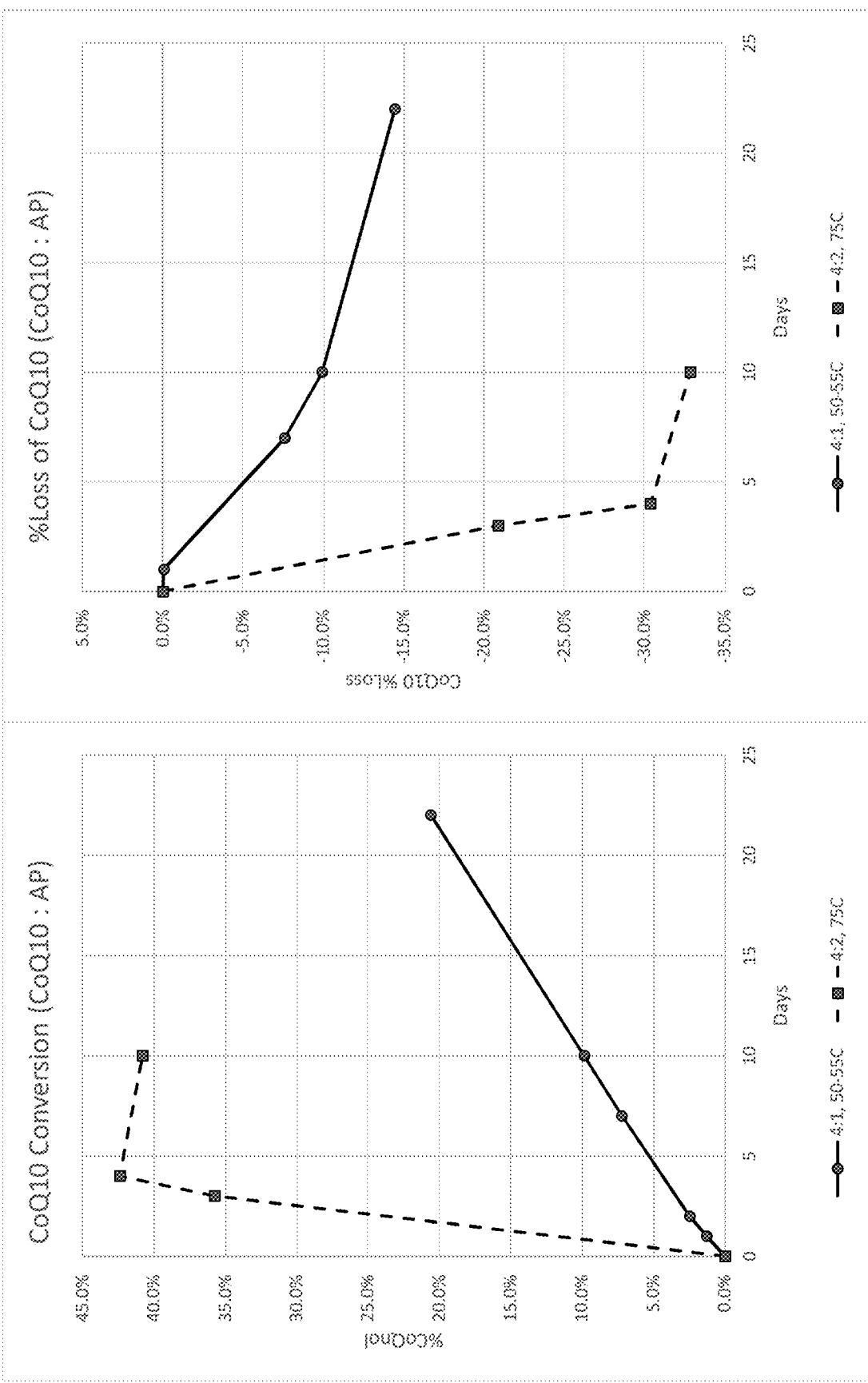
FIG. 6: CoQnol conversion rate over a period of about 21 days in the mixture of CoQone and AP alone at elevated temperatures.

The final mixture showed an about 20% conversion rate after about 3 weeks at about 50-55° C. in a binary mixture and a CoQone:AP ratio of about 4:1. CoQnol conversion was expected to increase more than about 20% beyond 3 weeks but this would be at the expense of total CoQ loss because of the long reaction duration. An elevated temperature of about 75° C. was intended to increase the AP solubility and promote the CoQnol conversion. At the elevated temperature of about 75° C. CoQnol conversion dramatically reached about 36% in about 3 days but total CoQ10 also degraded about 21% in about 3 days. Hence, reaction temperature more than about 75° C. may provide a diminishing return. The results are shown in FIG. 6.

Example 6: GG Solubilization of AP Prior to CoQone Addition

A method is provided that GG was first required to dissolve AP first at elevated temperatures (about 80-90° C.) and then cooled to about 60-70° C. The resulting solution of AP in GG was poured into CoQone powder. The reaction mixture was stirred in inert atmosphere until CoQnol production was complete for about 3-5 days and at about 50-60° C. Reduction to CoQnol is expected to be about 85%-95%.

Example 7: Headspace Comparison of Inert Gases

This example set forth a comparison and a method for converting CoQone to CoQnol utilizing two separate inert gases.

CoQ10, AP, and GG are provided in the weight ratio of about 4:2:4. The three components were placed in a mixing vessel kept stirred at about 52° C.). (±3°. The mixing vessel was flushed with a neutral, non-oxygenated gas until atmospheric air was displaced entirely by Nitrogen ($N_2$) or Argon (Ar) and sealed airtight. This mixture was then stirred at elevated temperatures for about 6-7 days until the target CoQnol conversion rate was reached.

Figure 7:
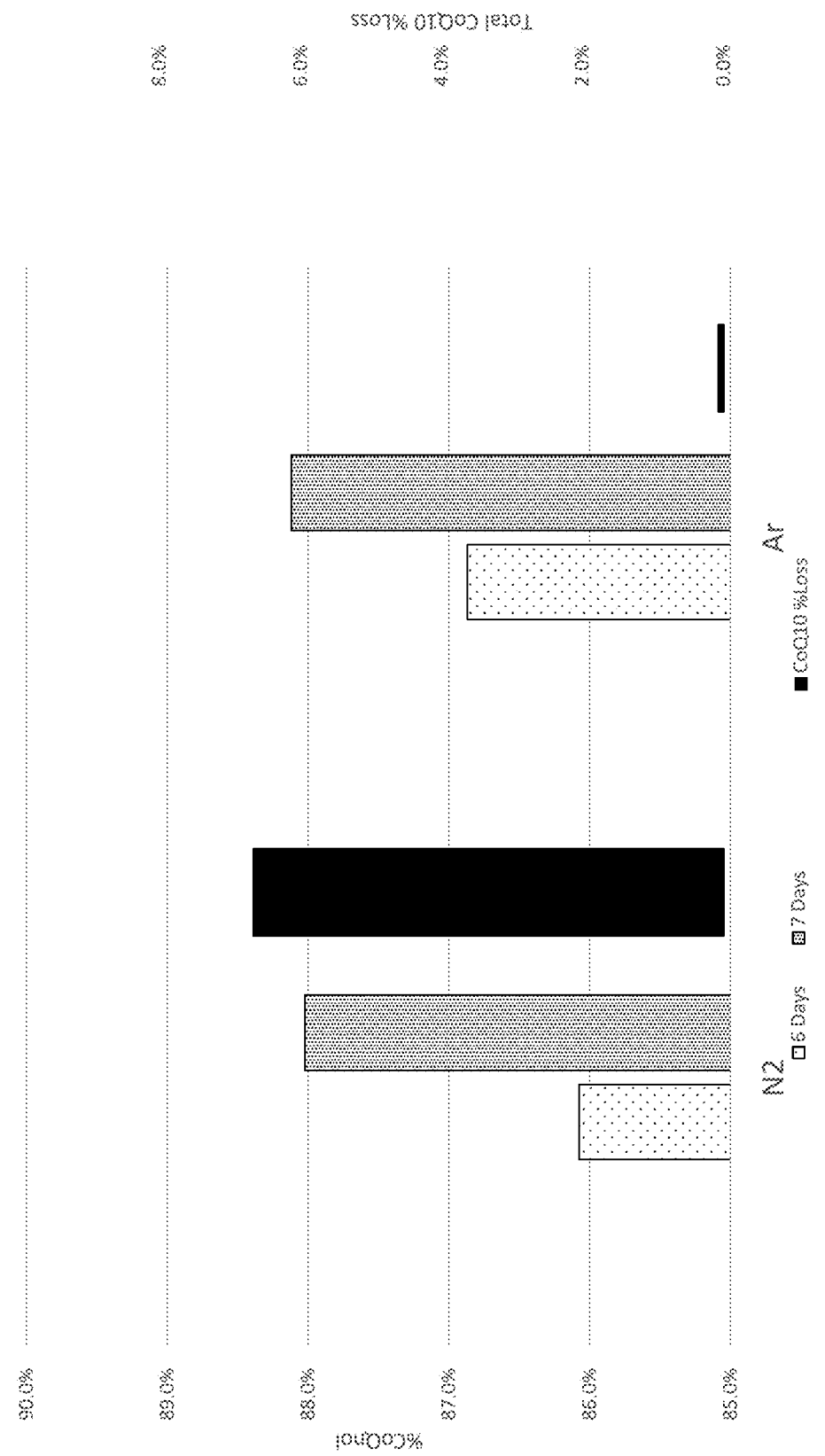
FIG. 7: Comparison of the CoQnol conversion rates in two different inert gases: nitrogen and argon.

Despite that different inert gases were used, the final mixtures showed similar CoQnol conversions on both about 6 days and about 7 days. The average CoQnol conversion of about 6 days and about 7 days in $N_2$ and Ar were about 87.0% and about 87.5%, respectively. The total CoQ10 loss in nitrogen-filled headspace was at about 7%. However, the total loss of CoQ10 in argon-filled headspace was remarkably and unexpectedly low at less than about 0.5%. See FIG. 7.

Without implying limitations, it may be generally desirable to undertake CoQone-to-CoQnol reactions in a mixture of CoQone:AP:GG at a ratio of about 4:2:4 at a temperature of less than about 55° C. for less than about 6 days in Ar to obtain a more than about 90% CoQnol conversion.

Example 8: Preparation of Softgels from the Compositions Prepared by Conversion of CoQone to CoQnol with AP and GG in a Manufacture Production Batch This example is to show that the methods for preparing the compositions in the lab batch scale (10-40 g) in the embodiments as described herein can be reproduced in a manufacture batch scale.

A manufacture batch was run according the preparation methods set forth in Example 1 with the following modifications. The total amount of CoQone:AP:GG mixtures was 20 kg. Argon was used to flush the mixing vessel until the atmospheric air was displaced. After the mixing vessel was sealed air-tight, this mixture of CoQone:AP:GG was then stirred at about 52° C.). (±2° for about six days with periodic flushing of Argon for about every 24 hours. The final composition showed a CoQnol conversion rate of about 91.6% without any measurable loss of the total CoQ. This result showed that production-size conversion of CoQnol can be achieved about 90% to about 95%.

The final composition in the sealed vessel was placed in a hopper for the encapsulation process in a softgel assembly line. The finished softgels were analyzed to determine that the weight percentage of CoQnol in total amount of CoQnol and CoQone is about 93%. The ratio of CoQnol to CoQone in the softgel remained unchanged. Softgels are hermetically sealed and the contents within the softgels are expected to be stable for at least about 2 years.

Example 9: Reduction of MK4one-to-MK4nol and MK7one-to-MK7nol by GG and AP

A method similar to the method in Example 1 was provided that the mixture MK4one and MK7one was added to the mixture of GG and AP, and the resulting reaction mixture was kept inert at about 50-55° C. for about 3-6 days. The conversions of MK4one-to-MK4nol and MK7one-to-MK7nol were about 12% and about 14%, respectively. The example showed that quinone-type structures were able to be reduced in combination with GG and AP. When the method described herein was carried out with MK7one alone, a similar conversion was achieved. Therefore, the method described herein can be applied to either MK4one, MK7one, or a mixture thereof.

Example 10: Reduction of Curcumin to Tetrahydorcurcumin (THC) by GG and AP

The method provided in Example 1 is expected to reduce curcumin to tetrahydorcurcumin (THC) in the presence of GG and AP.

Example 11: Reduction of Pyrroloquinoline Quinone (PQQone) to PQQnol by GG and APs A method provided in Example 1 is expected to reduce PQQone to PQQnol in the presence of GG and AP.

REFERENCES

Each of the following references is incorporated by reference in its entirety:

Al Rajabi A, Booth S L, Peterson J W, Choi S W, Suttie J W, Shea M K, et al. Deuterium-labeled phylloquinone has tissue-specific conversion to menaquinone-4 among Fischer 344 male rats. J Nutr. 2012; 142(5):841-5. Epub 2012 Mar. 23.

Barry, Robert (2010), The Power of Ubiquinol (ISBN: 0-9774356-5-2).

Campia I, Lussiana C, Pescarmona G, Ghigo D, Bosia A, Riganti C. Geranylgeraniol prevents the cytotoxic effects of mevastatin in THP-1 cells, without decreasing the beneficial effects on cholesterol synthesis. British journal of pharmacology. 2009, 158(7):1777-86. Epub 2009 Nov. 6.

Chopra R K, Reduced form of Coenzyme Q in high bioavailability stable dosage forms and related applications, U.S. Pat. No. 8,753,675, Jun. 17, 2014.

Crane F L, Hatefi Y, R L Lester and C Widmer (1957). Isolation of a quinone from beef heart mitochondria, BBA 25: 220-221.

Fantuzzi M., Solubilized CoQ-10, U.S. Pat. No. 8,124,072, Feb. 28, 2012.

Fantuzzi M, Ubiquinol and Alpha Lipoic Acid Compositions, U.S. Pat. No. 9,345,672, May 24, 2016.

Goldman R, Method for enhancing dissolution properties of relatively insoluble dietary supplements and product incorporating same, U.S. Pat. No. 6,056,971, May 2, 2000.

Grammel, H, and Ghosh R. "Redox-State Dynamics of Ubiquinone-10 Imply Cooperative Regulation of Photosynthetic Membrane Expression in *Rhodospirillum rubrum*." Journal of Bacteriology, American Society for Microbiology (ASM), July 2008.

Harshman S G, Shea M K, Fu X, Grusak M A, Smith D, Lamon-Fava S, et al. Atorvastatin Decreases Renal Menaquinone-4 Formation in C57BL/6 Male Mice. J Nutr. 2019; 149(3):416-21. Epub 2019 Feb. 13.

Hirota Y, Nakagawa K, Sawada N, Okuda N, Suhara Y, Uchino Y, et al. Functional characterization of the vitamin K2 biosynthetic enzyme UBIAD1. PloS one. 2015; 10(4): e0125737. Epub 2015 Apr. 16.

Houston M C, Treatment of Hypertension with Nutrition and Nutraceutical Supplements, Alternative and Complementary Therapies, Vol. 25, February 2019; and references on CoQ10 therein.

Lund, Pernille (2014), Q10 For Better Health and A Long Life (ISBN: 87-7776-111-1)

Marcuzzi A, Piscianz E, Zweyer M, Bortul R, Loganes C, Girardelli M, et al. Geranylgeraniol and Neurological Impairment: Involvement of Apoptosis and Mitochondrial Morphology. International journal of molecular sciences. 2016; 17(3):365. Epub 2016/03/16.

Mattila P, Lehtonen M, and Kumpulainen J, Comparison of In-Line Connected Diode Array and Electrochemical Detectors in the High-Performance Liquid Chromatographic Analysis of Coenzymes Q9 and Q10 in Food Materials, The Journal of Agricultural and Food Chemistry (2000), vol, 48, No. 4, p. 1229-1233.

Meganathan R., Kwon, O., "Biosynthesis of Menaquinone (Vitamin K2) and Ubiquinone (CoQ)", ASMscience.org, Dec. 23, 2009

Nakagawa K, Hirota Y, Sawada N, Yuge N, Watanabe M, Uchino Y, et al. Identification of UBIAD1 as a novel human menaquinone-4 biosynthetic enzyme. Nature. 2010; 468(7320):117-21. Epub 2010 Oct. 19.

Nickerson M L, Bosley A D, Weiss J S, Kostiha B N, Hirota Y, Brandt W, et al. The UBIAD1 prenyltransferase links menaquinone-4 [corrected] synthesis to cholesterol metabolic enzymes. Human mutation. 2013; 34(2):317-29. Epub 2012 Nov. 22.

Roginsky V A, Mohr D, Stocker R, Reduction of ubiquinone-1 by ascorbic acid is a catalytic and reversible process controlled by the concentration of molecular oxygen, Redox Report (1996) 2(1): p. 55-62.

Semeco, Arlene (2017), Nine Benefit of Coenzyme Q10 (www.healthline.com), Oct. 12, 2017; and references in CoQ10 therein.

Tan B, Annatto Extract Compositions, including geranyl geraniols and methods of use, U.S. Pat. No. 7,989,006, Aug. 2, 2011.

Tan B, Annatto Extract Compositions, including geranyl geraniols and methods of use, U.S. Pat. No. 8,293,290, Oct. 23, 2012

Tan B, Mueller A M. Tocotrienols in Cardiometabolic Diseases. In: Watson R, Preedy V, editors. Tocotrienols: Vitamin E beyond Tocopherol: AOCS/CRC Press; 2008. p. 257-73.

Tan B, CoQ10 (Ubiquinone, Ubiquinol), Vitamin A (Retinoid Acid, Retinol), Vitamin E (Tocotrienol, Tocopherol) and methods to use, U.S. Pat. No. 9,949,938, Apr. 24, 2018.

Udell R G, and Hari S P, Super Absorption Coenzyme Q10, U.S. Pat. No. 6,623,734, Sep. 23, 2003.

WholeFoods Interview, June 2007 with Frederick Crane by Richard Passwater.

www.noberlprize.org., Peter Mitchell Nobel Lecture, Dec. 8, 1978.

WholeFoods, March 2019: p. 64-68, The functions and absorption of the Ubiquinone and Ubiquinol.

WholeFoods, April 2019: p. 42-50, The absorption of Ubiquinone and Ubiquinol forms of Coenzyme Q10.

What is claimed is:

1. A method of preparing a composition comprising Compound C, comprising:

contacting Compound A having the formula of

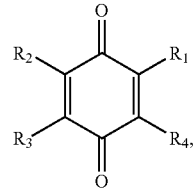

Formula I

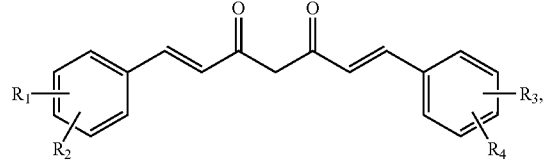

Formula VIII optionally in a solvent, wherein the solvent is free of ethanol, with Compound B having the formula of

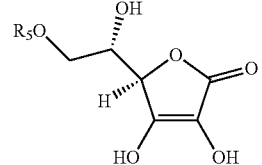

Formula II to form Compound C having the formula of

Formula III

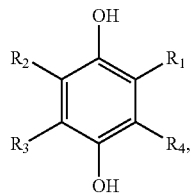

Formula VI

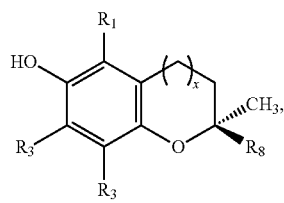

Formula X

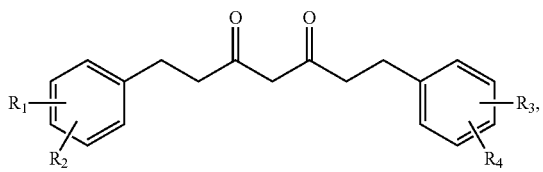

wherein:

R$_5$ is H, OH, NH$_2$, NO$_2$, R$_6$—C(O)—, optionally substituted carbocycle, optionally substituted aryl group, optionally substituted heteroaryl group, branched or unbranched alkyl alcohol, halo, branched or unbranched alkyl, branched or unbranched alkenyl, branched or unbranched alkenyl ester, amide, cyano, alkoxy, haloalkyl, aklylsulfonyl, nitrite, or alkylsulfanyl; and R$_1$, R$_2$, R$_3$, R$_4$, R$_6$, and R$_8$ are each, independently, H, OH, NH$_2$, NO$_2$, optionally substituted carbocycle, optionally substituted aryl group, optionally substituted heteroaryl group, branched or unbranched alkyl alcohol, halo, branched or unbranched alkyl, branched or unbranched alkenyl branched or unbranched carboxylic acid, branched or unbranched alkyl ester, branched or unbranched alkenyl ester, amide, cyano, alkoxy, haloalkyl, aklylsulfonyl, nitrite, or alkylsulfanyl; or R$_2$ and R$_3$ are together optionally substituted cycloalkyl, optionally substituted cycloheteroalkyl, optionally substituted aryl, or optionally substituted heteroaryl; and wherein the Compound A has the formula of Formula I-I

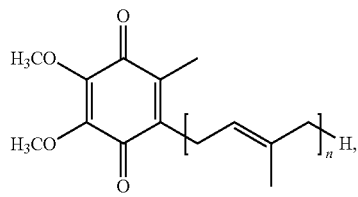

Formula I-II

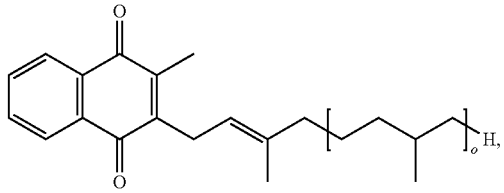

Formula I-III

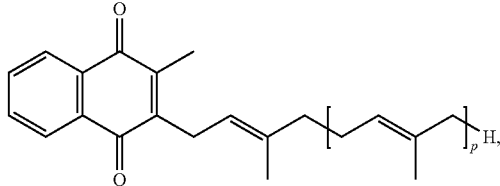

Formula I-IV

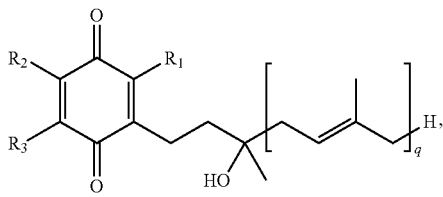

Formula I-V

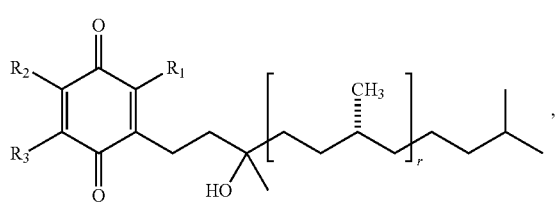

Formula VIII-I

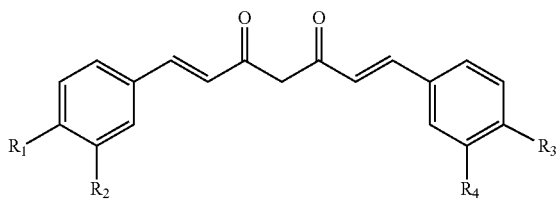

and wherein n, o, p, q, or r independently is 1-20.

2. The method of claim 1, wherein Compound B has the formula of

Formula II-I

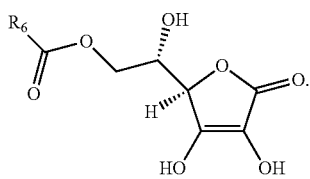

3. The method of claim 1, wherein the solvent is a non-toxic terpenoid having the formula of

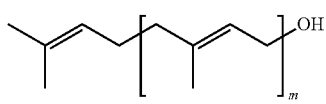

Formula V

Formula V and m is 0-10.

4. The method of claim 3, wherein the non-toxic terpenoid has the formula of

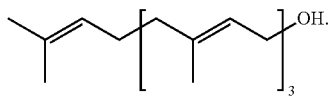

5. The method of claim 1, wherein the method comprises: contacting Compound A having the formula of

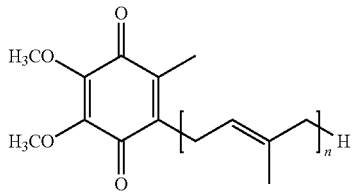

Formula I-I in the solvent having the formula of

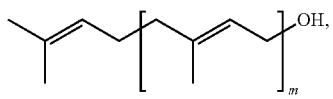

Formula V with Compound B having the formula of

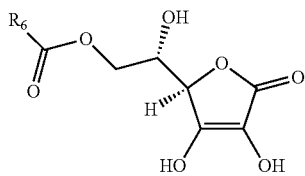

Formula II-I to form Compound C having the formula of

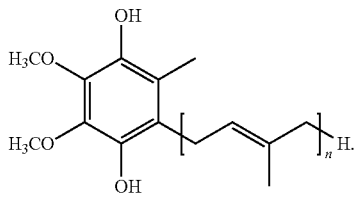

Formula III-I wherein m is 0-10.

6. The method of claim 5, wherein the method comprises: contacting Compound A having the formula of

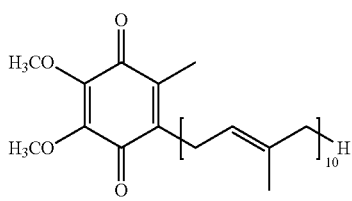

Formula I-I in the solvent having the formula of

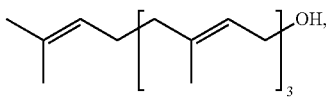

with Compound B having the formula of

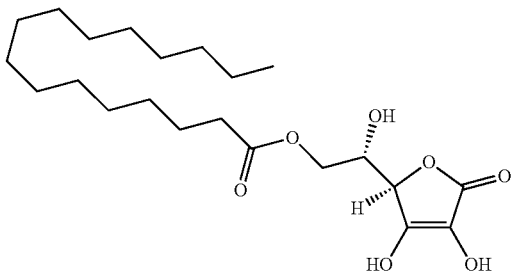 [SMILES: CCCCCCCCCCCCCCCC(=O)OC[C@H](O)[C@H]1OC(=O)C(O)=C1O]

to form the compound having the formula of

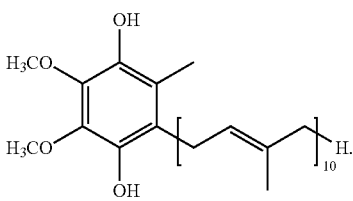

7. The method of claim 1, wherein the method comprises:
a. heating the solvent in a mixing vessel to about 35-75° C.;
b. adding Compound A to the solvent of the step a to form a translucent solution;
c. adding Compound B to the solution of step b to form a mixture and stirring the mixture;
d. replacing the air in the vessel with an inert gas and sealing the vessel air tight; and
e. stirring the mixture of step d for a period of time at an elevated temperature.

8. The method of claim 7, wherein the inert gas is Nitrogen or Argon.

9. The method of claim 7, wherein the elevated temperature is in a range of about 30-100° C., about 40-80° C. or about 50-70° C.

10. The method of claim 7, wherein the period of time is about 1 to about 13 days, about 2 to about 10 days, or about 3 to about 6 days.

11. The method of claim 7, wherein the starting weight ratio of Compound A:Compound B; the solvent is in a range of about 4:0.5:4 to about 4:4:4.

12. The method of claim 7, wherein the starting weight ratio of Compound A:Compound B; the solvent is about 4:2:4.

13. A composition prepared according to the method of claim 1, the composition comprising:
Compound A having the formula of

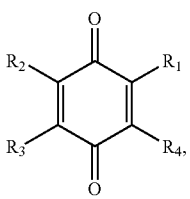

Formula I

-continued

Formula VIII

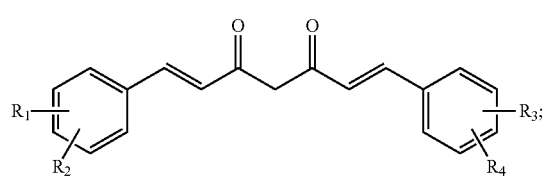

Compound B having the formula of

Formula II

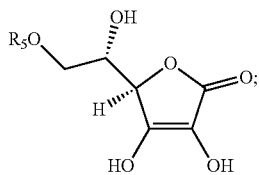

Compound C having the formula of

Formula III

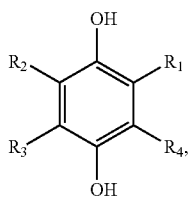

Formula VI

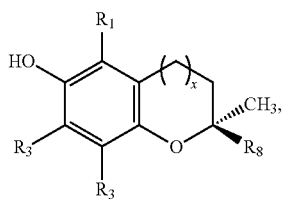

Formula X

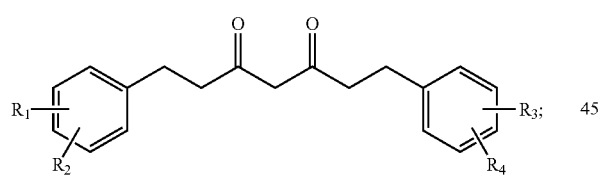

Compound D having the formula of

Formula IV

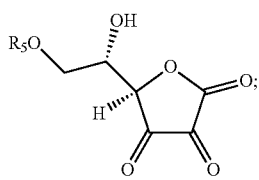

and
optionally a solvent with the proviso that the non-toxic solvent is not ethanol,
wherein:
$R_5$ is H, OH, $NH_2$, $NO_2$, $R_6$—C(=O)—, optionally substituted carbocycle, optionally substituted aryl group, optionally substituted heteroaryl group, branched or unbranched alkyl alcohol, halo, branched or unbranched alkyl, branched or unbranched alkenyl, branched or unbranched alkenyl ester, amide, cyano, alkoxy, haloalkyl, aklylsulfonyl, nitrite, or alkylsulfanyl; and $R_1$, $R_2$, $R_3$, $R_4$, $R_6$, and $R_8$ are each, independently, H, OH, $NH_2$, $NO_2$, optionally substituted carbocycle, optionally substituted aryl group, optionally substituted heteroaryl group, branched or unbranched alkyl alcohol, halo, branched or unbranched alkyl, branched or unbranched alkenyl, branched or unbranched carboxylic acid, branched or unbranched alkyl ester, branched or unbranched alkenyl ester, amide, cyano, alkoxy, haloalkyl, aklylsulfonyl, nitrite, or alkylsulfanyl; or $R_2$ and $R_3$ are together optionally substituted cycloalkyl, optionally substituted cycloheteroalkyl, optionally substituted aryl, or optionally substituted heteroaryl; and wherein the Compound A has the formula of Formula I-I

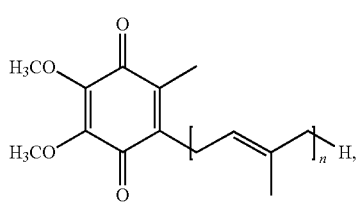

Formula I-II

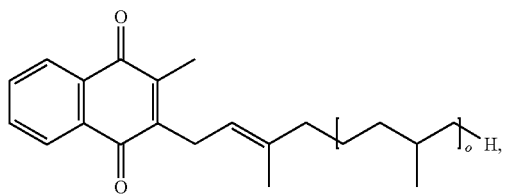

Formula I-III

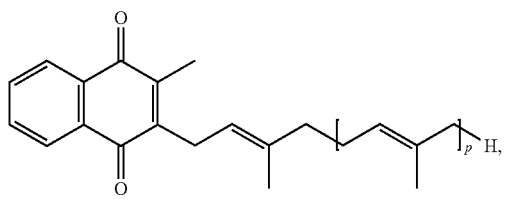

Formula I-IV

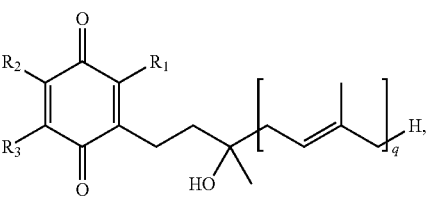

Formula I-V

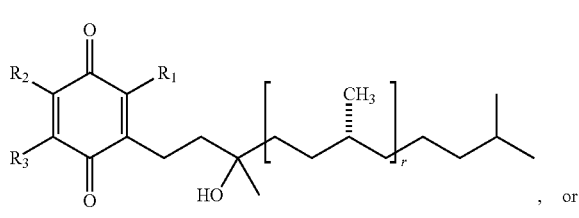

, or

-continued

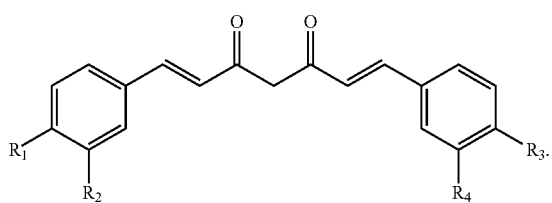

Formula VIII-I and wherein n, o, p, q, or r independently is 1-20.

14. The composition of claim 13, wherein the solvent is the non-toxic terpenoid having the formula of

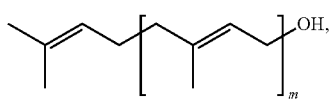

Formula V wherein m is 0-10.

15. The composition of claim 14, wherein the non-toxic terpenoid has the formula of

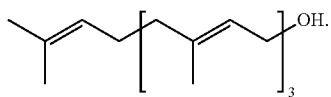

16. The composition of claim 13, wherein the weight ratio of the total amount of Compound A and Compound C:Compound B is in a range of about 5:1 to about 1:5, about 3:1 to about 1:3, or about 2:1 to about 1:2.

17. The composition of claim 13, wherein the weight ratio of Compound A:Compound C is in a range of about 99.9:0.1 to about 0.1:99.9, 40:60 to about 1:99, about 20:80 to about 1:99, about 15:85 to about 7:93, about 13:87 to about 7:93, about 13:87 to about 8:92, or about 13:87 to about 8:91.

18. The composition of claim 13, wherein the composition is formulated in a form suitable for oral consumption or oral administration and the form is selected from the group consisting of a softgel, a capsule, 2-piece liquid-filled capsule, a bar, confectionary, chocolate, a powder, an oral suspension, a tablet, a pill, a hard-shell, a truffle, a ganache, a truffle ganache, a gum, and a chewable form.

19. A method, the method comprising:
mitigating or treating statin-induced CoQ10 diseases in a subject comprising administering to the subject the composition of claim 13;
improving cardiac functions, increasing energy, increasing bone mineralization, prevention of joint osteophyte growth prevention and reversion of gall and kidney stones, reversal of arterial calcification, preventing statin-induced myopathy, preventing blood-thinning med-induced dementia, increasing myogenesis, preventing sarcopenia, preventing cancer-induced cachexia, increasing zest and thrive, preventing fibromyalgia, decreasing fatigue, preventing energy deficits, or improving general metabolic synthesis of proteins, CoQ10, or Vitamin K2 in a subject comprising administering to the subject the composition of claim 13;
increasing bioavailability and bioaccessibility of a second composition in a subject comprising administering to the subject the composition of claim 13 with the second composition;
increasing absorption into an endothelial or internal surface skin of a dermatological composition, comprising administering to a subject the composition of claim 13 with the dermatological composition;
improving mitochondrial function or increasing mitochondrial reproduction in a subject comprising administering to a subject the composition of claim 13;
improving neurological regeneration in a subject comprising administering to the subject the composition of claim 13; or
mitigating or treating nonalcoholic fatty liver in a subject comprising administering to a subject the composition of claim 13;
wherein the subject of any of the foregoing can optionally be a subject in need thereof.

20. The method of claim 7, wherein the temperature of step a, is about 45-65° C.

* * * * *